US012721898B2

(12) United States Patent
Low et al.

(10) Patent No.: US 12,721,898 B2
(45) **Date of Patent: *Sep. 1, 2026**

(54) FIBROBLAST ACTIVATION PROTEIN (FAP)—TARGETED ANTIFIBROTIC THERAPY

(71) Applicant: Purdue Research Foundation, West Lafayette, IN (US)

(72) Inventors: Philip Stewart Low, West Lafayette, IN (US); Spencer D. Lindeman, West Lafayette, IN (US); Ramesh Mukkamala, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 840 days.

This patent is subject to a terminal disclaimer.

(21) Appl. No.: 17/759,793

(22) PCT Filed: Jan. 29, 2021

(86) PCT No.: PCT/US2021/015902

§ 371 (c)(1),
(2) Date: Jul. 29, 2022

(87) PCT Pub. No.: WO2021/155288

PCT Pub. Date: Aug. 5, 2021

(65) Prior Publication Data

US 2024/0002408 A1 Jan. 4, 2024

Related U.S. Application Data

(60) Provisional application No. 62/968,618, filed on Jan. 31, 2020.

(51) Int. Cl.

| | |
|---|---|
| ***A61K 47/55*** | (2017.01) |
| ***A61P 35/00*** | (2006.01) |
| ***C07D 401/14*** | (2006.01) |
| ***C07F 5/02*** | (2006.01) |

(52) U.S. Cl.
CPC .............. *A61K 47/55* (2017.08); *A61P 35/00* (2018.01); *C07D 401/14* (2013.01); *C07F 5/025* (2013.01)

(58) Field of Classification Search
CPC ....... A61P 35/00; A61K 47/55; C07D 401/14; C07F 5/025
See application file for complete search history.

(56) References Cited

U.S. PATENT DOCUMENTS

| | | | | |
|---|---|---|---|---|
| 11,504,364 | B2 * | 11/2022 | Pujala | C07D 401/12 |
| 12,397,069 | B2 * | 8/2025 | Low | A61K 51/0497 |
| 2008/0280856 | A1 | 11/2008 | Cohen et al. | |
| 2010/0234431 | A1 | 9/2010 | Jiaang et al. | |
| 2020/0330624 | A1 * | 10/2020 | Yang | A61K 51/0455 |
| 2022/0105208 | A1 * | 4/2022 | Low | A61K 49/0052 |
| 2023/0100158 | A1 | 3/2023 | Low et al. | |

FOREIGN PATENT DOCUMENTS

| | | | | |
|---|---|---|---|---|
| WO | WO-2018111989 | A1 * | 6/2018 | A61P 35/04 |
| WO | WO-2019154859 | A1 | 8/2019 | |
| WO | WO-2019154886 | A1 * | 8/2019 | A61K 51/0459 |
| WO | 2020081522 | | 4/2020 | |
| WO | WO-2021016392 | A1 | 1/2021 | |
| WO | WO-2021155288 | A1 | 8/2021 | |
| WO | WO-2021155292 | A1 | 8/2021 | |

OTHER PUBLICATIONS

Cheng, Hong Sheng, Yun Sheng Yip, Eldeen Kai Yi Lim, Walter Wahli, and Nguan Soon Tan. "PPARs and tumor microenvironment: the emerging roles of the metabolic master regulators in tumor stromal-epithelial crosstalk and carcinogenesis." Cancers 13, No. 9 (2021): 2153. (Year: 2021).*

"European Application Serial No. 21748282.7, Response to Communications Pursuant to Rules 161 and 162 EPC filed Nov. 10, 2022", 21 pgs.

"U.S. Appl. No. 17/759,814, Supplemental Preliminary Amendment filed Jun. 22, 2023", 12 pgs.

"European Application Serial No. 21748466.6, Extended European Search Report mailed Jan. 30, 2024", 8 pgs.

"European Application Serial No. 21748282.7, Extended European Search Report mailed Mar. 13, 2024", 8 pgs.

"European Application Serial No. 21748282.7, Response filed Aug. 8, 2024 to Extended European Search Report mailed Mar. 13, 2024", 28 pgs.

(Continued)

*Primary Examiner* — James H Alstrum-Acevedo
*Assistant Examiner* — Carolyn L. Ladd
(74) *Attorney, Agent, or Firm* — Mueting Raasch Group

(57) ABSTRACT

A compound of formula $F_a$-L-$I_a$ (A) or $F_a$-$I_a$ (B), wherein $F_a$ is a fibroblast activation protein alpha (FAPα) targeting moiety, L is a linker, and $I_a$ is an inhibitor of a signaling pathway necessary for fibrosis in cancer-associated fibroblasts (CAFs); a pharmaceutical composition comprising same; and methods for treating a tumor, a cancer or a fibrotic disease in a subject.

15 Claims, 10 Drawing Sheets

(56) References Cited

OTHER PUBLICATIONS

"European Application Serial No. 21748466.6, Response filed Aug. 8, 2024 to Extended European Search Report mailed Jan. 30, 2024", 27 pgs.
Hettiarachchi, S. U, "Targeting Myofibroblasts for Novel Imaging and Therapeutic Applications in Idiopathic Pulmonary Fibrosis", American Journal of Respiratory and Critical Care Medicine; American Thoracic Society 2019 International Conference, American Thoracic Society, US, vol. 199, No. B103, [Online]. Retrieved from the Internet: URL: https : www.atsjournals.org doi abs 10.1164 ajrccm-conference.2019.199.1_MeetingAbstracts.A4087, (Jan. 1, 2019), A4087.
Sarah, E Poplawski, "Identification of Selective and Potent Inhibitors of Fibroblast Activation Protein and Prolyl Oligopeptidase", Journal of Medicinal Chemistry, vol. 56, No. 9, (May 9, 2013), 30 pgs.
"U.S. Appl. No. 17/759,814, Preliminary Amendment filed w Application Jul. 29, 2022", 12 pgs.
"International Application Serial No. PCT US2021 015907, International Preliminary Report on Patentability mailed Aug. 11, 2022", 8 pgs.
"International Application Serial No. PCT US2021 015902, International Preliminary Report on Patentability mailed Aug. 11, 2022", 8 pgs.
"European Application Serial No. 21748466.6, Response to Communication Pursuant to Rules 161 and 162 EPC filed Nov. 10, 2022", 20 pgs.
"International Application Serial No. PCT/US2021/015902, International Search Report mailed Jun. 4, 2021", 4 pgs.
"International Application Serial No. PCT/US2021/015902, Invitation to Pay Additional Fees and Partial Search Report mailed Apr. 5, 2021", 2 pgs.
"International Application Serial No. PCT/US2021/015902, Written Opinion mailed Jun. 4, 2021", 6 pgs.
"International Application Serial No. PCT/US2021/015907, International Search Report mailed Jun. 4, 2021", 4 pgs.
"International Application Serial No. PCT/US2021/015907, Invitation to Pay Additional Fees and Partial Search Report mailed Apr. 5, 2021", 2 pgs.
"International Application Serial No. PCT/US2021/015907, Written Opinion mailed Jun. 4, 2021", 6 pgs.

* cited by examiner

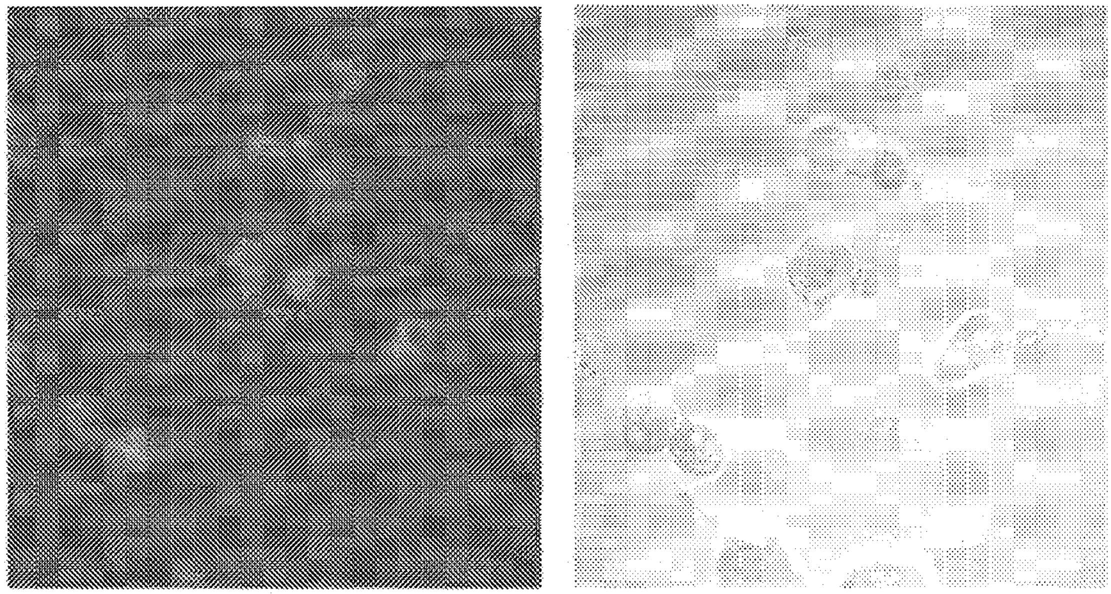
10 nM FAP1-FITC with U87MG glioblastoma cells
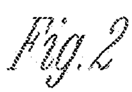
Fig. 2

100 nM FAP1-Rhodamine in Hs894 cancer-associated fibroblasts 100 nM FAP1-Rhodamine + competition in Hs894 cancer-associated fibroblasts

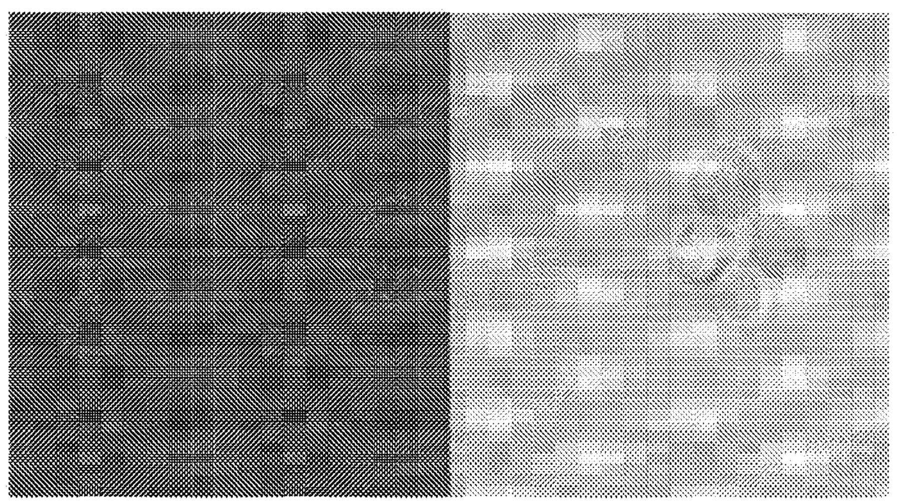
100 nM FAP1-Rhodamine in HT1080 fibrosarcoma cells
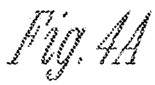
Fig. 4A
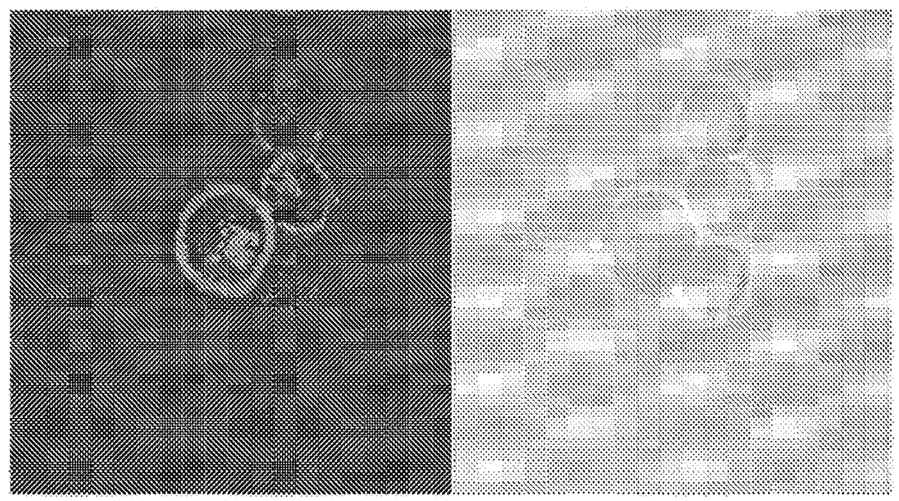
100 nM FAP1-Rhodamine in HT1080-FAP fibrosarcoma cells
Fig. 4B

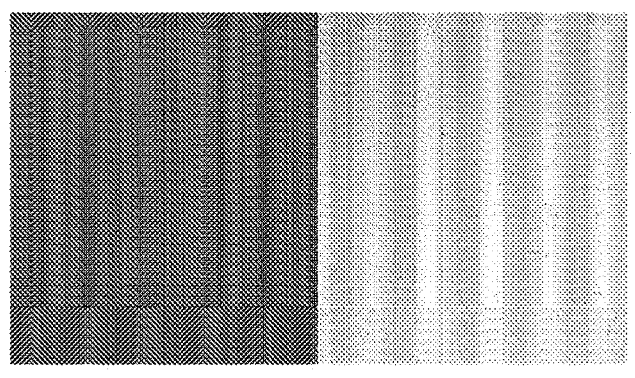
100 nM FAP1-FITC with HLF-FAP cells
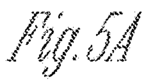
Fig. 5A
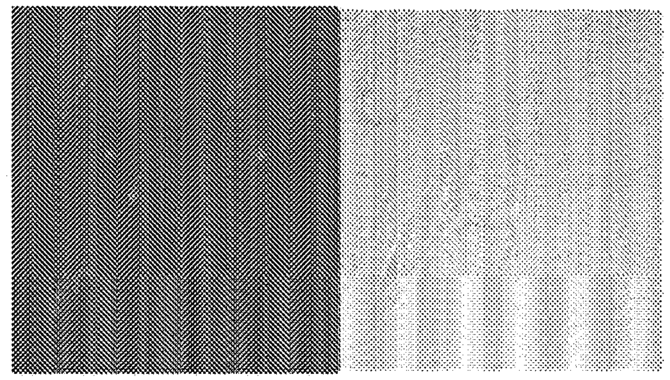
100 nM FAP1-FITC with HLF-FAP at 4°C for 1 hour
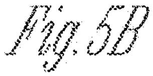
Fig. 5B
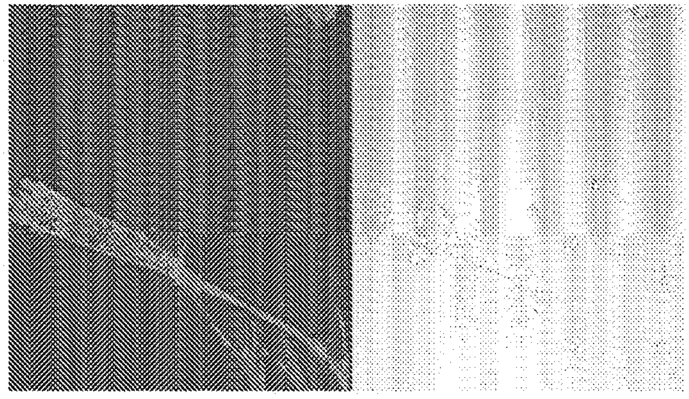
100 nM FAP1-FITC with HLF-FAP at 37°C for 1 hour
Fig. 5C

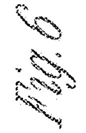
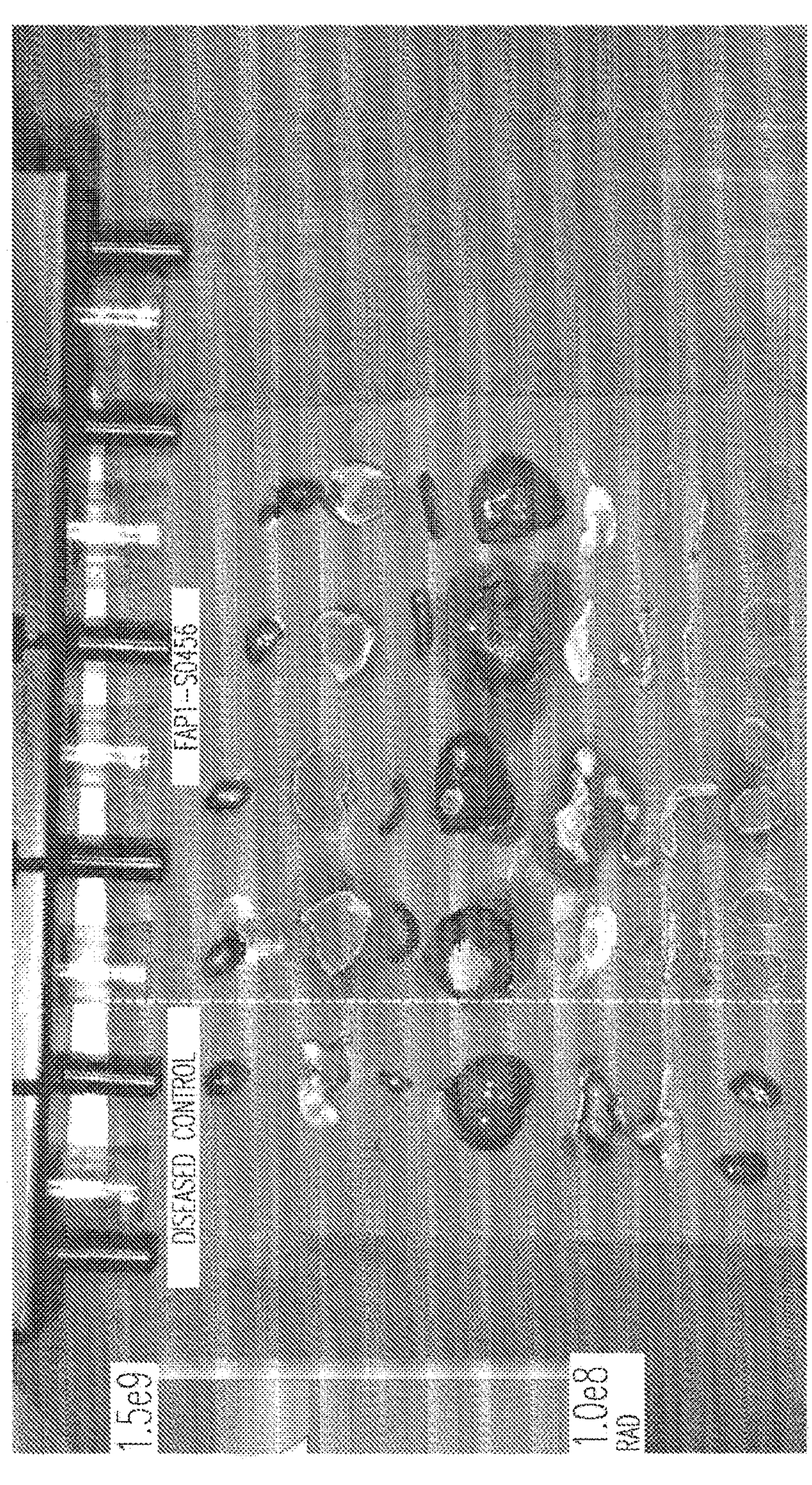
5 NMOL OF FAP1-S0456 IN MICE WITH PULMONARY FIBROSIS AT DAY 14 OF THE DISEASE MODE, 3 HOURS POST INJECTION

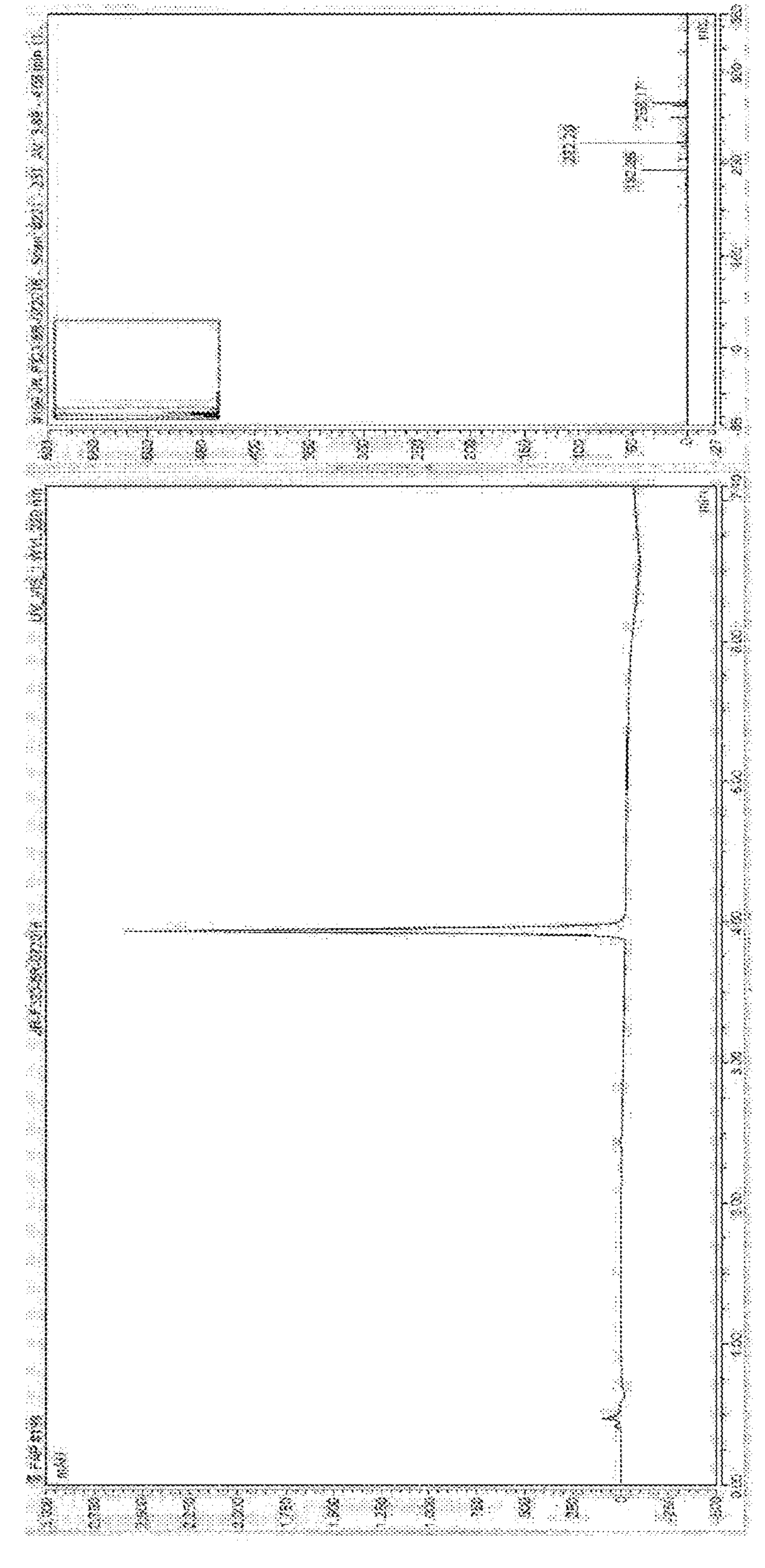
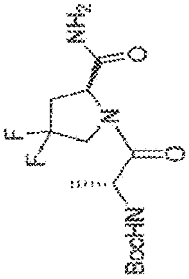
Fig. 7

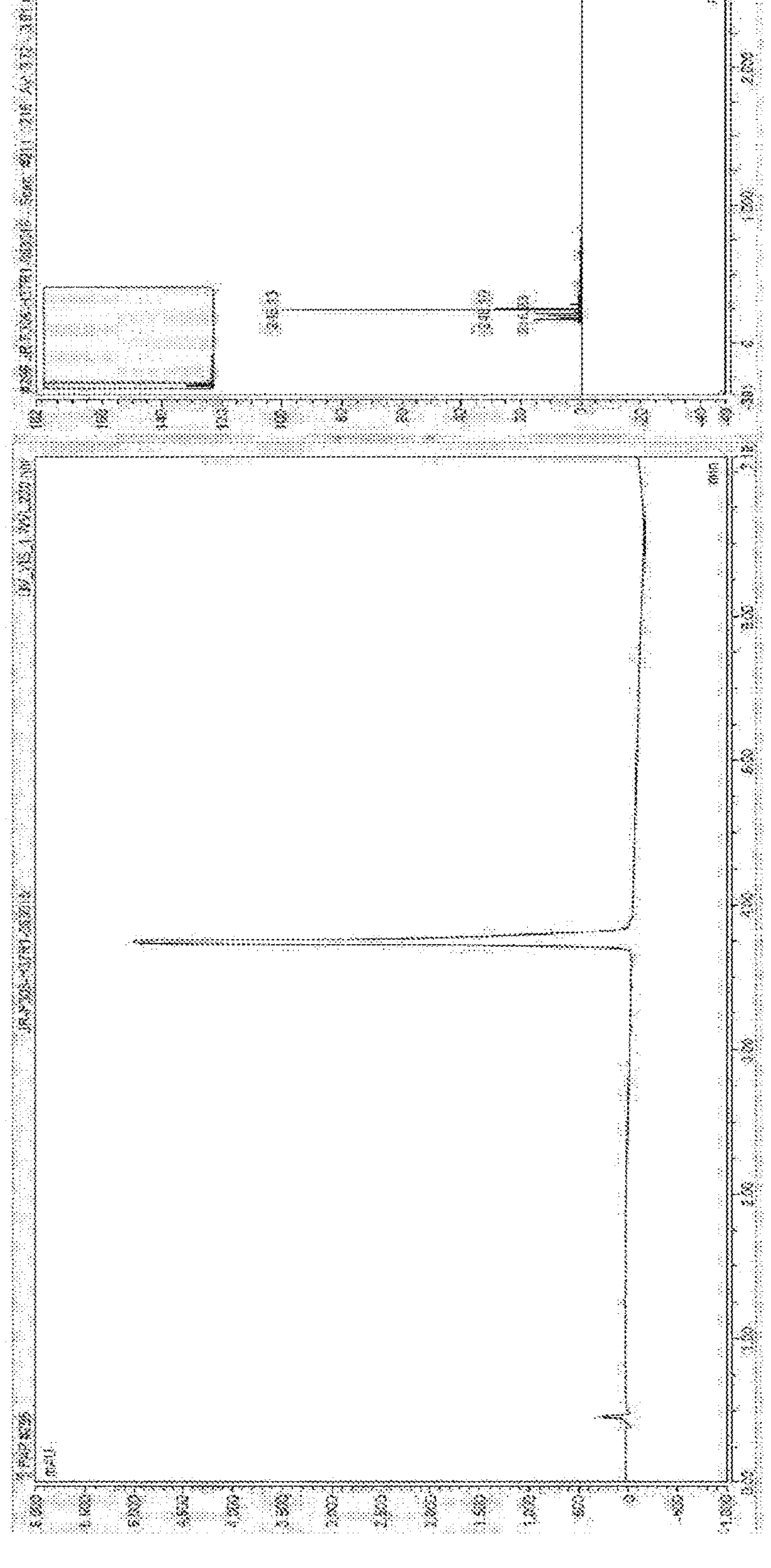
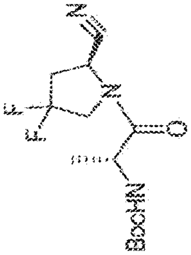
Fig. 8

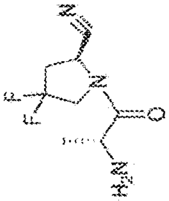
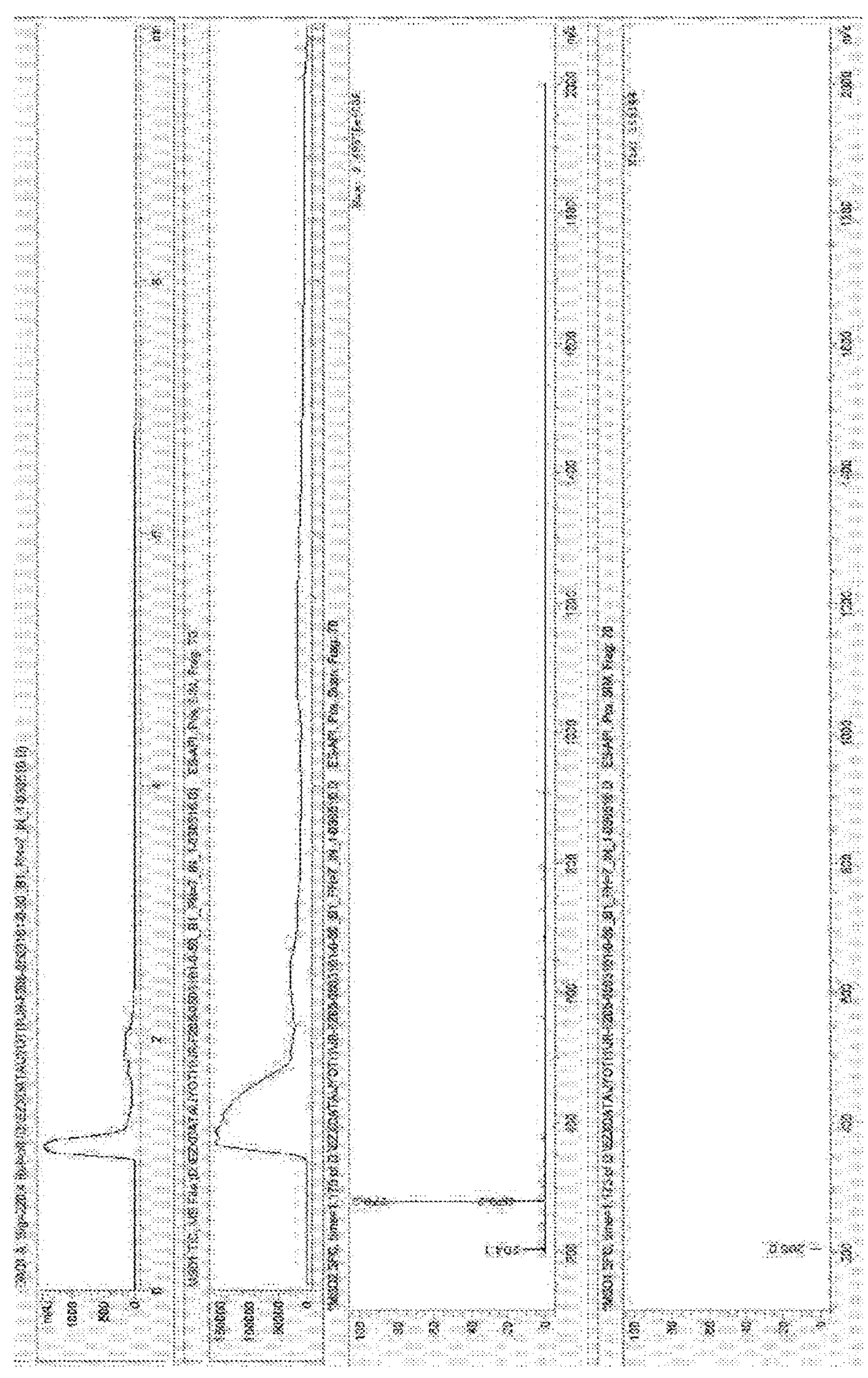
Fig. 9

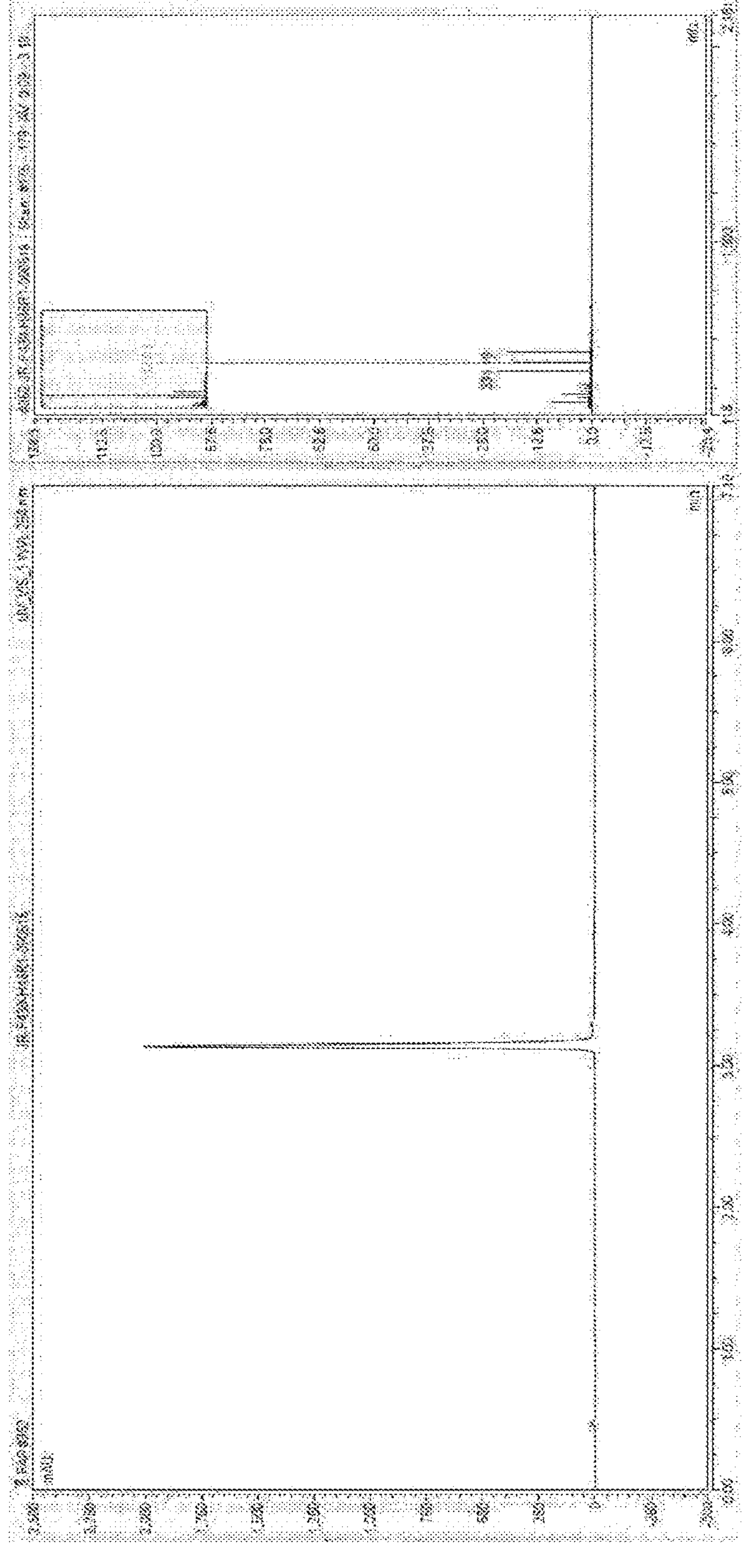
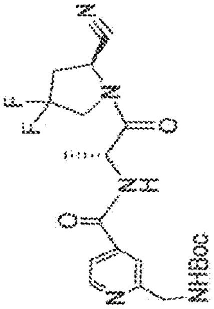
Fig. 10

FIBROBLAST ACTIVATION PROTEIN (FAP)—TARGETED ANTIFIBROTIC THERAPY

CROSS REFERENCE TO RELATED APPLICATION

This application is a U.S. national stage filing under 35 U.S.C. 371 from International Application No. PCT/US2021/015902, filed on 29 Jan. 2021, and published as WO 2021/155288 A1 on 8 Aug. 2021, which claims priority to U.S. provisional patent application No. 62/968,618, which was filed on Jan. 31, 2020, and which is hereby incorporated by reference in its entirety.

TECHNICAL FIELD

The present application relates to a compound of formula $F_a$-L-$I_a$ (A) or $F_a$-$I_a$ (B), wherein $F_a$ is a fibroblast activation protein alpha (FAPα) targeting moiety, L is a linker, and $I_a$ is an inhibitor of a signaling pathway necessary for fibrosis in cancer-associated fibroblasts (CAFs); and methods for treating a tumor, a cancer or a fibrotic disease in a subject.

BACKGROUND

The survival and proliferation of a tumor is dependent on the percentage of tumor stroma (TSP). A high TSP is associated with poorer long-term patient survival compared to low TSP (>50% vs. ≤50% respectively). The TSP is also a significant prognostic factor for tumor relapse, growth, and metastasis.

Cancer-associated fibroblasts (CAFs) are abundant in the tumor stroma and perform several important functions to promote tumorigenesis. These functions include cytokine secretion as well as extracellular matrix (ECM) production and remodeling. This results in angiogenesis to promote tumor growth, signaling factors to increase chemoresistance, denser ECM to create an immunosuppressive environment, and enhanced cell motility to direct metastasis. These mechanisms are well-documented and parallel the behavior of pathogenic fibroblasts in fibrotic diseases.

SUMMARY

The instant disclosure relates to compounds of formula (A) or (B)

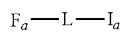

(A)

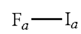

(B)

wherein $F_a$ comprises a fibroblast activation protein alpha (FAPα) targeting moiety with a molecular weight below 10,000 Daltons; L is a linker; and $I_a$ comprises an inhibitor of a signaling pathway associated with fibrosis in cancer-associated fibroblasts (CAFs).

The disclosure also relates to compounds the compounds of formula (A) or (B) wherein $F_a$ is a FAPα targeting moiety with a molecular weight below 10,000 Daltons; L is a linker; and $I_a$ is an inhibitor of a signaling pathway necessary for fibrosis in CAFs.

The disclosure also relates compound of formula (A) or (B):

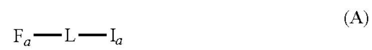

(A)

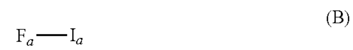

(B)

or a pharmaceutically acceptable salt thereof, wherein:

$F_a$ is a FAP targeting moiety having a structure represented by the following formula (X):

(X)

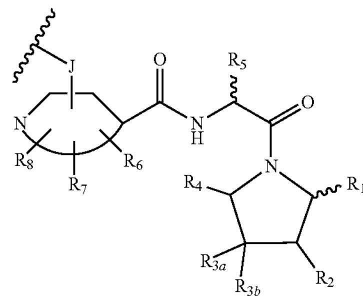

wherein:

$R_1$ is selected from the group consisting of —H, —CN, —$B(OH)_2$, —C(O)alkyl, —C(O)aryl, —C═CC(O)aryl, —C═C—$S(O)_2$aryl, —$CO_2H$, —$SO_3H$, —$SO_2NH_2$, —$PO_3H_2$, and 5-tetrazolyl, $R_2$, $R_{3a}$, $R_{3b}$ and $R_4$ are each independently selected from the group consisting of —H, —OH, halogen, —$C_{1-6}$alkyl, —O—$C_{1-6}$alkyl, and —S—$C_{1-6}$alkyl, $R_5$ is —$CH_3$, $R_6$, $R_7$, and $R_8$ are each independently selected from the group consisting of —H, —OH, oxo, halogen, $CF_3$, —$C_{1-6}$alkyl, —O—$C_{1-6}$alkyl, —S—$C_{1-6}$alkyl, —$NR_9R_{10}$, —$OR_{11}$, —$Het_2$, and —$Ar_2$; each of —$C_{1-6}$alkyl being optionally substituted with from 1 to 3 substituents selected from —OH and halogen;

$R_9$, $R_{10}$, and $R_{11}$ are each independently selected from the group consisting of —H, —OH, oxo, halogen, $CF_3$, —$C_{1-6}$alkyl, —O—$C_{1-6}$alkyl, —S—$C_{1-6}$alkyl, and —$Ar_3$, $Ar_2$ and $Ar_3$ are each independently a 5- or 6-membered aromatic monocycle optionally comprising 1 or 2 heteroatoms selected from O, N, and S; each of $Ar_2$ and $Ar_3$ being optionally and independently substituted with from 1 to 3 substituents selected from —$NR_{12}R_{13}$, —$C_{1-6}$alkyl, —O—$C_{1-6}$alkyl, and —S—$C_{1-6}$ alkyl, $R_{12}$ and $R_{13}$ are each independently selected from the group consisting of —H, —OH, $CF_3$, —$C_{1-6}$alkyl, —O—$C_{1-6}$alkyl, and —S—$C_{1-6}$alkyl;

$Het_2$ is a 5- or 6-membered non-aromatic monocycle optionally comprising 1 or 2 heteroatoms selected from O, N and S; $Het_2$ being optionally substituted with from 1 to 3 substituents selected from —$NR_{14}R_{15}$, —$C_{1-6}$alkyl, —O—$C_{1-6}$alkyl, and —S—$C_{1-6}$alkyl, $R_{14}$ and $R_{15}$ are each independently selected from the group consisting of —H, —OH, halogen, $CF_3$, —$C_{1-6}$alkyl, —O—$C_{1-6}$alkyl, and —S—$C_{1-6}$alkyl, the fragment:

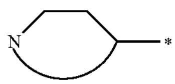

represents a 5- to 10-membered N-containing aromatic or non-aromatic mono- or bicyclic heterocycle, said heterocycle optionally further comprising 1 to 3 heteroatoms selected from O, N, and S, wherein * indicates an attachment point to a carbonyl as shown in formula (X); and J is selected from the group consisting of a bond, —$C_{1-3}$alkyl, —$C_{1-3}$alkyl-NH—, C═O, and —O—;

when present, L is a linker;

$I_a$ is an inhibitor of a signaling pathway necessary for fibrosis in CAFs; and the compound is not

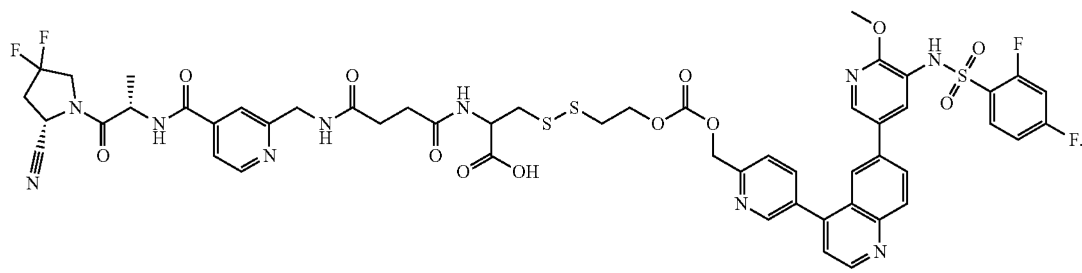

For example, in Formula (X), $R_1$ can be —CN, —$CH_2$CN or —$B(OH)_2$. For example, in Formula (X), $R_2$ can be hydrogen.

For example, in Formula (X), $R_1$ can be —CN, —$CH_2$CN or —$B(OH)_2$ and $R_2$ can be hydrogen.

For example, in Formula (X), $R_{3a}$ and $R_{3b}$ can be halogen. In exemplary compounds of Formula (X), $R_{3a}$ and $R_{3b}$ can be fluoro. For example, in Formula (X), $R_{3a}$ and $R_{3b}$ can be hydrogen.

For example, in Formula (X), $R_4$ can be hydrogen.

For example, in Formula (X), The fragment:

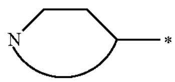

can be

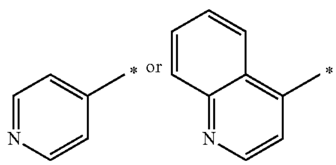

For example, in Formula (X), $R_6$, $R_7$, and $R_8$ can be hydrogen.

For example, in Formula (X), $R_6$ and $R_7$ can be hydrogen.

For example, in Formula (X), $R_8$ can both be hydrogen or chloro.

For example, in Formula (X), J can be selected from the group consisting of a bond, —$CH_2$—, —$CH_2$—NH—, and —O—.

The disclosure also relates compound of formula (A) or (B):

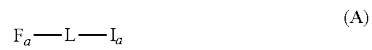

(A)

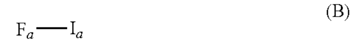

(B)

or a pharmaceutically acceptable salt thereof, wherein: $F_a$ is a FAP targeting moiety having a structure represented by the following formula (Y):

(Y)

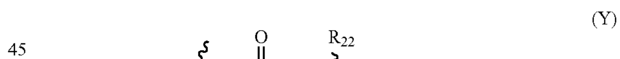

wherein:

Z is selected from the group consisting of

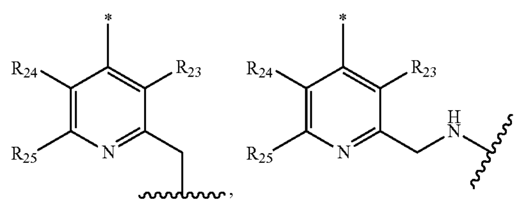

-continued

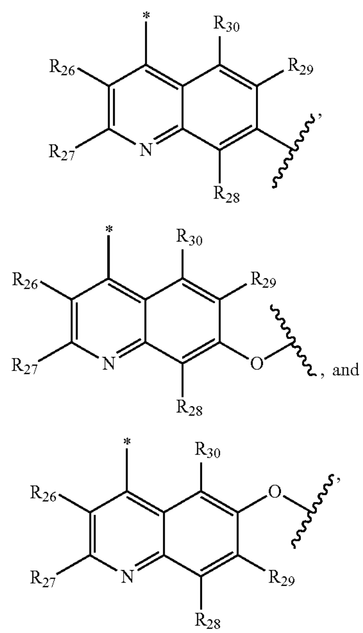

, and wherein * indicates an attachment point to a carbonyl as shown in formula (Y);

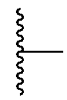

indicates an attachment point to L in formula (A) and L in formula (B);

$R_{20a}$ and $R_{20b}$ are the same or different and are each independently selected from the group consisting of hydrogen, halogen, and $C_{1-4}$alkyl;

$R_{21}$ is selected from the group consisting of $C_{1-4}$alkyl, nitrile, isonitrile, and boronic acid;

$R_{22}$ is —$CH_3$;

$R_{23}$ and $R_{24}$ are the same or different, and are each independently selected from the group consisting of hydrogen, halogen, and $C_{1-4}$alkyl;

$R_{25}$ is selected from the group consisting of hydrogen, methoxy, halogen, $CF_3$, and $C_{1-4}$alkyl;

$R_{26}$ and $R_{27}$ are the same or different, and are each independently selected from the group consisting of hydrogen, halogen, and $C_{1-4}$alkyl;

$R_{28}$, $R_{29}$, and $R_{30}$ are the same or different, and are each independently selected from the group consisting of hydrogen, methoxy, halogen, $CF_3$, and $C_{1-4}$ alkyl; and the compound is not

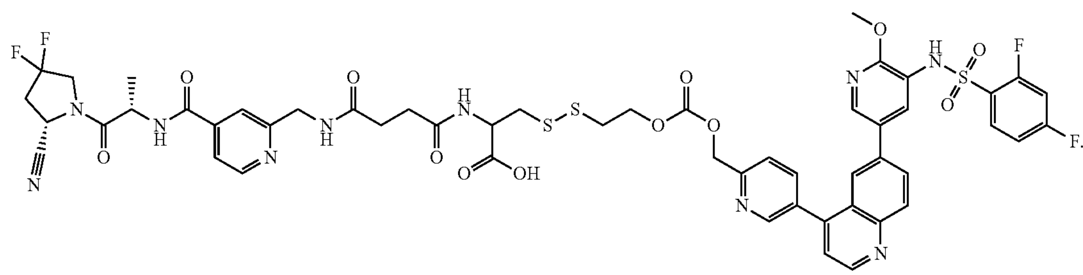 [SMILES: COc1ncc(-c2ccc3nccc(-c4ccc(COC(=O)OCCSSCC(NC(=O)CCC(=O)NCc5cc(C(=O)N[C@@H](C)C(=O)N6CC(F)(F)C[C@H]6C#N)ccn5)C(=O)O)nc4)c3c2)cc1NS(=O)(=O)c1ccc(F)cc1F]

For example, in Formula (Y), $R_{20a}$ and $R_{20b}$ can be halogen. For example, in Formula (Y), $R_{20a}$ and $R_{20b}$ can be fluoro. For example, in Formula (Y), $R_{20a}$ and $R_{20b}$ can be hydrogen.

For example, in Formula (Y), $R_{21}$ can be $—CH_2CN$ or boronic acid. For example, in Formula (Y), $R_{23}$ and $R_{25}$ can be hydrogen.

For example, in Formula (Y), $R_{24}$ can be hydrogen or chloro.

For example, in Formula (Y), $R_{26}$, $R_{27}$, $R_{28}$, $R_{29}$, and $R_{30}$ can be hydrogen.

The disclosure also relates compound of formula (A) or (B):

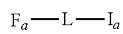
(A)

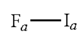
(B)

or a pharmaceutically acceptable salt thereof, wherein: $F_a$ is a FAP targeting moiety selected from the group consisting of:

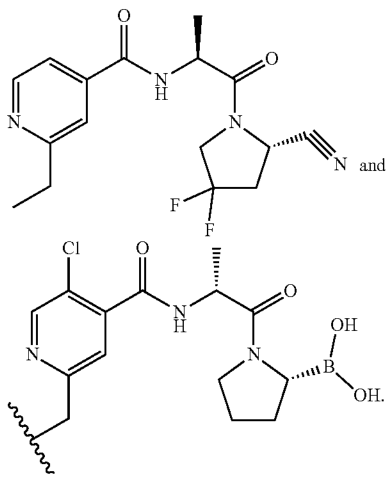

L can be

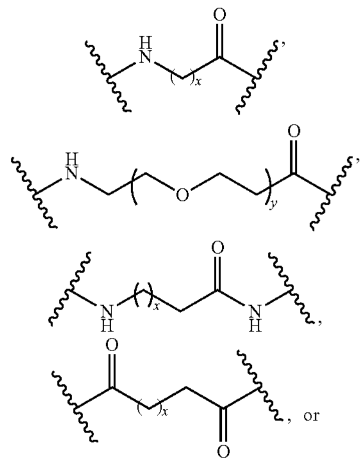

or

-continued

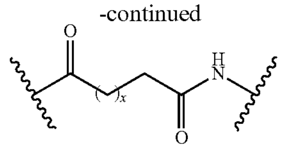

x is an integer from 0 to 10: and y is an integer from 3 to 100.

In any of the compounds encompassed by Formula (A) or Formula (B), L can be

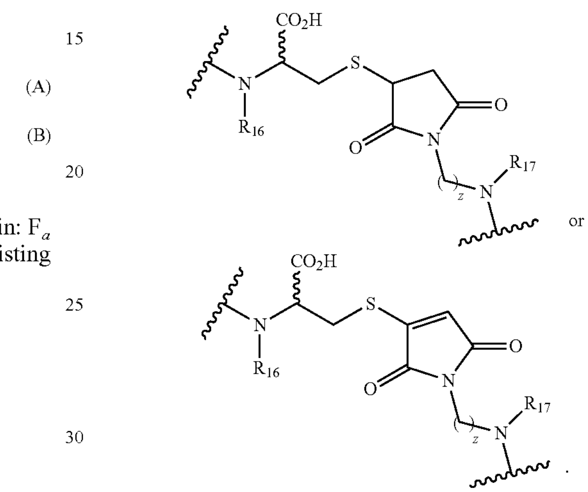

In any of the compounds encompassed by Formula (A) or Formula (B), L can be

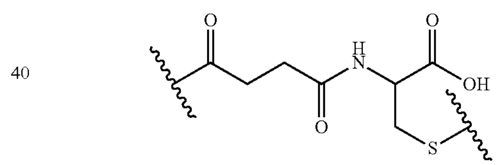

In any of the compounds encompassed by Formula (A) or Formula (B), L can be

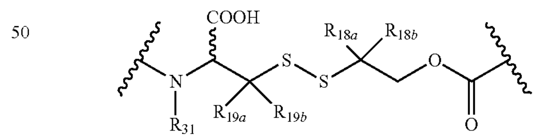

wherein $R_{18a}$, $R_{18b}$, $R_{19a}$, and $R_{19b}$ can independently be H or $C_{1-6}$alkyl; and $R_{31}$ can be H or $C_{1-6}$alkyl.

In any of the compounds encompassed by Formula (A) or Formula (B), $I_a$ can be a kinase inhibitor for TGFβRI/Smad. In any of the compounds encompassed by Formula (A) or Formula (B), $I_a$ can be a kinase inhibitor for Wnt/β-catenin. In any of the compounds encompassed by Formula (A) or Formula (B), $I_a$ can be a kinase inhibitor for VEGFR1, VEGFR2, VEGFR3, FGFR1, FGFR2, or PDGFR. In any of the compounds encompassed by Formula (A) or Formula (B), $I_a$ can be a kinase inhibitor for FAK or ROCK. In any of the compounds encompassed by Formula (A) or Formula (B), $I_a$ can be a pan kinase inhibitor for PI-3 kinase/mTOR. In any of the compounds encompassed by Formula (A) or Formula (B), $I_a$ can be a radical of:

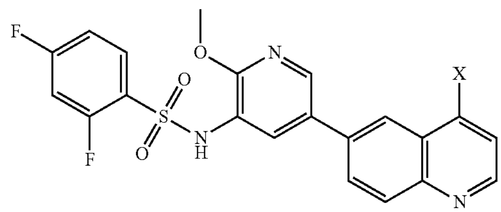

wherein X is

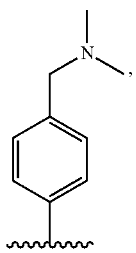

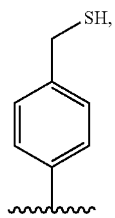

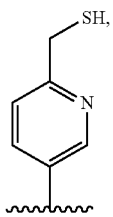

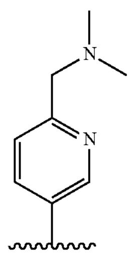

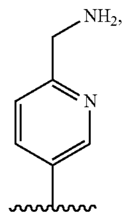

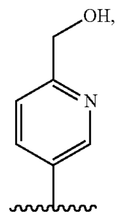

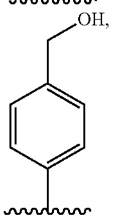

or

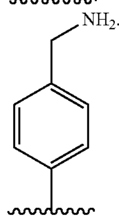

In any of the compounds encompassed by Formula (A) or Formula (B), la can be:

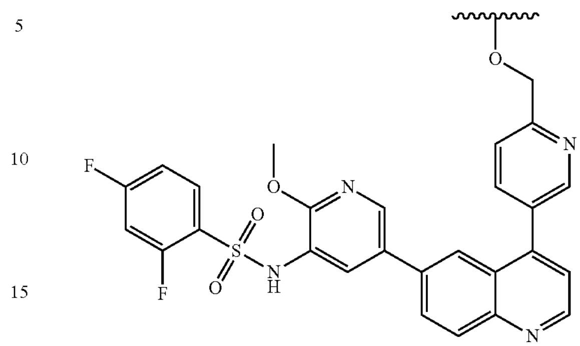

The targeting ligand to FAPα can have a binding affinity to FAP in the range between about 1 nM to about 25 nM.

Also provided are pharmaceutical compositions comprising an above-described compound and one or more pharmaceutically acceptable excipients.

The disclosure also relates to methods of treating a cancer (for example a solid tumor) in a subject in need thereof. The tumor microenvironment (TIE) of cancers contemplated for treatment with the methods disclosed herein in can comprises one or more cancer associated fibroblasts (CAFs). The method comprises administering to the subject a therapeutically effective amount of a compound of the disclosure.

The administered compound can reduce collagen I deposition into the TME from activated fibroblasts. The administered compound can comprise an antifibrotic agent effective against cancer cells and/or CAFs.

The CAF-containing TME can comprise additional stromal cells, including mesenchymal stem cells (MSCs), adipocytes and immune cells such as T cells, natural killers and macrophages.

Collagen I in the extracellular matrix of the TME of a cancer contemplated for treatment with the methods disclosed herein in can be reduced by administration of a compound disclosed herein.

The administered compound can reduce the hydroxyproline production of fibroblasts.

The cancer can be selected from the group consisting of lung cancer, bone cancer, pancreatic cancer, skin cancer, cancer of the head, cancer of the neck, cutaneous melanoma, intraocular melanoma, uterine cancer, ovarian cancer, endometrial cancer, leiomyosarcoma, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland cancer of the parathyroid gland, non-small cell lung cancer, small cell lung cancer, cancer of the adrenal gland, sarcoma of soft tissue, cancer of the urethra, cancer of the penis, prostate cancer, chronic leukemia, acute leukemia, lymphocytic lymphomas, pleural mesothelioma, cancer of the bladder, Burkitt's lymphoma, cancer of the ureter, cancer of the kidney, renal cell carcinoma, carcinoma of the renal pelvis, neoplasms of the central nervous system (CNS), primary CNS lymphoma, spinal axis tumors, brain stem glioma, pituitary adenoma, cholangiocarcinoma, Hurthle cell thyroid cancer, and adenocarcinoma of the gastroesophageal junction.

This disclosure further provides a method of treating a cancer (e.g., solid tumor) in a subject by modulating the profibrotic behavior of CAFs. The method comprises the steps of providing to the subject a therapeutically effective amount of compound $F_a$-L-$I_a$, wherein $F_a$ is a targeting ligand to FAPα that has a molecular weight below 10,000 Daltons, L is a releasable linker, and IL is a therapeutic drug that has an inhibitory effect on profibrotic signaling pathways in fibroblasts; in more particular aspects, the inhibitor IL is a pan PI-3 Kinase inhibitor.

The disclosure also provides a method of reducing collagen I deposition by activated fibroblasts by administering to a subject in need thereof a compound of formula (A) or (B).

The disclosure also provides a method for reducing the hydroxyproline production of CAFs.

The disclosure also relates to a method of treating a cancer (e.g., a solid tumor) by reducing a tumor stroma of the cancer in a subject. The method comprises the steps of delivering a compound disclosed herein to a tumor microenvironment of a patient, the tumor microenvironment comprising at least one CAF, with a therapeutically effective amount of a compound of the disclosure. The method can further comprise monitoring i) reduction of tumor stroma extracellular matrix deposition, and ii) reduction and/or prevention of metastasis of tumor cells.

The disclosure also relates to a method of treating a fibrotic disease or disorder in a subject in need thereof. The fibrotic disease or disorder can be treated by reducing fibrosis. The method comprises administering to the subject a therapeutically effective amount of a compound of formula (A) or (B). The fibrotic disease or disorder can be pulmonary fibrosis (e.g., idiopathic pulmonary fibrosis), liver fibrosis, heart fibrosis, kidney fibrosis, mediastinal fibrosis, retroperitoneal cavity fibrosis, bone marrow fibrosis (aka, myelofibrosis), skin fibrosis, or scleroderma (systemic sclerosis).

The compound can reduce collagen I deposition from activated fibroblasts.

The subject can be a mouse tumor model induced by injecting $5\times10^6$ MDA-MB231, OVCAR-3, and HEC-1B cells in 0.2 mL sterile PBS subcutaneously in the right hind flank of the female nu/nu mice.

These and other features, aspects and advantages of the present disclosure will become better understood with reference to the following figures, associated descriptions, and claims.

BRIEF DESCRIPTION OF THE DRAWINGS

FIG. 2 is confocal data of 10 nM FAP1-FITC binding to U87MG glioblastoma cells.

FIG. 4A is confocal data of 100 nM FAP1-Rhodamine binding to HT1080 fibrosarcoma cells.

FIG. 4B is confocal data of 100 nM FAP1-Rhodamine binding to HT1080-FAP fibrosarcoma cells.

FIG. 5A is confocal data of 100 nM FAP1-FITC binding to HLF cells.

FIG. 5B is confocal data of 100 nM FAP1-FITC binding to HLF-FAP cells at 4° C.

FIG. 5C is confocal data of 100 nM FAP1-FITC binding to HLF-FAP cells at 37° C.

FIG. 6 is the NIR imaging of FAP1-S0456 in mice induced with pulmonary fibrosis at day 14 of the disease model, 3 hours post injection of 5 nmol of conjugate.

FIG. 7 shows the chemical structure and an LC/MS trace for Compound 3.

FIG. 8 shows the chemical structure and an LC/MS trace for Compound 4.

FIG. 9 shows the chemical structure and an LC/MS trace for Compound 5.

FIG. 10 shows the chemical structure and an LC/MS trace for Compound 7.

DETAILED DESCRIPTION

Figure 1:
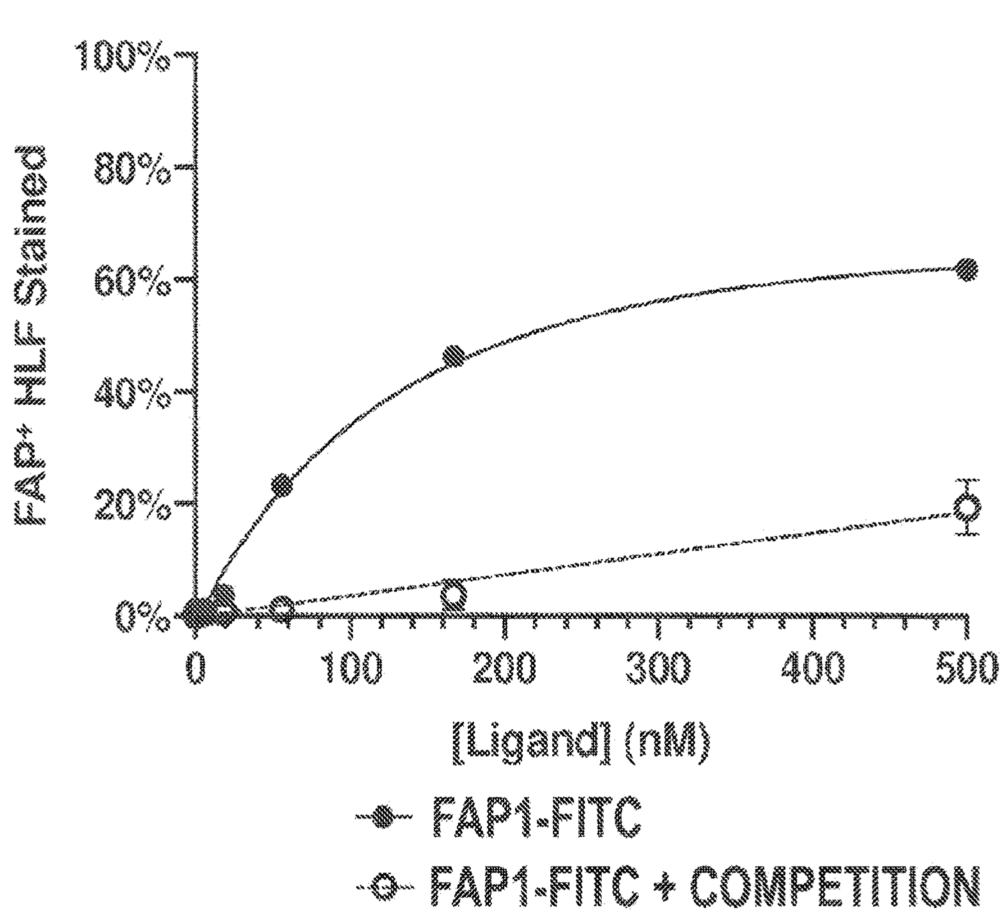
FIG. 1 is the binding and competition curves for FAP1-FITC using HLF-FAP cells, co-stained with a FAP mAb conjugated to APC dye and gated for FAP$^+$ events only.
Figure 3A:
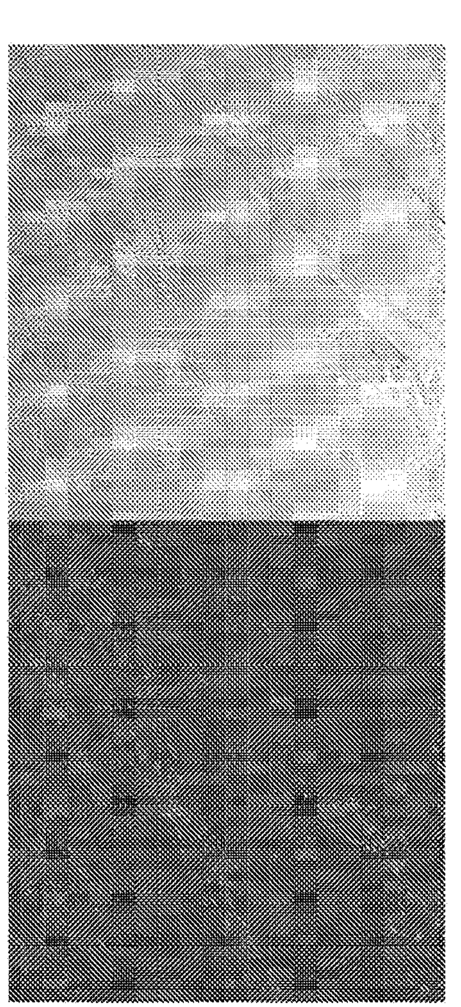
FIG. 3A is confocal data of 100 nM FAP1-Rhodamine binding to Hs894 cancer-associated fibroblasts
Figure 3B:
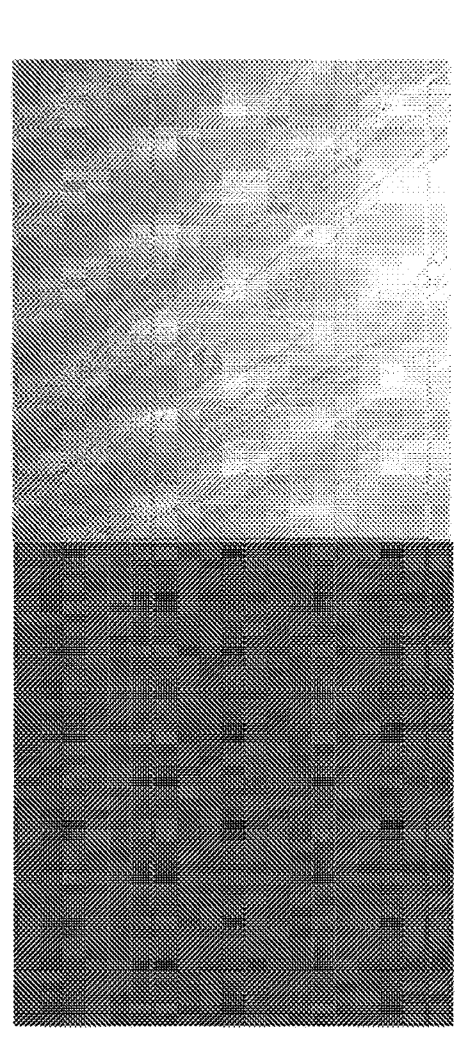
FIG. 3B is confocal data of 100 nM FAP1-Rhodamine+ competition (100× excess of FAP1 ligand) binding to Hs894 cancer-associated fibroblasts

While the concepts of the present disclosure are illustrated and described in detail in the figures and descriptions herein, results in the figures and their description are to be considered as examples and not restrictive in character; it being understood that only the illustrative embodiments are shown and described and that all changes and modifications that come within the spirit of the disclosure are desired to be protected.

Compounds

The disclosure relates to compounds of formula (A) or (B)

$$F_a\text{—}L\text{—}I_a \quad (A)$$

$$F_a\text{—}I_a \quad (B)$$

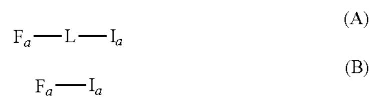

wherein $F_a$ comprises a fibroblast activation protein alpha (FAPα) targeting moiety with a molecular weight below 10,000 Daltons; L is a linker; and $I_a$ comprises an inhibitor of a signaling pathway necessary for fibrosis in cancer-associated fibroblasts (CAFs).

The disclosure also relates to compounds the compounds of formula (A) or (B) wherein $F_a$ is a FAPα targeting moiety with a molecular weight below 10,000 Daltons; L is a linker; and $I_a$ is an inhibitor of a signaling pathway necessary for fibrosis in CAFs.

The FAPα targeting moiety can have a molecular weight: below 10,000 Daltons; below 90,000 Daltons; below 80,000 Daltons; below 70,000 Daltons; below 60,0000 Daltons; below 50,000 Daltons; below 40,000 Daltons; below 30,000 Daltons; below 20,000 Daltons; below 10,000 Daltons; or below 5,000 Daltons.

In each of the foregoing and each of the following embodiments, it is to be understood that the formulae include and represent all pharmaceutically acceptable salts of the compound formulae. It is appreciated that certain functional groups, such as the hydroxy, amino, and like groups form complexes and/or coordination conjugates with water and/or various solvents, in the various physical forms of the compound of formula (A) or (B). It is understood that the formulae depicted throughout the disclosure include and represent hydrates and/or solvates of compounds of formula (A) or (B). It is also to be understood that the non-hydrates and/or non-solvates of compounds of formula (A) or (B) are described by such formula, as well as the hydrates and/or solvates of the compounds of formula (A) or (B).

The disclosure also relates to compound of formula (A) or (B):

$F_a$—L—$I_a$ (A)

$F_a$—$I_a$ (B)

or a pharmaceutically acceptable salt thereof, wherein $F_a$ is a FAPα targeting moiety having a structure represented by the following formula (X)

(X)

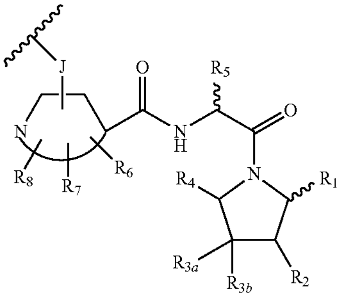

wherein $R_1$ is selected from the group consisting of —H, —CN, —B(OH)$_2$, —C(O)alkyl, —C(O)aryl, —C═C—C(O)aryl, —C═C—S(O)$_2$aryl, —CO$_2$H, —SO$_3$H, —SO$_2$NH$_2$, —PO$_3$H$_2$, and 5-tetrazolyl;

$R_2$, $R_{3a}$, $R_{3a}$ and $R_4$ are each independently selected from the group consisting of —H, —OH, halogen, —C$_{1-6}$ alkyl, —O—C$_{1-6}$alkyl, and —S—C$_{1-6}$alkyl;

$R_5$ is —CH$_3$;

$R_6$, $R_7$, and $R_8$ are each independently selected from the group consisting of —H, —OH, oxo, halogen, CF$_3$, —C$_{1-6}$alkyl, —O—C$_{1-6}$alkyl, —S—C$_{1-6}$alkyl, —NR$_9$R$_{10}$, —OR$_{11}$, —Het$_2$, and —Ar$_2$; each of —C$_{1-6}$ alkyl being optionally substituted with from 1 to 3 substituents selected from —OH and halogen;

with from 1 to 3 substituents selected from —NR$_{12}$R$_{13}$, —C$_{1-6}$alkyl, —O—C$_{1-6}$alkyl, and —S—C$_{1-6}$ alkyl;

$R_{12}$ and $R_{13}$ are each independently selected from the group consisting of —H, —OH, CF$_3$, —C$_{1-6}$alkyl, —O—C$_{1-6}$alkyl, —S—C$_{1-6}$alkyl, and halogen; and Het$_2$ is a 5- or 6-membered non-aromatic monocycle optionally comprising 1 or 2 heteroatoms selected from O, N and S; Het$_2$ being optionally substituted with from 1 to 3 substituents selected from —NR$_{14}$R$_{15}$, —C$_{1-4}$ alkyl, —O—C$_{1-6}$alkyl, and —S—C$_{1-6}$alkyl; and $R_{14}$ and $R_{15}$ are each independently selected from the group consisting of —H, —OH, halogen, CF$_3$, —C$_{1-6}$alkyl, —O—C$_{1-6}$alkyl, and —S—C$_{1-6}$alkyl;

the fragment:

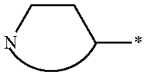 [SMILES: *CCCN]

represents a 5- to 10-membered N-containing aromatic or non-aromatic mono- or bicyclic heterocycle, said heterocycle optionally further comprising 1 to 3 heteroatoms selected from O, N, and S, wherein * indicates an attachment point to carbonyl as shown in formula (X);

J is selected from the group consisting of a bond, —C$_{1-3}$alkyl, —C$_{1-3}$alkyl-NH—, C═O, and —O—; and the fragment:

indicates a point of attachment of the FAPα binding ligand to the Linker, L, or the inhibitor moiety, IL, wherein the point of attachment can be through any of the carbon atoms of the 5- to 10-membered N-containing aromatic or non-aromatic mono- or bicyclic heterocycle in formula (X);

L is a linker;

$I_a$ is an inhibitor of a signaling pathway necessary for fibrosis in CAFs; and the compound is not

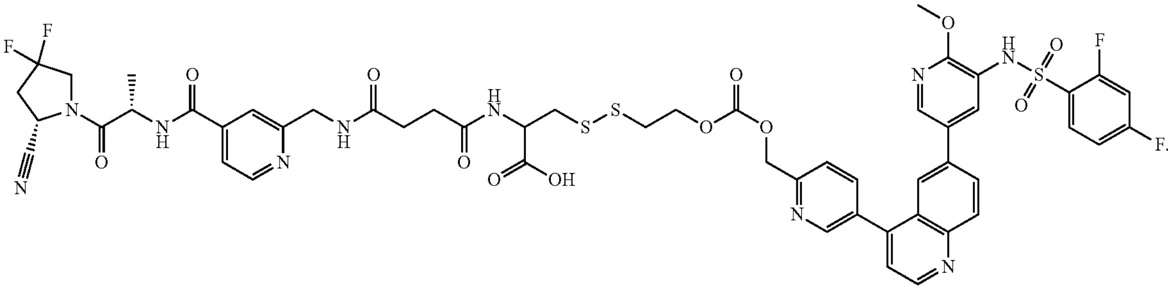 [SMILES: COc1ncc(-c2ccc3nccc(-c4ccc(COC(=O)OCCSSCC(NC(=O)CCC(=O)NCc5cc(C(=O)N[C@@H](C)C(=O)N6CC(F)(F)C[C@H]6C#N)ccn5)C(=O)O)nc4)c3c2)cc1NS(=O)(=O)c1ccc(F)cc1F]

$R_9$, $R_{10}$, and $R_{11}$ are each independently selected from the group consisting of —H, —OH, oxo, halogen, CF$_3$, —C$_{1-6}$alkyl, —O—C$_{1-6}$alkyl, —S—C$_{1-6}$alkyl, and —Ar$_3$;

Ar$_2$, and Ar$_3$ are each independently a 5- or 6-membered aromatic monocycle optionally comprising 1 or 2 heteroatoms selected from O, N, and S, each of Ar$_2$, and Ar$_3$ being optionally and independently substituted For example, in Formula (X), $R_1$ can be —CN, —CH$_2$CN or —B(OH)$_2$. For example, in Formula (X), $R_2$ can be hydrogen.

For example, in Formula (X), $R_1$ can be —CN, —CH$_2$CN or —B(OH)$_2$ and $R_2$ can be hydrogen.

For example, in Formula (X), $R_{3a}$ and $R_{3b}$ can be halogen. For example, in Formula (X), $R_{3a}$ and $R_{3b}$ can be fluoro. For example, in Formula (X), $R_{3a}$ and $R_{3b}$ can be hydrogen.

For example, in Formula (X), $R_4$ can be hydrogen.

For example, in Formula (X), the fragment:

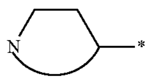 [SMILES: *CCCN]

can be

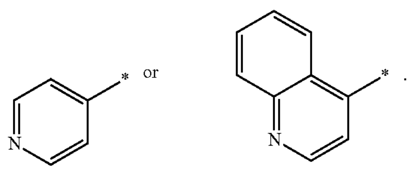 [SMILES: *c1ccncc1 ; *c1ccnc2ccccc12]

or .

For example, in Formula (X), $R_6$, $R_7$, and $R_8$ can be hydrogen.

For example, in Formula (X), $R_6$ and $R_7$ can be hydrogen.

For example, in Formula (X), $R_8$ can both be hydrogen or chloro.

For example, in Formula (X), J can be selected from the group consisting of a bond, —$CH_2$—, —$CH_2$—NH—, and —O—.

The disclosure also relates to compound of formula (A) or (B):

(A)

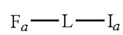

(B)

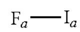

or a pharmaceutically acceptable salt thereof, wherein $F_a$ is a FAPα targeting moiety having a structure represented by the following formula (Y):

(Y)

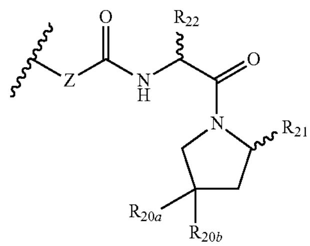

wherein Z can be:

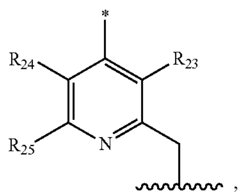

,

-continued

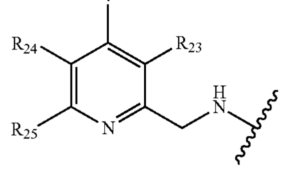

,

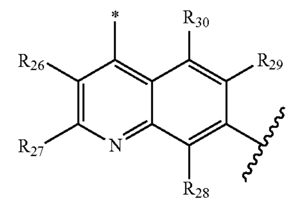

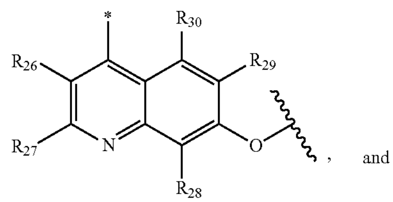

, and

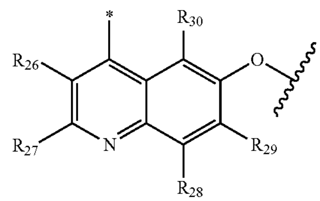

, wherein:

* indicates an attachment point to a carbonyl as shown in formula (Y);

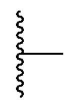

indicates an attachment point to L in formula (A) and IL in formula (B); wherein:

$R_{20a}$ and $R_{20b}$ are the same or different and are each independently selected from the group consisting of hydrogen, halogen, and $C_{1-4}$alkyl;

$R_{21}$ is selected from the group consisting of $C_{1-4}$ alkyl, nitrile, isonitrile, and boronic acid; $R_{22}$ is —$CH_3$;

$R_{23}$ and $R_{24}$ are the same or different, and are each independently selected from the group consisting of hydrogen, halogen, and $C_{1-4}$alkyl;

$R_{25}$ is selected from the group consisting of hydrogen, methoxy, halogen, $CF_3$, and $C_{1-4}$ alkyl;

$R_{26}$ and $R_{27}$ are the same or different, and are each independently selected from the group consisting of hydrogen, halogen, and $C_{1-4}$alkyl; and $R_{28}$, $R_{29}$, and $R_{30}$ are the same or different, and are each independently selected from the group consisting of hydrogen, methoxy, halogen, $CF_3$, and $C_{1-4}$alkyl; and the compound is not

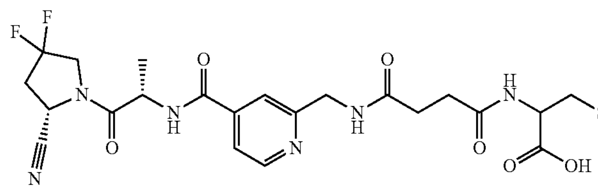
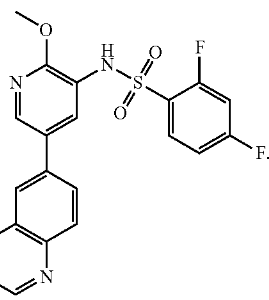

The disclosure also relates to compound of formula (A) or (B):

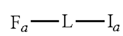
(A)

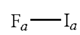
(B)

or a pharmaceutically acceptable salt thereof, wherein $F_a$ is a FAPα targeting moiety selected from F1 and F6:

F1

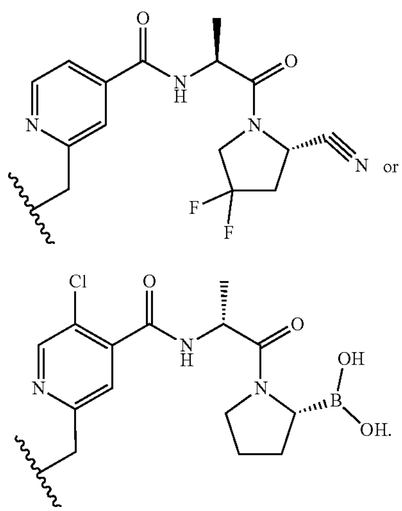
or

F6

In any compounds of Formula (A) or (B), L can be any suitable divalent linker. For example, L can be a non-releasable linker or a releasable linker, as the terms are defined herein, each of which can be attached to the other in any order or combination. In other words, L can have one or more non-releasable portions and one or more releasable portions. Each of these "portions" can be connected through existing or additional heteroatoms on $F_a$ and/or $I_a$ Illustrative heteroatoms through which L can be connected to at least one of $F_a$ and I include nitrogen (e.g., NH or NR, wherein R can be any suitable substituent, including hydrogen, alkyl, heteroalkyl, heterocyclyl, aryl, heteroaryl, arylalkyl, heteroarylalkyl, and the like, each of which can be optionally substituted), oxygen, sulfur (e.g., —S— and SOx, wherein x is 1 or 2) or combinations thereof including —(NHRNHR)—, wherein each R can be the same or different; and —($NHRSO_2$)—.

In some embodiments, the linker is a bivalent linker (e.g., connecting a single $F_a$ to a single $I_a$). In some embodiments, the linker is a multivalent linker (e.g., connecting two or more $F_a$ to a single $I_a$), two or more $I_a$ to a single $F_a$, or two or more $F_a$ to two or more $I_a$). In some embodiments, the linker is a multivalent linker connecting two or more $F_a$ to a single $I_a$. In some embodiments, the linker is a multivalent linker connecting two or more $I_a$ to a single $F_a$. In some embodiments, the linker is a multivalent linker connecting two or more $F_a$ to two or more $I_a$. In some embodiments, the linker is polyvalent and has multiple attachment points for one or more additional chemical groups (e.g., the additional chemical groups comprise one or more additional $F_a$ groups or $I_a$ groups; or the additional chemical groups comprise one or more binding ligands that are not $F_a$ groups or $I_a$ groups). In some embodiments, the linker is a releasable linker. In some embodiments, the linker is a non-releasable linker.

In some embodiments, L is $(L^1)_o$-Y-$(L_2)_p$, wherein:

each $L^1$ is a first linker;

each $L^2$ is a second linker;

Y is a template that connects multiple arms of the compound;

o is an integer from 1-5; and p is an integer from 1-5.

In some embodiments, $L^1$ and $L^2$ are the same. In some embodiments, $L^1$ and $L^2$ are different. In some embodiments, each $L^1$ is connected to an $F_a$ group (and the Y group). In certain embodiments, each $L^2$ is connected to a $I_a$ group (and the Y group). In certain embodiments, 0 and m are the same, such as 1-6, 1-3, or 1. In some embodiments, p is 1. In some embodiments, o is 1. In some embodiments, p and o are each 1.

In some embodiments, each $L^1$ and $L^2$ independently comprise a oligoethylene glycol (chain), a polyethylene glycol (chain), an alkyl (chain), an oligopeptide (chain), or a polypeptide (chain). In some embodiments, each $L^1$ and $L^2$ independently comprise an oligoethylene glycol (chain) or a polyethylene glycol (chain).

In some embodiments, each $L^1$ and $L^2$ independently comprise a triazole or an amide.

In some embodiments, each $L^1$ and $L^2$ independently comprise an oligopeptide (chain) or a polypeptide (chain). In some embodiments, each $L^1$ and $L^2$ independently comprise a peptidoglycan (chain).

In some embodiments, each $L^1$ and $L^2$ independently comprise a oligoproline or a oligopiperidine.

In some embodiments, each $L^1$ and $L^2$ are independently a length from 15-200 angstroms (Å).

In some embodiments, o is an integer from 1-5. In some embodiments, o is an integer from 1-3. In some embodiments, o is 1. In some embodiments, o is m.

In some embodiments, p is an inter from 1-5. In some embodiments, p is an integer from 1-3. In some embodiments, p is 1.

In some embodiments, L comprises at least one linker group, each linker group selected from the group consisting of polyethylene glycol (PEG), alkyl, sugar, and peptide. In some embodiments, the linker is a polyethylene glycol-(PEG-) (e.g., pegylated-), alkyl-, sugar-, and peptide-based dual linker.

In some embodiments, L is a non-releasable linker (e.g., bivalently (e.g., covalently) attached to $I_a$ and $F_a$). In some embodiments, L is a releasable linker (e.g., bivalently (e.g., covalently) attached to $I_a$ and $F_a$.

The linker present in the compounds described herein can be any suitable linker. For example, in some embodiments, the linker is a hydrophilic linker, such as a linker that comprises one or more of an amino acid (which are the same or different), an alkyl chain, a polyethylene glycol (PEG) monomer, a PEG oligomer, a PEG polymer, or a combination of an any of the foregoing, in some embodiments, the linker comprises an oligomer of peptidoglycans, glycans, or anions. In some embodiments, when the linker comprises a chemical group, that group includes one or more of its atoms in the backbone of the linker. In some embodiments, said chemical group is not be required to include atoms in the backbone of L when the group is for binding purposes (such as an albumin binding group), is a glucuronide, or is a "W" group as described herein. For a linker that comprises one or more PEG units, all carbon and oxygen atoms of the PEG units are part of the backbone unless otherwise specified. A cleavable bond for a releasable linker is part of the backbone. The "backbone" of the linker L is the shortest chain of contiguous atoms forming a covalently bonded connection between $F_a$ and $I_a$. In some embodiments, a polyvalent linker has a branched backbone, with each branch serving as a section of backbone linker until reaching a terminus.

The L groups described herein can have any suitable length and chemical composition. For example, L can have a chain length of at least about 7 atoms in length. In one variation, L is at least about 10 atoms in length. In one variation, L is at least about 14 atoms in length. In another variation, L is between about 7 and about 31, between about 7 and about 24, or between about 7 and about 20 atoms in length. In another variation, L is between about 14 and about 31, between about 14 and about 24, or between about 14 and about 20 atoms in length. In another variation, L can have a chain length of at least 7 atoms, at least 14 atoms, at least 20 atoms, at least 25 atoms, at least 30 atoms, at least 40 atoms; or from 1 to 15 atoms, 1 to 5 atoms, 5 to 10 atoms, 5 to 20 atoms, 10 to atoms or 25 to 100 atoms. An example of an L linker group having a chain length of 1 to 5 atoms is a group of the formula:

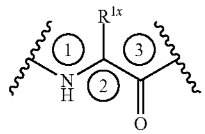

wherein $R^{1x}$ can be H, alkyl, arylalkyl, -alkyl-S-alkyl or arylalkyl or the side-chain of any naturally- or non-naturally occurring amino acid, and the like; and the numbers represent the atoms that are counted as being part of the chain, which is in this case is 3 atoms. Examples of R include H (i.e., glycine), alkyl (e.g., alanine, valine, isoleucine, and leucine), -alkyl-S-alkyl (e.g., methionine), arylalkyl (e.g., phenylalanine, tyrosine, and tryptophan), and the like. The atom to which R is attached can be chiral and can have any suitable relative configuration, such as a D- or L-configuration.

The atoms used in forming L can be combined in all chemically relevant ways, such as chains of carbon atoms forming alkylene groups, chains of carbon and oxygen atoms forming polyoxyalkylene groups, chains of carbon and nitrogen atoms forming polyamines, and others. In addition, it is to be understood that the bonds connecting atoms in the chain can be either saturated or unsaturated, such that for example, alkanes, alkenes, alkynes, cycloalkanes, arylenes, imides, and the like can be divalent radicals that are included in L. In addition, it is to be understood that the atoms forming the linker may also be cyclized upon each other to form saturated or unsaturated divalent cyclic radicals in the linker, such as radicals of the formulae:

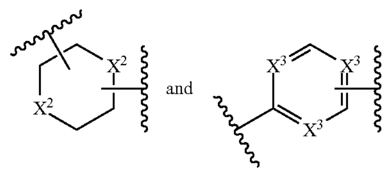

wherein each $X^2$ is independently $CH_2$, N (when there is a bond attached to $X^2$), NH or O and each $X^3$ is independently N, C (when there is a bond attached to $X^3$) or CH. In each of the foregoing and other L groups described herein the chain forming the linker can be substituted or unsubstituted.

Alternatively, or in addition to chain length, L can have any suitable substituents that can affect the hydrophobicity or hydrophilicity of L. Thus, for example, L can have hydrophobic side chain group, such as an alkyl, cycloalkyl, aryl, arylalkyl, or like group, each of which is optionally substituted. If L were to include one or more amino acids, L can contain hydrophobic amino acid side chains, such as one or more amino acid side chains from phenylalanine (Phe) and tyrosine (Tyr), including substituted variants thereof, and analogs and derivatives of such side chains.

L can comprise portions that are neutral under physiological conditions. But L can comprise portions that can be protonated or deprotonated to carry one or more positive or one or more negative charges, respectively. Or L can comprise neutral portions and portions that can be protonated to carry one or more positive charges. Examples of neutral portions include poly hydroxyl groups, such as sugars, carbohydrates, saccharides, inositols, and the like, and/or polyether groups, such as polyoxyalkylene groups including polyoxyethylene, polyoxypropylene, and the like. Examples of portions that can be protonated to carry one or more positive charges include amino groups, such as polyaminoalkylenes including ethylene diamines, propylene diamines, butylene diamines and the like, and/or heterocycles including pyrrolidines, piperidines, piperazines, and other amino groups, each of which can be optionally substituted. Examples of portions that can be deprotonated to carry one or more negative charges include carboxylic acids, such as aspartic acid, glutamic acid, and longer chain carboxylic acid groups, and sulfuric acid esters, such as alkyl esters of sulfuric acid.

Illustrative polyoxyalkylene groups include those of a specific length range from about 4 to about 20 polyoxyalkylene (e.g., polyethylene glycol) groups. Illustrative alkyl sulfuric acid esters may also be introduced with click chemistry directly into the backbone. Illustrative L groups comprising polyamines include L groups comprising EDTA and DTPA radicals:

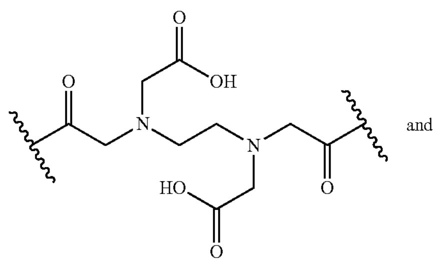

and

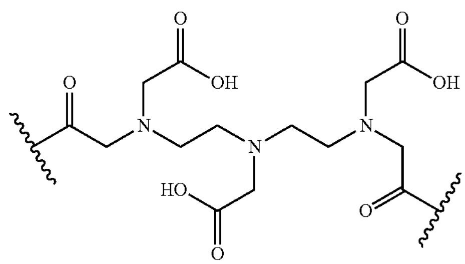

(poly)peptides:

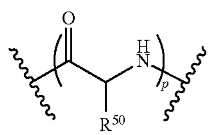

β-amino acids, and the like:

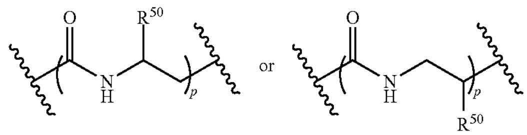

and combinations thereof, wherein each $R^{50}$ is independently H, alkyl, arylalkyl, heterocyclylalkyl, ureido, aminoalkyl, alkylthio or amidoalkyl, such as in the side chains of naturally-occurring amino acids like alanine, valine, leucine, isoleucine, phenylalanine, tyrosine, tryptophan, serine threonine, asparagine, methionine, lysine, arginine, and histidine. Non-naturally occurring amino acids are also contemplated herein.

As discussed herein, L can include at least one releasable portion. In one variation, L includes at least two releasable linkers (e.g. cleavable linkers). The choice of a releasable linker or a non-releasable linker can be made independently for each application or configuration of the compounds described herein. The releasable linkers described herein comprise various atoms, chains of atoms, functional groups, and combinations of functional groups. For example, the releasable linker can comprise about 1 to about 30 atoms, or about 2 to about atoms. Lower molecular weight linkers (i.e., those having an approximate molecular weight of about 30 g/mol to about 1,000 g/mol, such as from about 30 g/mol to about 300 g/mol, about 100 g/mol to about 500 g/mol or about 150 g/mol to about 600 g/mol) are also described. Precursors to such linkers can be selected to have either nucleophilic or electrophilic functional groups, or both, optionally in a protected form with a readily cleavable protecting group to facilitate their use in synthesis of the intermediate species.

The terms "non-releasable linker" or "non-cleavable linker" are used interchangeably. As used herein, they refer to a linker that cannot be cleaved under extracellular physiological conditions (e.g., a pH-labile, acid-labile, oxidatively-labile, or enzyme-labile bond). However, such a linker may include bonds that can be cleaved after entry into a cell The term "releasable linker" as used herein refers to a linker that includes at least one bond that can be broken under physiological conditions (e.g., a pH-labile, acid-labile, oxidatively-labile, or enzyme-labile bond). Releasable groups also include photochemically-cleavable groups. Examples of photochemically-cleavable groups include 2-(2-nitrophenyl)-ethan-2-ol groups, linkers containing o-nitrobenzyl, desyl, trans-o-cinnamoyl, m-nitrophenyl or benzylsulfonyl groups (see, for example, Dorman and Prestwich, Trends Biotech. 18:64-77 (2000); Greene and Wuts, Protective Groups in Organic Synthesis, 2nd ed., John Wiley & Sons, New York (1991); and U.S. Pat. Nos. 5,143,854; 5,986,076; 5,917,016; 5,489,678; 5,405,783).

The cleavable bond or bonds can be present in the interior of a cleavable linker and/or at one or both ends of a cleavable linker. It should be appreciated that such physiological conditions resulting in bond breaking include standard chemical hydrolysis reactions that occur, for example, at physiological pH, or as a result of compartmentalization into a cellular organelle such as an endosome having a lower pH than cytosolic pH. Illustratively, the bivalent linkers described herein can undergo cleavage under other physiological or metabolic conditions, such as by the action of a glutathione mediated mechanism. It is appreciated that the lability of the cleavable bond can be adjusted by including functional groups or fragments within the bivalent linker L that are able to assist or facilitate such bond breakage, also termed anchimeric assistance. The lability of the cleavable bond can also be adjusted by, for example, substitutional changes at or near the cleavable bond, such as including alpha branching adjacent to a cleavable disulfide bond, increasing the hydrophobicity of substituents on silicon in a moiety having a silicon-oxygen bond that can be hydrolyzed, homologating alkoxy groups that form part of a ketal or acetal that can be hydrolyzed, and the like. In addition, it is appreciated that additional functional groups or fragments can be included within the bivalent linker L that are able to assist or facilitate additional fragmentation of the PSMA binding drug linker conjugates after bond breaking of the releasable linker, when present.

In one example, L can comprise one or more releasable linkers that cleave under the conditions described herein by a chemical mechanism involving beta elimination. Such releasable linkers include beta-thio, beta-hydroxy, and beta-amino substituted carboxylic acids and derivatives thereof, such as esters, amides, carbonates, carbamates, and ureas. Such linkers also include 2- and 4-thioarylesters, carbamates, and carbonates.

An example of a releasable linker includes a linker of the formula:

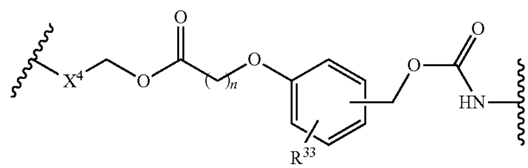

wherein $X^4$ is $NR^{32}$, n is an integer selected from 0, 1, 2, and 3, $R^{32}$ is H or alkyl, $R^{33}$ is hydrogen, or a substituent, including a substituent capable of stabilizing a positive charge inductively or by resonance on the aryl ring, such as alkoxy, and the like. The releasable linker can be further substituted.

Assisted cleavage of releasable portions of L can include mechanisms involving benzylium intermediates, benzyne intermediates, lactone cyclization, oxonium intermediates, beta-elimination, and the like. In addition to fragmentation subsequent to cleavage of a releasable portion of L, the initial cleavage of the releasable linker can be facilitated by an anchimerically assisted mechanism. Thus, in the example of a releasable portion of L given above, the hydroxyalkanoic acid, which may cyclize, facilitates cleavage of the methylene bridge, by for example an oxonium ion, and facilitates bond cleavage or subsequent fragmentation after bond cleavage of the releasable linker. Alternatively, acid catalyzed oxonium ion-assisted cleavage of the methylene bridge can begin a cascade of fragmentation of this illustrative bivalent linker, or fragment thereof. Alternatively, acid-catalyzed hydrolysis of the carbamate may facilitate the beta elimination of the hydroxyalkanoic acid, which may cyclize, and facilitate cleavage of methylene bridge, by for example an oxonium ion. It is appreciated that other chemical mechanisms of bond breakage or cleavage under the metabolic, physiological, or cellular conditions described herein may initiate such a cascade of fragmentation. It is appreciated that other chemical mechanisms of bond breakage or cleavage under the metabolic, physiological, or cellular conditions described herein can initiate such a cascade of fragmentation.

Illustrative mechanisms for cleavage of the bivalent linkers described herein include the following 1,4 and 1,6 fragmentation mechanisms for carbonates and carbamates:

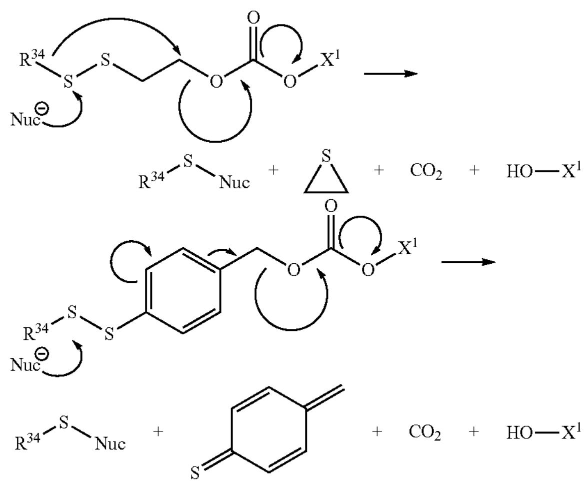

-continued

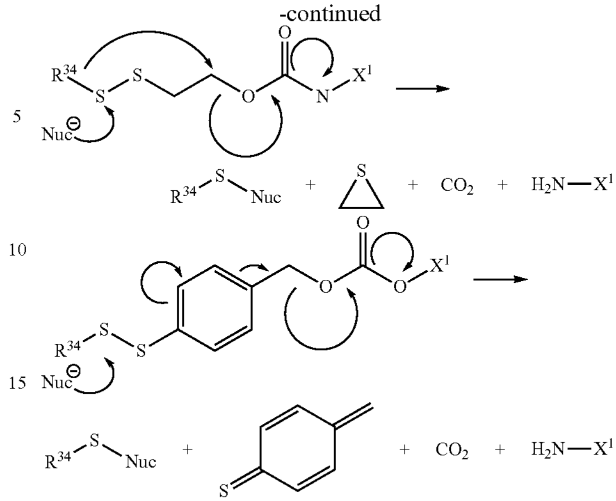

wherein $Nuc^-$ is an exogenous or endogenous nucleophile, glutathione, or bioreducing agent, and the like, and one of $R^{34}$ and $X^1$ is $F_a$ connected through other portions of the bivalent linker, and the other is $I_a$ connected through other portions of the bivalent linker. The location of $R^{34}$ and $X^1$ can be switched such that, e.g., the resulting products are $X^1$—S-Nuc and HO—$R^{34}H_2N$—$R^{34}$.

Although the above fragmentation mechanisms are depicted as concerted mechanisms, any number of discrete steps can take place to effect the ultimate fragmentation of the bivalent linker to the final products shown. For example, the bond cleavage can also occur by acid-catalyzed elimination of the carbamate moiety, which can be anchimerically assisted by the stabilization provided by either the aryl group of the beta sulfur or disulfide illustrated in the above examples. In those variations of this embodiment, the releasable linker is the carbamate moiety. Alternatively, the fragmentation can be initiated by a nucleophilic attack on the disulfide group, causing cleavage to form a thiolate. The thiolate can intermolecularly displace a carbonic acid or carbamic acid moiety and form the corresponding thiocyclopropane. In the case of the benzyl-containing bivalent linkers, following an illustrative breaking of the disulfide bond, the resulting phenyl thiolate can further fragment to release a carbonic acid or carbamic acid moiety by forming a resonance stabilized intermediate. In any of these cases, the releasable nature of the illustrative bivalent linkers described herein can be realized by whatever mechanism can be relevant to the chemical, metabolic, physiological, or biological conditions present.

As described above, therefore, releasable linkers can comprise a disulfide group. Further examples of releasable linkers comprised in L can include divalent radicals comprising alkyleneaziridin-1-yl, alkylenecarbonylaziridin-1-yl, carbonylalkylaziridin-1-yl, alkylenesulfoxylaziridin-1-yl, sulfoxylalkylaziridin-1-yl, sulfonylalkylaziridin-1-yl, or alkylenesulfonylaziridin-1-yl groups, wherein each of the releasable linkers is optionally substituted. Additional examples of releasable linkers comprise can include divalent radicals comprising methylene, 1-alkoxyalkylene, 1-alkoxycycloalkylene, 1-alkoxyalkylenecarbonyl, 1-alkoxycycloalkylenecarbonyl, carbonylarylcarbonyl, carbonyl(carboxyaryl)carbonyl, carbonyl(biscarboxyaryl)carbonyl, haloalkylenecarbonyl, alkylene(dialkylsilyl), alkylene(alkylarylsilyl), alkylene(diarylsilyl), (dialkylsilyl)aryl, (alkylarylsilyl)aryl, (diarylsilyl)aryl, oxycarbonyloxy, oxycarbonyloxyalkyl, sulfonyloxy, oxysulfonylalkyl, iminoalkylidenyl, carbonylalkylideniminyl, iminocycloalkylidenyl, carbonylcycloalkylideniminyl, alkylenethio, alkylenearylthio or carbonylalkylthio groups, wherein each of the releasable linkers can be optionally substituted.

Additional examples of releasable linkers comprised in L can include an oxygen atom and methylene, 1-alkoxyalkylene, 1-alkoxycycloalkylene, 1-alkoxyalkylenecarbonyl or 1-alkoxycycloalkylenecarbonyl groups, wherein each of the releasable linkers can be optionally substituted. Alternatively, the releasable linker can include an oxygen atom and a methylene group, wherein the methylene group can be substituted with an optionally substituted aryl, and the releasable linker can be bonded to the oxygen to form an acetal or ketal. Further, the releasable linker can include an oxygen atom and a sulfonylalkyl group, and the releasable linker can be bonded to the oxygen to form an alkylsulfonate.

Additional examples of releasable linkers comprised in L can include a nitrogen (e.g., —$NR^{32}$—, wherein $R^{32}$ is H or alkyl) and iminoalkylidenyl, carbonylalkylideniminyl, iminocycloalkylidenyl, and carbonylcycloalkylideniminyl groups, wherein each of the releasable linkers can be optionally substituted and the releasable linker can be bonded to the nitrogen to form an hydrazone. In an alternate configuration, the hydrazone can be acylated with a carboxylic acid derivative, an orthoformate derivative, or a carbamoyl derivative to form various acylhydrazone releasable linkers.

Additional examples of releasable linkers comprised in L can include an oxygen atom and alkylene(dialkylsilyl), alkylene(alkylarylsilyl), alkylene(diarylsilyl), (dialkylsilyl)aryl, (alkylarylsilyl)aryl or (diarylsilyl)aryl groups wherein each of the releasable linkers can be optionally substituted and the releasable linker can be bonded to the oxygen to form a silanol.

Additional examples of releasable linkers comprised in L can include two independent nitrogens (e.g., —$NR^{32}$—) and carbonylarylcarbonyl, carbonyl(carboxyaryl)carbonyl, carbonyl(biscarboxyaryl)carbonyl and the releasable linker can be bonded to the heteroatom nitrogen to form an amide, and also bonded to $X^1$ or $R^{34}$ via an amide bond.

Additional examples of releasable linkers comprised in L can include an oxygen atom, a nitrogen (e.g., —$NR^{32}$—), and a carbonylarylcarbonyl, carbonyl(carboxyaryl)carbonyl, carbonyl(biscarboxyaryl)carbonyl, and the releasable linker can form an amide, and also bonded to $X^1$ or $R^{34}$ via an amide bond.

L can comprise an optionally substituted 1-alkylenesuccinimid-3-yl group and a releasable portion comprising methylene, 1-alkoxyalkylene, 1-alkoxycycloalkylene, 1-alkoxyalkylenecarbonyl or 1-alkoxycycloalkylenecarbonyl groups, each of which can be optionally substituted, to form a succinimid-1-ylalkyl acetal or ketal.

L can comprise carbonyl, thionocarbonyl, alkylene, cycloalkylene, alkylenecycloalkyl, alkylenecarbonyl, cycloalkylenecarbonyl, carbonylalkylcarbonyl, 1-alkylenesuccinimid-3-yl, 1-(carbonylalkyl)succinimid-3-yl, alkylenesulfoxyl, sulfonylalkyl, alkylenesulfoxylalkyl, alkylenesulfonylalkyl, carbonyltetrahydro-2H-pyranyl, carbonyltetrahydrofuranyl, 1-(carbonyltetrahydro-2H-pyranyl)succinimid-3-yl or 1-(carbonyltetrahydrofuranyl)succinimid-3-yl, each of which is optionally substituted. In this example, L can further comprise an additional nitrogen (e.g., —$NR^{32}$—) such that L comprises alkylenecarbonyl, cycloalkylenecarbonyl, carbonylalkylcarbonyl or 1-(carbonylalkyl)succinimid-3-yl groups, each of which can be optionally substituted, bonded to the nitrogen to form an amide. Alternatively, L can further comprise a sulfur atom and alkylene or cycloalkylene groups, each of which can be optionally substituted with carboxy, and can be bonded to the sulfur to form a thiol. In yet another example, L comprises a sulfur atom and 1-alkylenesuccinimid-3-yl and 1-(carbonylalkyl)succinimid-3-yl groups bonded to the sulfur to form a succinimid-3-ylthiol.

L can comprise a nitrogen (e.g., —$NR^{32}$—) and a releasable portion comprising alkyleneaziridin-1-yl, carbonylalkylaziridin-1-yl, sulfoxylalkylaziridin-1-yl, or sulfonylalkylaziridin-1-yl, each of which can be optionally substituted. In this L can comprise carbonyl, thionocarbonyl, alkylenecarbonyl, cycloalkylenecarbonyl, carbonylalkylcarbonyl, or 1-(carbonylalkyl)succinimid-3-yl, each of which can be optionally, and bonded to the releasable portion to form an aziridine amide.

Examples of L include alkylene-amino-alkylenecarbonyl, alkylene-thio-(carbonylalkylsuccinimid-3-yl), and the like, as further illustrated by the following formulae:

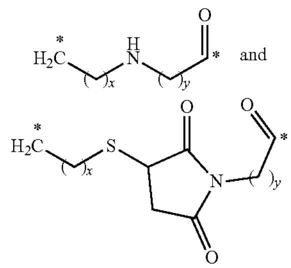

and wherein x and y are each independently 1, 2, 3, 4, or 5.

L can have any suitable assortment of atoms in the chain, including C (e.g., —$CH_2$—, C(O)), N (e.g., NH, $NR^{35}$, wherein $R^{35}$ is, e.g., H, alkyl, alkylaryl, and the like), O (e.g., —O—), P (e.g., —O—P(O)(OH)O—), and S (e.g., —S—). For example, the atoms used in forming L can be combined in all chemically relevant ways, such as chains of carbon atoms forming alkyl groups, chains of carbon and oxygen atoms forming polyoxyalkyl groups, chains of carbon and nitrogen atoms forming polyamines, and others, including rings, such as those that form aryl and heterocyclyl groups (e.g., triazoles, oxazoles, and the like). In addition, the bonds connecting atoms in the chain in L can be either saturated or unsaturated, such that for example, alkanes, alkenes, alkynes, cycloalkanes, arylenes, imides, and the like can be divalent radicals that are included in L. Further, the chain forming L can be substituted or unsubstituted.

Additional examples of L include L groups that include the groups 1-alkylsuccinimid-3-yl, carbonyl, thionocarbonyl, alkyl, cycloalkyl, alkylcycloalkyl, alkylcarbonyl, cycloalkylcarbonyl, carbonylalkylcarbonyl, 1-alkylsuccinimid-3-yl, 1-(carbonylalkyl)succinimid-3-yl, alkylsulfoxyl, sulfonylalkyl, alkylsulfoxylalkyl, alkylsulfonylalkyl, carbonyltetrahydro-2H-pyranyl, carbonyltetrahydrofuranyl, 1-(carbonyltetrahydro-2H-pyranyl)succinimid-3-yl, and 1-(carbonyltetrahydrofuranyl)succinimid-3-yl, wherein each group can be substituted or unsubstituted. Any of the aforementioned groups can be L or can be included as a portion of L. In some instances, any of the aforementioned groups can be used in combination (or more than once) (e.g., -alkyl-C(O)-alkyl) and can further comprise an additional nitrogen (e.g., alkyl-C(O)—NH—, —NH-alkyl-C(O)— or —NH-alkyl-), oxygen (e.g., -alkyl-O-alkyl-) or sulfur (e.g., -alkyl-S-alkyl-). Examples of such L groups are alkylcarbonyl, cycloalkylcarbonyl, carbonylalkylcarbonyl, 1-(carbonylalkyl)succinimid-3-yl, and succinimid-3-ylthiol, wherein each group can be substituted or unsubstituted.

In some instances, L can be formed via click chemistry/click chemistry-derived. For example, L can be derived from copper-catalyzed azide-alkyne cycloaddition (CuAAC), strain promoted azide-alkyne cycloaddition (SPAAC), inverse electron demand Diels-Alder reaction (IEDDA), and Staudinger ligation (SL). For example, A can comprise an azide group and $X^1$ or $R^{36}$ can comprise an alkyne moiety, such that $X^1$ and $R^{36}$ can be linked to each other as shown in Schemes 1-6:

Scheme 1

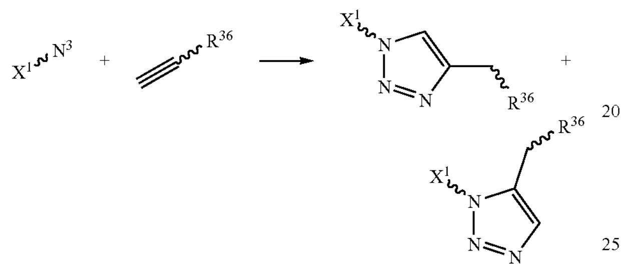

Scheme 2

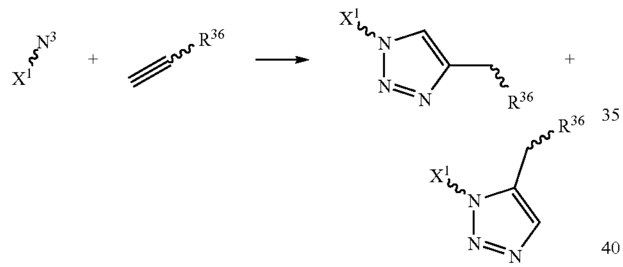

Scheme 3

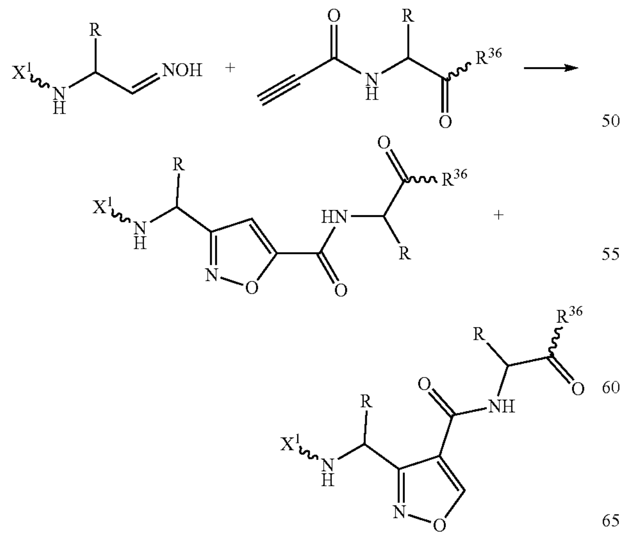

Scheme 4

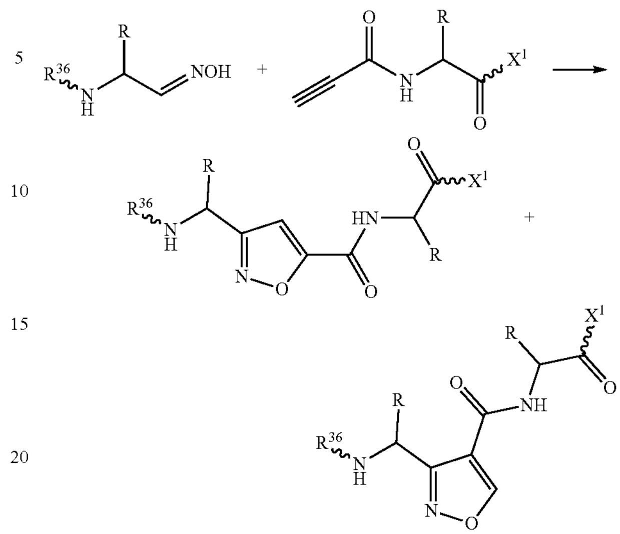

Scheme 5

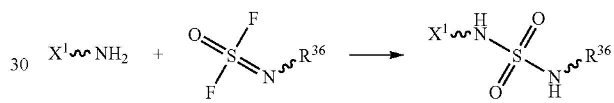

Scheme 6

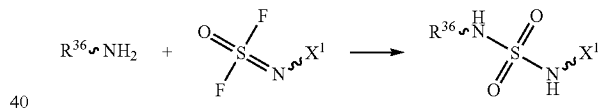

wherein each R is independently H, alkyl, arylalkyl, -alkyl-S-alkyl or arylalkyl or the side-chain of any naturally- or non-naturally-occurring amino acid and the like. In Schemes 1-6, the wavy line connected to $X^1$ and $R^{36}$ represents a linkage between $X^1$ and $R^{36}$ and the groups to which they are attached. One of $R^{36}$ and $X^1$ is $F_a$ connected through other portions of the bivalent linker, and the other is $I_a$ connected through other portions of the bivalent linker. It should be appreciated that in Schemes 1-6, the triazole, oxazole, and the —NH—$SO_2$—NH— group would be considered to be part of L and part of the groups $L^2$-$L^4$ described herein if those groups are click chemistry-derived.

L can be a linker selected from the group consisting of pegylated-, alkyl-, sugar-, and peptide-based dual linker; L is either a non-releasable linker or a releasable linker bivalently covalently attached to the inhibitor I and the FAPα binding ligand F.

For example, L can be

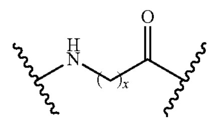,

-continued

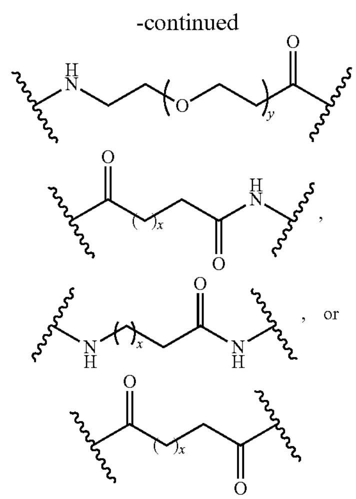

wherein x is an integer from 0 to 10 and y is an integer from 3 to 100.

The linker L can be

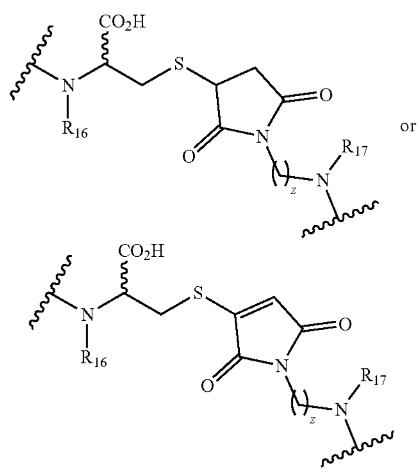

wherein each of $R_{16}$ and $R_{17}$ is independently H or $C_{1-6}$alkyl; and z is an integer from 1 to 8.

For example, L can be

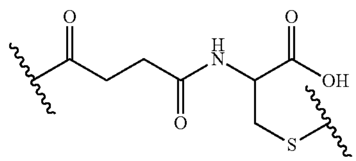

L can be

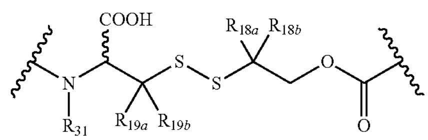

wherein $R_{18a}$, $R_{18b}$, $R_{19a}$, and $R_{19b}$ are independently H or $C_{1-6}$alkyl; and $R_{31}$ is H or $C_1$.

In some embodiments, the compounds described herein include L groups where the IL group is attached to L via an ester, phosphate, oxime, acetal, pyrophosphate, polyphosphate, disulfide, sulfate, hydrazide, imine, carbonate, carbamate or enzyme-cleavable amino acid sequence, or a combination thereof.

In some embodiments, L comprises one or more spacer linkers. In some embodiments, spacer linkers are hydrophilic spacer linkers comprising a plurality of hydroxyl functional groups. A spacer "L" can comprise any stable arrangement of atoms. A spacer comprises one or more L'. Each L' is independently selected from the group consisting an amide, ester, urea, carbonate, carbamate, disulfide, amino acid, amine, ether, alkyl, alkene, alkyne, heteroalkyl (e.g., polyethylene glycol), cycloalkyl, aryl, heterocycloalkyl, heteroaryl, carbohydrate, glycan, peptidoglycan, polypeptide, or any combination thereof. In some embodiments, a spacer comprises any one or more of the following units: an amide, ester, urea, carbonate, carbamate, disulfide, amino acid, amine, ether, alkyl, alkene, alkyne, heteroalkyl (e.g., PEG), cycloalkyl, aryl, heterocycloalkyl, heteroaryl, carbohydrate, glycan, peptidoglycan, polypeptide, or any combination thereof. In some embodiments, a spacer L or L' comprises a solubility enhancer or PK/PD modulator W as described herein. In some embodiments, a spacer comprises a glycosylated amino acid. In some embodiments, a spacer comprises one or more monosaccharide, disaccharide, polysaccharide, glycan, or peptidoglycan. In some embodiments, a spacer comprises a releasable moiety (e.g., a disulfide bond, an ester, or other moieties that can be cleaved in vivo). In some embodiments, a spacer comprises one or more units such as ethylene (e.g., polyethylene), ethylene glycol (e.g., PEG), ethanolamine, ethylenediamine, and the like (e.g., propylene glycol, propanolamine, propylenediamine). In some embodiments, a spacer comprises an oligoethylene, PEG, alkyl chain, oligopeptide, polypeptide, rigid functionality, peptidoglycan, oligoproline, oligopiperidine, or any combination thereof. In some embodiments, a spacer comprises an oligoethylene glycol or a PEG. In some embodiments, a spacer comprises an oligoethylene glycol. In some embodiments, a spacer comprises a PEG. In some embodiments, a spacer comprises an oligopeptide or polypeptide.

In some embodiments, a spacer comprises an oligopeptide. In some embodiments, a spacer comprises a polypeptide. In some embodiments, a spacer comprises a peptidoglycan. In some embodiments, a spacer does not comprise a glycan. In some embodiments, a spacer does not comprise a sugar. In some embodiments, a rigid functionality is an oligoproline or oligopiperidine. In some embodiments, a rigid functionality is an oligoproline. In some embodiments, a rigid functionality is an oligopiperidine. In some embodiments, a rigid functionality is an oligophenyl. In some embodiments, a rigid functionality is an oligoalkyne. In some embodiments, an oligoproline or oligopiperidine has about two up to and including about fifty, about two to about forty, about two to about thirty, about two to about twenty, about two to about fifteen, about two to about ten, or about two to about six repeating units (e.g., prolines or piperidines).

In some embodiments, a compound disclosed herein further comprises a W group to improve properties of the compound. In some embodiments, linkers can be multivalent and can contain more than one $F_a$ and/or more than one $I_a$ groups, as described herein. In some embodiments, one or more $F_a$ are replaced with W, provided that one or more $F_a$ are not W. In some embodiments, one or more $F_a$ are replaced with W, provided that one or more $F_a$ are moieties targeting FAPα. In some embodiments, the linker L comprises one or more W groups. In some embodiments, W comprises a solubility enhancer or PK/PD modulator. In some embodiments, W comprises polyethylene glycol (PEG), sugar, peptide, or peptidoglycan. In some embodiments, W comprises a PEG, sugar, peptide, or peptidoglycan for achieving better solubility and PK/PD properties. In some embodiments, W comprises one or more monosaccharide, disaccharide, peptide, peptidoglycan, and/or serum albumin. In some embodiments, W comprises one or more PEG, peptide, peptidoglycan, or serum albumin. In some embodiments, W does not comprise a sugar. In some embodiments, W does not comprise a monosaccharide, disaccharide, or polysaccharide. In some embodiments, W does not comprise a glycan. In some embodiments, W comprises a glycosylated amino acid. In some embodiments, W comprises a glycosylate cysteine. In some embodiments, W comprises a free carboxylic acid. In some embodiments, W comprises a PEG.

In some embodiments, W comprises one or more monosaccharide, disaccharide, oligosaccharide, polysaccharide, peptide, peptidoglycan, serum albumin, solubility enhancer, PK/PD modulator, or a combination thereof. In some embodiments, W modulates a pharmacological, pharmacokinetic, pharmacodynamic, or physicochemical property. In some embodiments, W facilitates internalization. In some embodiments, W improves aqueous solubility. In some embodiments, W increases plasma protein binding. In some embodiments, W modulates (e.g., reduces) the compound's excretion, elimination, metabolism, stability (e.g., enzymatic stability, plasma stability), distribution, toxicity, or a combination thereof.

In some embodiments, a monosaccharide such as found in W exists in an equilibrium between its linear and cyclic form. In some embodiments, the monosaccharide is linear. In some embodiments, the monosaccharide is cyclic. In some embodiments, the monosaccharide exists as a D isomer. In some embodiments, the monosaccharide exists as an L isomer. As non-limiting examples, in some embodiments, W comprises one or more monosaccharides selected from the following: ribose, galactose, mannose, glucose, fructose, N-acetylglucosamine, N-acetylmuramic acid or derivatives thereof (e.g., cyclic or linear forms, methylated derivatives, acetylated derivatives, phosphorylated derivatives, aminated derivatives, oxidized or reduced derivatives, D or L isomers, isotopes, stereoisomers, regioisomers, tautomers, or combinations thereof).

In some embodiments, a disaccharide, oligosaccharide, or polysaccharide, as may be disposed within W, contains an O-linkage, an N-linkage, a C-linkage, or a combination thereof. In some embodiments, the disaccharide, oligosaccharide, or polysaccharide contains a glycosidic linkage in either an alpha- or beta-orientation. In some embodiments, W comprises an oligosaccharide, a polysaccharide, or a glycan (e.g., a glycoprotein, glycopeptide, glycolipid, glycogen, proteoglycan, peptidoglycan, and the like).

In some embodiments, W comprises an amino acid, a peptide, a polypeptide, or a protein. In some embodiments, the amino acid is a natural amino acid (e.g., alanine (Ala), arginine (Arg), asparagine (Asn), aspartic acid (Asp), cysteine (Cys), glutamic acid (Glu), glutamine (Gln), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr), and valine (Val)). Alternatively, in some embodiments, the amino acid is an unnatural or modified amino acid. In some embodiments, W comprises a sugar or sugar derivative covalently attached to the side chain of an amino acid (e.g., a glutamic acid, an aspartic acid).

In some embodiments, W comprises a glycosylated amino acid such as:

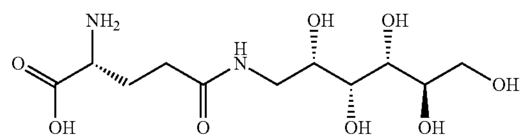 [SMILES: N[C@H](CCC(=O)NC[C@H](O)[C@@H](O)[C@H](O)[C@H](O)CO)C(=O)O]

In some embodiments, W is a peptide or polypeptide and comprises a plurality of amino acids, natural and/or unnatural. In some embodiments, W is a peptide (or peptidoglycan) and has between two and twenty amino acids.

In some embodiments, an amino acid, a peptide, a polypeptide, or a protein disposed within or making up W has a pharmacological or physicochemical effect that enhances one or more properties of the compound (e.g., modulating solubility, solubility, size, permeability, protein binding, target binding, excretion, metabolism, toxicity, distribution, half-life, and/or duration of action). In some embodiments, W is a pharmacokinetic modulator. In some embodiments, the pharmacokinetic modulator is a peptide or protein that can modulate (e.g., enhance) protein binding. In some embodiments, the pharmacokinetic modulator enhances plasma protein binding. In some embodiments, the pharmacokinetic modulator reduces the rate of elimination, excretion, or metabolism. In some embodiments, the pharmacokinetic modulator increases the duration of action of the compound.

In some embodiments, L comprises an albumin ligand. In some embodiments, the albumin ligand comprises

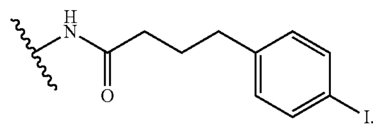 [SMILES: *NC(=O)CCCc1ccc(I)cc1]

The compound of formula (A) or (B) can be: or.

The compound of Formula (A) or (B) can be
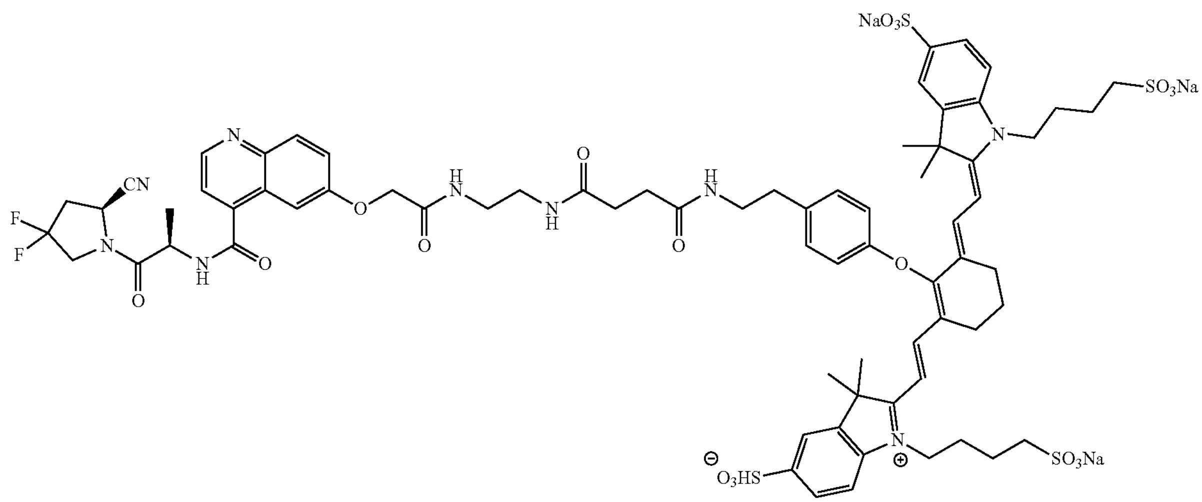
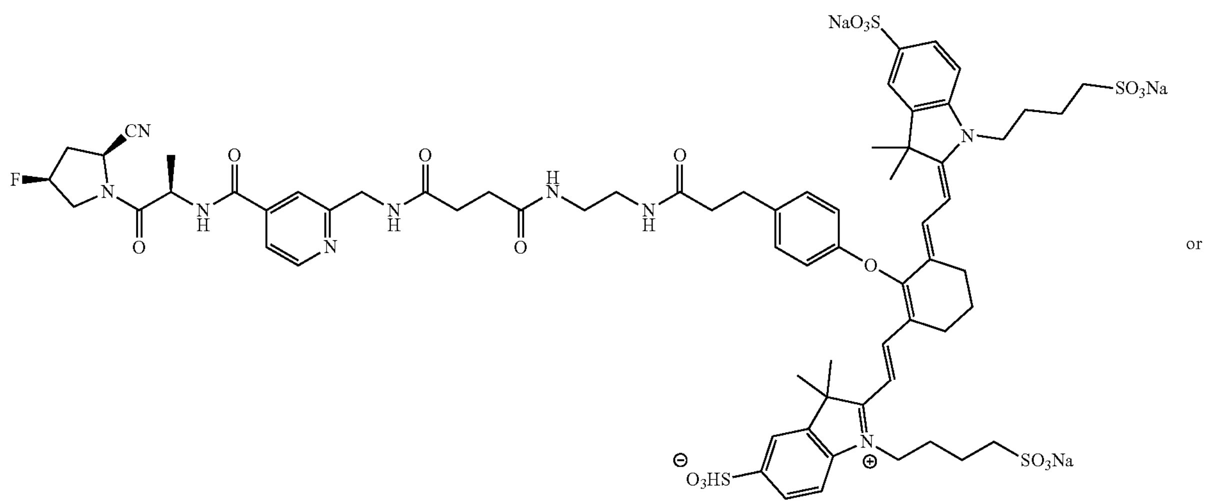
or
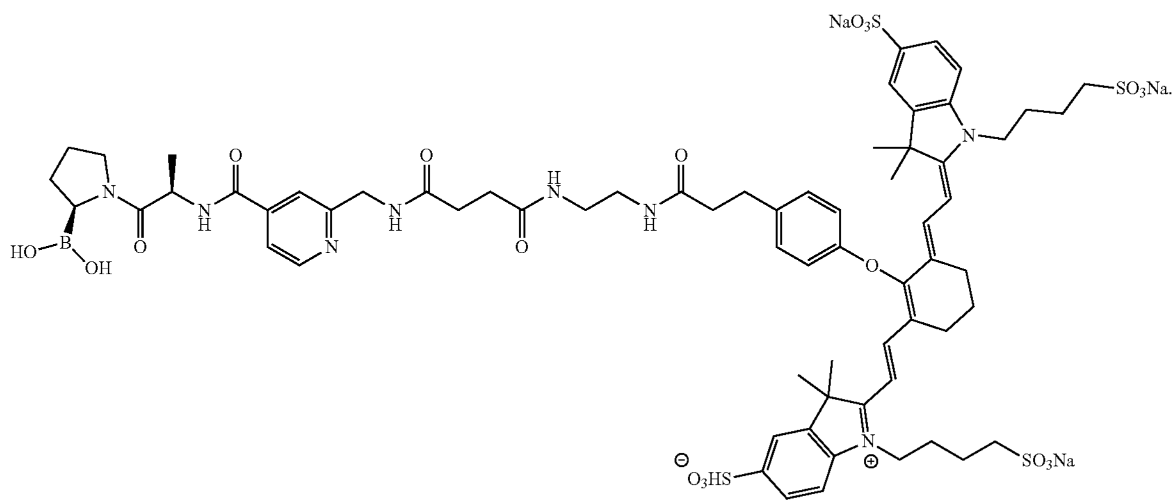

Multivalent Compounds

The disclosure also relates to multivalent compounds having the following formula:

Formula (II)

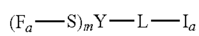

wherein:

- $F_a$ is a FAPα targeting moiety with a molecular weight below 10,000 Daltons;
- S is a spacer (e.g., having a length for the arms of the multivalent targeting ligand (e.g., drug) to reach multiple adjacent FAPα receptors on a target cell);
- Y is a template that connects multiple arms of the compound;
- L is a (e.g., bi-functionalized) linker connecting $F_a$ to $I_a$ (e.g., through a first covalent bond connecting L to $F_a$ and a second covalent bond linking L to $I_a$); and
- $I_a$ is an inhibitor of a signaling pathway necessary for fibrosis in cancer-associated fibroblasts (CAFs); and
- m is 2-6.

In some embodiments, the spacer is the optimal length for the arms of the multivalent drug to reach to multiple adjacent FAPα receptors on a target cell.

In some embodiments, S comprises an oligoethylene, a polyethyleneglycol, an alkyl chain, an oligopeptide or a polypeptide. In some embodiments, S is an oligoethylene glycol or a polyethylene glycol In some embodiments, S is an oligopeptide or polypeptide.

In embodiments, S is a peptidoglycan.

In some embodiments, the spacer is a rigid linker. In some embodiments, S is a rigid linker, such as, for example, an oligoproline or an oligopiperidine In some embodiments, S is a length of at least 15 angstroms (Å).

In some embodiments, S is a length of at most 200 angstroms (Å). In some embodiments, S is a length from 15-200 angstroms (Å).

In some embodiments, Y is a template that connects multiple arms of the compound. In some embodiments, Y has a repeating structure. In some embodiments, Y comprises a releasable bond. In some embodiments, L comprises a disulfide bond. In some embodiments, Y comprises at least one citric acid group (or a radical thereof). In some embodiments, Y comprises one or more triazole. In some embodiments, Y comprises one or more amine. In some embodiments, Y comprises one or more amide. In some embodiments, Y has an aromatic core (e.g., an aryl core or a heteroaryl core). In some embodiments, Y has an alkyl (ene) core. In some embodiments, Y has an amine core. In some embodiments, Y is $N(L^1)_3$ (e.g., wherein $L^1$ is described elsewhere herein). In some embodiments, Y is phenyl substituted with three $L^1$ (e.g., wherein $L^1$ is described elsewhere herein). In some embodiments, Y is $C(L^1)_4$ (e.g., wherein $L^1$ is described elsewhere herein).

In some embodiments, Y is attached to a single $L^1$. In some embodiments, Y is attached to a single $L^2$. In some embodiments, Y is attached to a single $L^1$ and a single $L^2$. In some embodiments, Y is independently connected to each $L^1$ and $L^2$ by an amide bond. In some embodiments, Y is attached to L.

In some embodiments, Y is a template (e.g., a multivalent template) that connects multiple arms of the compound. In some embodiments, Y has a repeating structure. In some embodiments, Y comprises at least one citric acid group (or a radical thereof). In some embodiments, the template has the following structure:

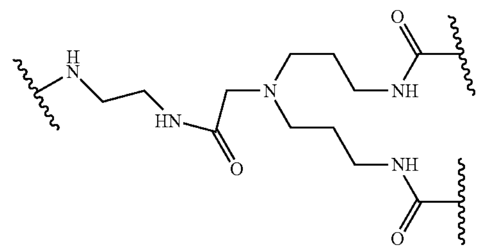

In some embodiments. Y is a template (e.g., a multivalent template) that connects multiple arms of the compound and comprises a template (e.g., a repeating unit) of the following structure:

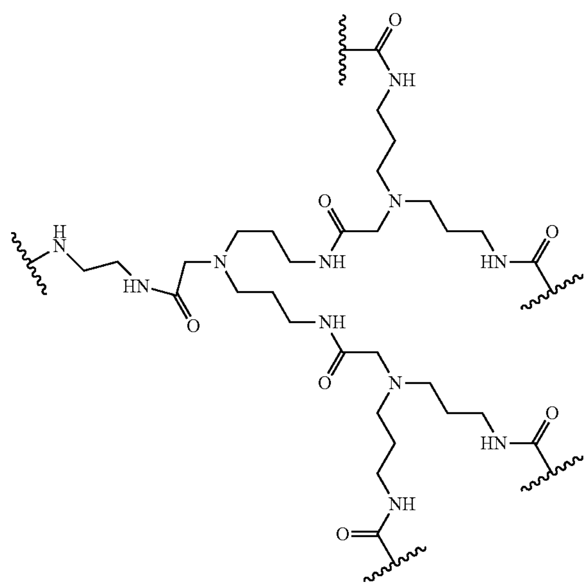

In some embodiments, Y is a template that connects multiple arms of the compound that has a citric acid-based template. In some embodiments, Y is a template (e.g., a multivalent template) that connects multiple arms of the compound and has a (e.g., citric acid-based) template of the following structure:

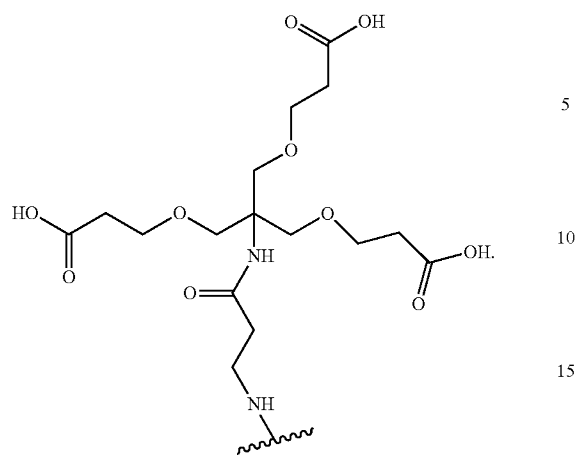
In some embodiments, Y is a template (e.g., a multivalent template) that connects multiple arms of the compound and has a (e.g., citric acid-based) template of the following structure:
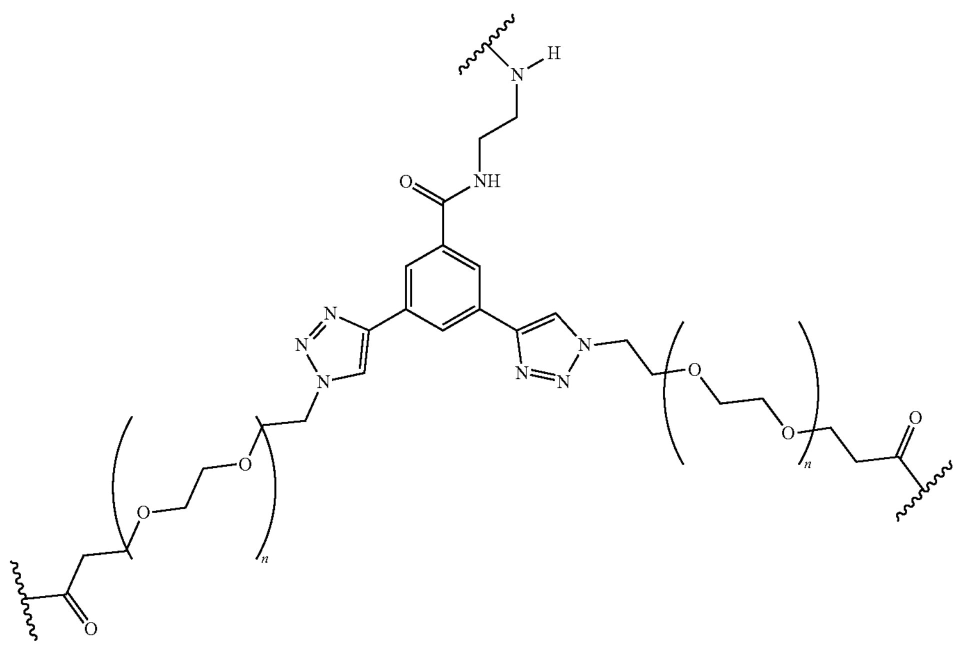
n = 1 to 20

In some embodiments, Y is a template (e.g., a multivalent template) that connects multiple arms of the compound and has a (e.g., citric acid-based) template of the following structure:

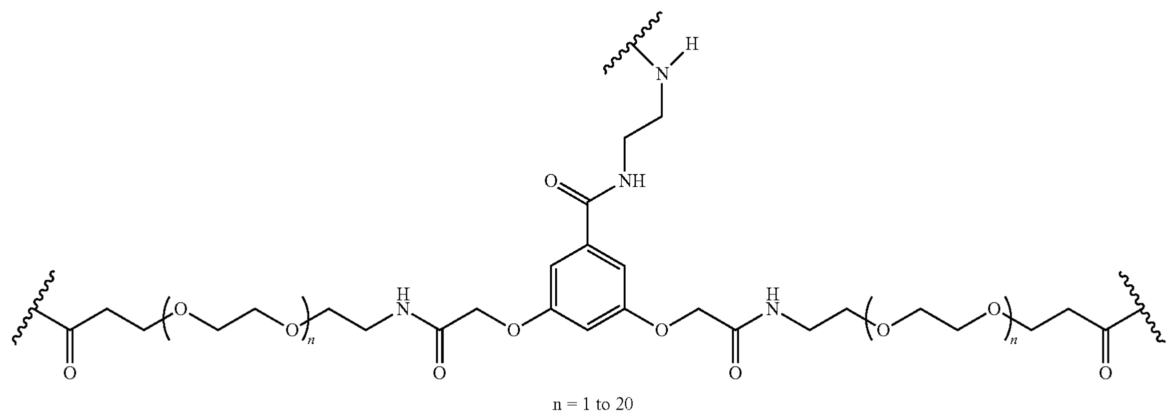

n = 1 to 20

In some embodiments, the compound is (a radical of) a FAPα targeting moiety attached to a linker comprising one or more linker groups, each linker group selected from alkyl, pegylated, and peptidoglycan, wherein the linker is further attached to an inhibitor of a signaling pathway necessary for fibrosis in CAFs described herein.

In any compounds of Formula (A) or (B), $I_a$ can be an inhibitor of a signaling pathway necessary for fibrosis in CAFs. The inhibitor $I_a$ can be a PI-3 kinase inhibitor, a TGFβ/Smad inhibitor, or a Wnt/β-catenin inhibitor.

The inhibitor $I_a$ can be a kinase inhibitor for VEGFR1, VEGFR2, VEGFR3, FGFR1, FGFR2, or PDGFR.

The inhibitor $I_a$ can be a kinase inhibitor for Focal adhesion kinase (FAK) or Rho kinase inhibitor (ROCK).

This disclosure further provides the PI-3 Kinase inhibitor:

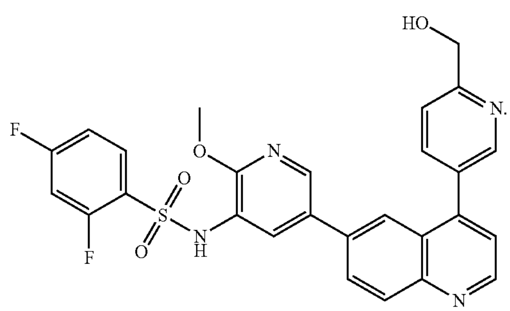 [SMILES: COc1ncc(-c2ccc3nccc(-c4ccc(CO)nc4)c3c2)cc1NS(=O)(=O)c1ccc(F)cc1F]

$I_a$ can be a radical:

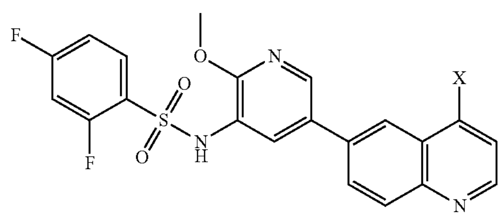

wherein X is selected from the group consisting of

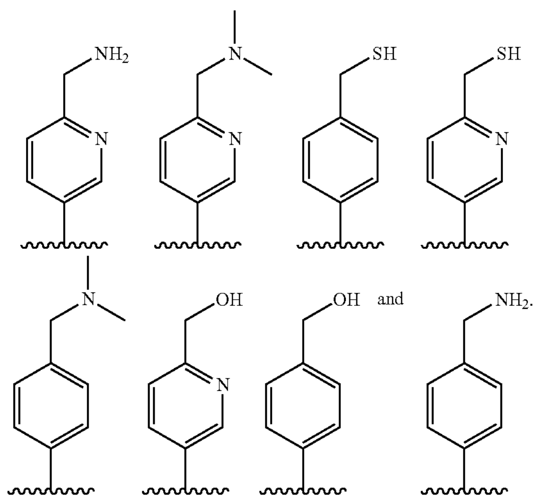

$I_a$ can be a compound according to:

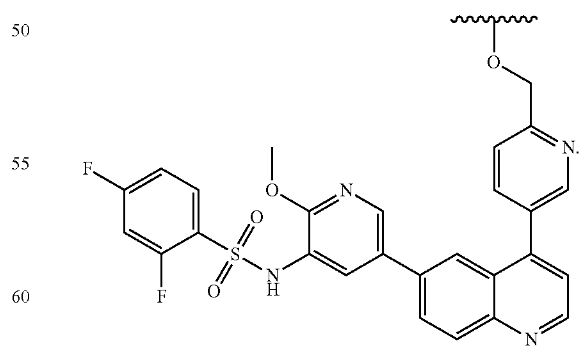

The FAPα binding ligand F has a binding affinity to FAPα in the range between about 1 nM and 25 nM.

Compounds of formula (A) or (B) can include an antifibrotic agent which can be therapeutically effective against cancer cells and/or cancer associated fibroblasts (CAFs). Antifibrotic agents can include, for example, nintedanib and pirfenidone. The antifibrotic agent used in accordance with the present teachings can be any molecule capable of modulating or otherwise modifying pro-fibrotic activity and/or pro-metastasis functions, including pharmaceutically active compound (e.g. inhibitors).

Pharmaceutical Compositions, Routes of Administration, and Dosing

The disclosure relates to pharmaceutical compositions comprising a compound of formula (A) or (B) and a pharmaceutically acceptable excipient.

Excipients are substances added to a pharmaceutical formulation which are not active ingredients. The class of excipients includes diluents (e.g., fillers used to, among other things, increase weight and improve content uniformity in tablets, including starches, hydrolyzed starches, partially pregelatinized starches; other examples of diluents include anhydrous lactose, lactose monohydrate, and sugar alcohols such as sorbitol, xylitol and mannitol). Such compositions may be specifically formulated for administration via one or more of a number of routes including, but not limited to, buccal, cutaneous, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. In addition, administration can be by means of capsule, drops, foams, gel, gum, injection, liquid, patch, pill, porous pouch, powder, tablet, or other suitable means of administration.

Also contemplated herein are pharmaceutical compositions comprising any compound described herein and at least one pharmaceutically acceptable excipient that is part of a nanoparticle, a liposomal or an exosomal formulation.

Pharmaceutically acceptable salts of a compound of formula (A) or (B) in accordance with the present teachings are provided. Pharmaceutically acceptable salts of compounds of formula (A) or (B) in accordance with the present teachings include acid addition and base salts thereof.

Suitable acid addition salts are formed from acids which form non-toxic salts. Illustrative examples include but are not limited to the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotionate, nitrate, orotate, oxalate, palmitate, pamoate, phosphate/hydrogen phosphate/dihydrogen phosphate, saccharate, stearate, succinate, tartrate, tosylate, and trifluoroacetate salts.

Suitable base salts of compounds of formula (A) or (B) are formed from bases which form non-toxic salts. Illustrative examples include but are not limited to the arginine, benzathine, calcium, choline, diethylamine, diolamine, glycine, lysine, magnesium, meglumine, olamine, potassium, sodium tromethamine and zinc salts. Hemisalts of acids and bases may also be formed, for example, hemisulphate, and hemicalcium salts.

A compound of formula (A) or (B) can be administered as a formulation in association with one or more pharmaceutically acceptable excipients. Pharmaceutical excipients generally do not provide any pharmacological activity to the formulation, though they provide chemical and/or biological stability, and release characteristics. Examples of suitable formulations can be found, for example, in Remington, The Science And Practice of Pharmacy, 20th Edition, (Gennaro, A. R., Chief Editor), Philadelphia College of Pharmacy and Science, 2000, which is incorporated by reference in its entirety.

The choice of excipients may depend on factors such as the particular mode of administration, the effect of the excipient on solubility and stability, and the nature of the dosage form. Pharmaceutical compositions suitable for the delivery of compounds of formula (A) or (B) and methods for their preparation will be readily apparent to those skilled in the art. Such compositions and methods for their preparation can be found, for example, in Remington: *The Science & Practice of Pharmacy, 21th Edition* (Lippincott Williams & Wilkins, 2005).

A pharmaceutically acceptable excipient includes any and all solvents, dispersion media, coatings, antibacterial and antifungal agents, isotonic and absorption delaying agents, and the like, and combinations thereof, that are physiologically compatible. The excipient can be suitable for parenteral administration. Pharmaceutically acceptable excipients include sterile aqueous solutions or dispersions and sterile powders for the extemporaneous preparation of sterile injectable solutions or dispersions. Supplementary active compounds may also be incorporated into compositions of the disclosure.

Liquid formulations may include suspensions and solutions, Such formulations may comprise an excipient, for example, water, ethanol, polyethylene glycol, propylene glycol, methylcellulose, or a suitable oil, and one or more emulsifying agents and/or suspending agents Liquid formulations may also be prepared by the reconstitution of a solid.

An aqueous suspension may contain the active materials in admixture with appropriate excipients. Such excipients are suspending agents, for example, sodium carboxymethylcellulose, methylcellulose, hydroxypropylmethylcellulose, sodium, alginate, polyvinylpyrrolidone, gum tragacanth and gum acacia; dispersing or wetting agents which can be a naturally-occurring phosphatide, for example, lecithin; a condensation product of an alkylene oxide with a fatty acid, for example, polyoxyethylene stearate; a condensation product of ethylene oxide with a long chain aliphatic alcohol, for example, heptadecaethyleneoxcycetanol; a condensation product of ethylene oxide with a partial ester derived from fatty acids and a hexitol such as polyoxyethylene sorbitol monooleate; or a condensation product of ethylene oxide with a partial ester derived from fatty acids and hexitol anhydrides, for example, polyoxyethylene sorbitan monooleate. The aqueous suspensions can also contain one or more preservatives, for example ascorbic acid, ethyl, n-propyl, or p-hydroxybenzoate; or one or more coloring agents.

Dispersible powders and granules suitable for preparation of an aqueous suspension by the addition of water provide the active ingredient in admixture with a dispersing or wetting agent, suspending agent and one or more preservatives. Additional excipients, for example, coloring agents, can also be present.

Suitable emulsifying agents can be naturally-occurring gums, for example, gum acacia or gum tragacanth; naturally-occurring phosphatides, for example, soybean lecithin; and esters including partial esters derived from fatty acids and hexitol anhydrides, for example, sorbitan mono-oleate, and condensation products of the said partial esters with ethylene oxide, for example, polyoxyethylene sorbitan monooleate. Isotonic agents, for example, sugars, polyalcohols such as mannitol, sorbitol, or sodium chloride can be included in the composition. Prolonged absorption of injectable compositions can be brought about by including in the composition an agent which delays absorption, for example, monostearate salts and gelatin.

Illustrative formats for oral administration include but are not limited to tablets, capsules, elixirs, syrups, and the like.

Depending upon the cancer type as described herein, the route of administration and/or whether a compound of formula (A) or (B) is administered locally or systemically, a wide range of permissible dosages are contemplated herein, including doses falling in the range from about 1 μg/kg to about 1 g/kg. The dosages can be single or divided and can be administered according to a wide variety of protocols, including once a day, twice daily, three times daily, or even every other day, biweekly, once a week, once a month, once a quarter, and the like. In each of these cases it is understood that the therapeutically effective amounts described herein correspond to the instance of administration, or alternatively to the total daily, weekly, month, or quarterly dose, as determined by the dosing protocol.

A compound can be administered directly into the blood stream, into muscle, or into an internal organ. Suitable routes for such parenteral administration include intravenous, intraarterial, intraperitoneal, intrathecal, epidural, intracerebroventricular, intraurethral, intrasternal, intracranial, intratumoral, intramuscular, intranasal, and subcutaneous delivery. Suitable means for parenteral administration include needle (including microneedle) injectors, needle-free injectors and infusion techniques.

Parenteral formulations are typically aqueous solutions which may contain excipients such as salts, carbohydrates, and buffering agents (preferably at a pH of 3-9), but, for some applications, they can be more suitable formulated as a sterile non-aqueous solution or as a dried form to be used in conjunction with a suitable vehicle such as sterile, pyrogen-free water. Any of the liquid formulations described herein can be adapted for parenteral administration of a compound of formula (A) or (B) described herein. The preparation of parenteral formulations under sterile conditions, for example, by lyophilization under sterile conditions, may readily be accomplished using standard pharmaceutical techniques well-known to those skilled in the art. The solubility of a compound used in the preparation of a parenteral formulation can be increased by the use of appropriate formulation techniques, such as the incorporation of solubility-enhancing agents.

Formulations for parenteral administration can be formulated for immediate and/or modified release. Active agents (i.e., compounds of formula (A) or (B) described herein) can be administered in a time-release formulation, for example in a composition which includes a slow-release polymer. The active agents can be prepared with excipients that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PGLA). Methods for the preparation of such formulations are generally known to those skilled in the art. Compounds of formula (A) or (B) or compositions comprising a compound of formula (A) or (B) can be continuously administered, where appropriate.

Sterile injectable solutions can be prepared by incorporating the active agent in the required amount in an appropriate solvent with one or a combination of ingredients described above, as required, followed by filtered sterilization. Typically, dispersions are prepared by incorporating the compound into a sterile vehicle which contains a dispersion medium and any additional ingredients of those described above. In the case of sterile powders for the preparation of sterile injectable solutions, the preferred methods of preparation are vacuum drying and freeze-drying which yields a powder of the active ingredients plus any additional desired ingredient from a previously sterile-filtered solution thereof, or the ingredients can be sterile-filtered together.

The composition can be formulated as a solution, microemulsion, liposome, or other ordered structure suitable to high drug concentration. The excipient can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Any effective regimen for administering a compound of formula (A) or (B) described herein can be used. For example, a compound of formula (A) or (B) described herein can be administered as single doses, or the doses can be divided and administered as a multiple-dose daily regimen. Further, a staggered regimen, for example, one to five days per week can be used as an alternative to daily treatment, and for the purpose of the methods described herein, such intermittent or staggered daily regimen is considered to be equivalent to every day treatment and is contemplated. In some embodiments, the patient is treated with multiple injections of a compound to treat the cancer. In some embodiments, the patient is injected multiple times (e.g. approximately 2-50×) with a conjugate, for example, at 12-72 hour intervals or at 48-72 hour intervals. Additional injections of a compound can be administered to the patient at an interval of days or months after the initial injection(s) and the additional injections may prevent the recurrence of the cancer.

Any suitable course of therapy with a compound of formula (A) or (B) can be used. In some embodiments, individual doses and dosage regimens are selected to provide a total dose administered during a month of about 15 mg. In some examples, a compound can be administered in a single daily dose administered five days per week, in weeks 1, 2, and 3 of each 4-week cycle, with no dose administered in week 4. In an alternative example a compound is administered in a single daily dose administered three days per week, of weeks 1 and 3 of each 4-week cycle, with no dose administered in weeks 2 and 4. In an alternative example, a compound is administered biweekly on weeks 1 and 2 (i.e. on days 1, 4, 8, and 11 of a 3-week cycle). In an alternative example, a compound is administered and once weekly on weeks 1 and 2 (i.e. days 1 and 8 of a 3-week cycle).

The unitary daily dosage of a compound of formula (A) or (B) may vary significantly depending on the patient condition, the cancer being treated, the route of administration of the compound of formula (A) or (B) and tissue distribution, and the possibility of co-usage of other therapeutic treatments, such as radiation therapy or additional drugs in combination therapies. The effective amount to be administered to a patient is based on body surface area, mass, and physician assessment of patient condition. Therapeutically effective doses (also referred to herein as "therapeutically effective amounts") may range, for example from approximately 0.5-20.0 $mg/m^2$.

It is appreciated that compounds of formula (A) or (B) can exist in unsolvated forms as well as solvated forms, including hydrated forms. In general, the solvated forms are equivalent to unsolvated forms and are encompassed within the scope of the present disclosure. Compounds of formula (A) or (B) described herein may exist in multiple crystalline or amorphous forms. In general, all physical forms are equivalent for the uses contemplated and are intended to be within the scope of the claimed invention.

In some embodiments, compositions and/or dosage forms for administration of a compound are prepared from a compound with a purity of at least approximately 90%, or approximately 95%, or approximately 96%, or approximately 97%, or approximately 98%, or approximately 99%, or approximately 99.5%. In other embodiments, compositions and or dosage forms for administration of a compound are prepared from a compound with a purity of at least 90%, or at least 95%, or at least 96%, or at least 97%, or at least 98%, or at least 99%, or at least 99.5%.

Method of Treatment

This disclosure further provides a method of treating a cancer (e.g., a solid tumor) in a subject in need thereof by modulating the profibrotic behavior of CAFs. The disclosure also relates to a method of treating a fibrotic disease or disorder in a subject in need thereof.

The methods can be used for both human clinical medicine and veterinary applications. Thus, a "subject" can be administered a compound of formula (A) or (B) in accordance with the present teachings, and can be human "patient") or, in the case of veterinary applications, can be a laboratory, agricultural, domestic, or wild animal. In some embodiments, the subject can be a human patient, a laboratory animal such as a rodent (e.g. mice, rats, hamsters, etc.), a rabbit, a monkey, a chimpanzee, domestic animals such as dogs, cats, and rabbits, agricultural animals such as cows, horses, pigs, sheep, goats, and wild animals in captivity such as bears, pandas, lions, tigers, leopards, elephants, zebras, giraffes, gorillas, dolphins, and whales.

Any of the methods disclosed herein comprises the steps of providing to the subject a therapeutically effective amount of compound $F_a$-L-$I_a$, wherein $F_a$ is a targeting ligand to FAPα that has a molecular weight below 10,000 Daltons, L is a releasable linker, and $I_a$ is a therapeutic drug that has an inhibitory effect on profibrotic signaling pathways in fibroblasts; in more particular aspects, the inhibitor $I_a$ is a pan PI-3 Kinase inhibitor.

$I_a$ can be

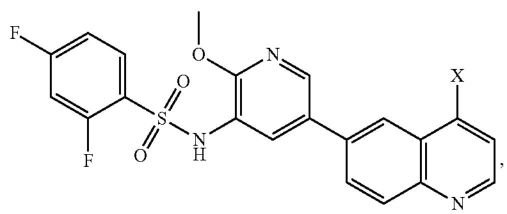

, wherein X is

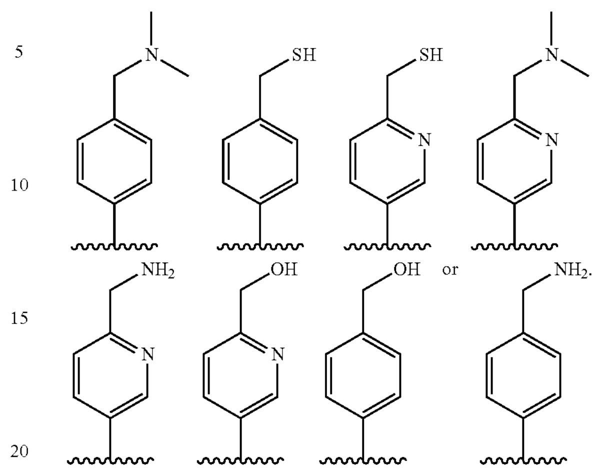

or

.

The cancer described herein can be a cancer cell population that is tumorigenic, including benign tumors and malignant tumors, or the cancer can be non-tumorigenic. The cancer may arise spontaneously or by such processes as mutations present in the germline of the patient or somatic mutations, or the cancer can be chemically-, virally-, or radiation-induced. Cancers applicable to the present teachings include by are not limited to a carcinoma, a sarcoma, a lymphoma, a melanoma, a mesothelioma, a nasopharyngeal carcinoma, a leukemia, an adenocarcinoma, and a myeloma.

The cancer can be selected from the group consisting of lung cancer, bone cancer, pancreatic cancer, skin cancer, cancer of the head, cancer of the neck, cutaneous melanoma, intraocular melanoma, uterine cancer, ovarian cancer, endometrial cancer, leiomyosarcoma, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, small cell lung cancer, cancer of the adrenal gland, sarcoma of soft tissue, cancer of the urethra, cancer of the penis, prostate cancer, chronic leukemia, acute leukemia, lymphocytic lymphomas, pleural mesothelioma, cancer of the bladder, Burkitt's lymphoma, cancer of the ureter, cancer of the kidney, renal cell carcinoma, carcinoma of the renal pelvis, neoplasms of the central nervous system (CNS), primary CNS lymphoma, spinal axis tumors, brain stem glioma, pituitary adenoma, cholangiocarcinoma, Hurthle cell thyroid cancer, and adenocarcinoma of the gastroesophageal junction.

In addition, the agents and methods enable antifibrotic therapy of cancers in which the cancer cells themselves do not express FAPα, but the cancer associated fibroblasts (CAFs) supporting those cancers express FAPα.

The fibrotic disease or disorder can be pulmonary fibrosis (e.g., idiopathic pulmonary fibrosis), liver fibrosis, heart fibrosis, kidney fibrosis, mediastinal fibrosis, retroperitoneal cavity fibrosis, bone marrow fibrosis (aka, myelofibrosis), skin fibrosis, or scleroderma (systemic sclerosis).

The FAPα-targeted antifibrotic compounds of formula (A) or (B) allow for targeted tissue penetration and targeting specificity of FAPα. In addition, the compounds of formula (A) or (B) may rapidly clear from the receptor negative tissues. Since FAPα is expressed in CAFs of most solid tumors, FAPα-targeted antifibrotic agents can be used for targeting the stroma of many types of cancer.

The disclosure also relates to a method of reducing collagen I deposition of activated fibroblasts by administering to a subject in need thereof a compound of formula (A) or (B).

For example, the subject can be a mouse tumor model induced by injecting $5\times10^6$ tumor cells in 0.2 mL of sterile PBS subcutaneously in the right hind flank of a nu/nu female mouse.

For example, the method modulates extracellular matrix production of collagen I.

The disclosure also provides methods for reducing the hydroxyproline production of CAFs.

Kits

In some embodiments, a kit is provided. If a combination of a compound of formula (A) or (B) is to be administered, two or more pharmaceutical compositions can be combined in the form of a kit suitable for sequential administration or co-administration of the compositions. Such a kit may include two or more separate pharmaceutical compositions, at least one of which contains a compound in accordance with the present teachings, and means for separately retaining the compositions, such as a container, divided bottle, or divided foil packet. In some embodiments, compositions comprising one or more compound of formula (A) or (B), in containers having labels that provide instructions for use of the compound of formula (A) or (B) for patient selection and/or treatment are provided.

The components included in kits can be supplied in all manner of containers such that the activities of the different components are substantially preserved, while the components themselves are not substantially adsorbed or altered by the materials of the container. Suitable containers include but are not limited to, ampoules, bottles, test tubes, vials, flasks, syringes, bags, and envelopes (e.g. foil-lined), and the like. The containers can be formed of any suitable material including but not limited to glass, organic polymers (e.g. polycarbonate, polystyrene, polyethylene, polypropylene, etc.), ceramic, metal (e.g. aluminum), metal alloys (e.g. steel), cork, and the like. In addition, the containers can contain one or more access ports (e.g. for access via a needle), such as can be provided by a septum. Preferred materials for septa include rubber and polymers including but not limited to, for example, polytetrafluoroethylene of the type sold under the trade name TEFLON by DuPont (Wilmington, Del.). In addition, the containers may contain two or more compartments separated by partitions or membranes that can be removed to allow mixing of the components.

Kits can also be supplied with other items known in the art and/or which can be desirable from a commercial and user standpoint, including but not limited to instructions for adding the components of the kit to a heat exchange system.

Instructional materials provided with kits can be printed (e.g. on paper) and/or supplied in an electronic-readable medium (e.g. floppy disk, CD-ROM, DVD-ROM, zip disc, videotape, audio tape, etc.). Alternatively, instructions can be provided by directing a user to an Internet web site (e.g. specified by the manufacturer or distributor of the kid) and/or via electronic mail, text message, social media, and/or the like, and combinations thereof.

The entire contents of each and every patent publication, non-patent publication, and reference text cited herein are hereby incorporated by reference, except that in the event of any inconsistent disclosure or definition from the present specification, the disclosure or definition herein shall be deemed to prevail.

Definitions

Unless defined otherwise, all technical and scientific terms used herein have the same meaning as commonly understood by one of skill in the chemical and biological arts. Additionally, as used in this specification and the appended claims, the singular forms "a", "an" and "the" include plural referents unless the content clearly dictates otherwise. Thus, for example, where a compound/composition is substituted with "an" alkyl or aryl, the compound/composition is optionally substituted with at least one alkyl and/or at least one aryl. Furthermore, unless specifically stated otherwise, the term "about" refers to a range of values plus or minus 10% for percentages and plus or minus 1.0 unit for unit values, for example, about 1.0 refers to a range of values from 0.9 to 1.1.

If a chemical group combines several other chemical groups defined herein, then each part of the combination is assumed to be defined as when it is separate, with allowances made to create valences for allowing attachment of the other groups. For example, "alkoxycycloalkylenecarbonyl" radical would be understood to be an alkoxy as defined herein bonded to a cycloalkylene as defined herein, and the cycloalkylene is in turn bonded to a carbonyl group, which is not defined herein but is generally understood to organic chemists, with an open valence on the carbonyl.

The term "alkyl" as used herein refers to substituted or unsubstituted straight chain, branched and cyclic, saturated mono- or bi-valent groups having from 1 to 20 carbon atoms, 10 to 20 carbon atoms, 12 to 18 carbon atoms, 6 to about 10 carbon atoms, 1 to 10 carbons atoms, 1 to 8 carbon atoms, 2 to 8 carbon atoms, 3 to 8 carbon atoms, 4 to 8 carbon atoms, 5 to 8 carbon atoms, 1 to 6 carbon atoms, 2 to 6 carbon atoms, 3 to 6 carbon atoms, or 1 to 3 carbon atoms. Examples of straight chain mono-valent (C1-C20)-alkyl groups include those with from 1 to 8 carbon atoms such as methyl (i.e., $CH_3$), ethyl, n-propyl, n-butyl, n-pentyl, n-hexyl, n-heptyl, n-octyl groups. Examples of branched mono-valent ($C_1$-$C_{20}$)-alkyl groups include isopropyl, iso-butyl, sec-butyl, t-butyl, neopentyl, and isopentyl. Examples of straight chain bi-valent ($C_1$-$C_{20}$)alkyl groups include those with from 1 to 6 carbon atoms such as $—CH_2—$, $—CH_2CH_2—$, $—CH_2CH_2CH_2—$, $—CH_2CH_2CH_2CH_2—$, and $—CH_2CH_2CH_2CH_2CH_2—$. Examples of branched bi-valent alkyl groups include $—CH(CH_3)CH_2—$ and $—CH_2CH(CH_3)CH_2—$. Examples of cyclic alkyl groups include cyclopropyl, cyclobutyl, cyclopently, cyclohexyl, cyclooctyl, bicyclo[1.1.1]pentyl, bicyclo[2.1.1]hexyl, and bicyclo[2.2.1]heptyl. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. In some embodiments, alkyl includes a combination of substituted and unsubstituted alkyl. As an example, alkyl, and also (C1)alkyl, includes methyl and substituted methyl. As a particular example, (C1)alkyl includes benzyl. As a further example, alkyl can include methyl and substituted (C2-C8)alkyl. Alkyl can also include substituted methyl and unsubstituted (C2-C8)alkyl. In some embodiments, alkyl can be methyl and C2-C8 linear alkyl. Alkyl can be methyl and C2-C8 branched alkyl. The term methyl is understood to be $—CH_3$, which is not substituted. The term methylene is understood to be —$CH_2$—, which is not substituted. For comparison, the term (C1)alkyl is understood to be a substituted or an unsubstituted —$CH_3$ or a substituted or an unsubstituted —$CH_2$—. Representative substituted alkyl groups can be substituted one or more times with any of the groups listed herein, for example, cycloalkyl, heterocyclyl, aryl, amino, haloalkyl, hydroxy, cyano, carboxy, nitro, thio, alkoxy, and halogen groups. As further example, representative substituted alkyl groups can be substituted one or more fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino and dialkylamido. Representative substituted alkyl groups can be substituted from a set of groups including amino, hydroxy, cyano, carboxy, nitro, thio and alkoxy, but not including halogen groups. Thus, alkyl can be substituted with a non-halogen group. For example, representative substituted alkyl groups can be substituted with a fluoro group, substituted with a bromo group, substituted with a halogen other than bromo, or substituted with a halogen other than fluoro. Representative substituted alkyl groups can be substituted with one, two, three or more fluoro groups or they can be substituted with one, two, three or more non-fluoro groups. For example, alkyl can be trifluoromethyl, difluoromethyl, or fluoromethyl, or alkyl can be substituted alkyl other than trifluoromethyl, difluoromethyl or fluoromethyl. Alkyl can be haloalkyl or alkyl can be substituted alkyl other than haloalkyl.

"Alkoxy" refers to a radical bonded through an oxygen atom of the formula —O-alkyl, where alkyl is an alkyl chain as defined above.

"Alkylene" or "alkylene chain" generally refers to a straight or branched divalent alkyl group linking the rest of the molecule to a radical group, such as having from one to twelve carbon atoms, for example, methylene, ethylene, propylene, i-propylene, n-butylene, and the like.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene.

"Aralkyl" or "aryl-alkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain.

"Cycloalkyl" refers to a stable 3- to 18-membered non-aromatic ring radical that comprises only carbon atoms as ring atoms. Unless stated otherwise specifically in the specification, the cycloalkyl radical is a monocyclic, bicyclic, tricyclic or tetracyclic ring system, which optionally includes aromatic, fused, and/or bridged ring systems. Examples of such radicals include cyclopropyl, cyclohexyl, norbornyl, and adamantyl. "Cycloalkylene" as used herein specifically refers to a divalent cycloalkyl radical.

The terms "halo," "halogen," or "halide" group, as used herein, by themselves or as part of another substituent, mean, unless otherwise stated, a fluorine, chlorine, bromine, or iodine atom.

"Haloalkyl" refers to an alkyl radical, as defined above, that is substituted by one or more halogen radicals, as defined above, for example, trifluoromethyl, difluoromethyl, fluoromethyl, 2,2,2-trifluoroethyl, 1-fluoromethyl-2-fluoroethyl, and the like.

"Haloalkyl" refers to an alkyl radical, as defined above, that is substituted by one or more halogen radicals, as defined above, for example, trifluoromethyl, difluoromethyl, fluoromethyl, 2,2,2-trifluoroethyl, 1-fluoromethyl-2-fluoroethyl, and the like.

"Heterocyclyl" or "heterocycle" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which optionally includes aromatic, fused, and/or bridged ring systems. The heteroatoms in the heterocyclyl radical are optionally oxidized. The heterocyclyl radical is partially or fully saturated. Disclosures provided herein of an "heterocyclyl" are intended to include independent recitations of heterocyclyl comprising aromatic and non-aromatic ring structures, unless otherwise stated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, 1,3-benzodioxolyl, 1,4-benzodioxanyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, indolinyl, isoindolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, benzofuranyl, benzooxazolyl, benzo[d]thiazolyl, benzothiadiazolyl, benzo[b][1,4]dioxepinyl, benzo[b][1,4]oxazinyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocyclooocta[d]pyridinyl, isothiazolyl, imidazolyl, indazolyl, indolyl, indazolyl, isoindolyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl).

The term "heterocycloalkyl" as used herein refers to alkyl groups as defined herein in which a hydrogen or carbon bond of an alkyl group as defined herein is replaced with a bond to a heterocyclyl group as defined herein. Representative heterocycloalkyl groups include, but are not limited to, furan-2-yl methyl, furan-3-yl methyl, pyridine-3-yl methyl, tetrahydrofuran-2-yl methyl, and indol-2-yl propyl. The term "heterocycloalkylalkyl" as used herein refers to a heterocycloalkyl group attached to an alkyl group, as defined herein.

The term "heteroarylalkyl" as used herein refers to alkyl groups as defined herein in which a hydrogen or carbon bond of an alkyl group is replaced with a bond to a heteroaryl group as defined herein.

The term "amine" as used herein refers to primary, secondary, and tertiary amines having, e.g., the formula $N(group)_3$* wherein each group can independently be H or non-H, such as alkyl, aryl, and the like. Amines include but are not limited to $R—NH_2$, for example, alkylamines, arylamines, alkylarylamines; $R_2NH$ wherein R is defined herein, such as dialkylamines, diarylamines, aralkylamines, heterocyclylamines and the like; and $R_3N$ wherein each R is independently selected, such as trialkylamines, dialkylarylamines, alkyldiarylamines, triarylamines, and the like. The term "amine" also includes ammonium ions as used herein.

The term "amino" as used herein refers to a substituent of the form $—NH_2$, —NHR, $—NR_2$, $—NR_3+$, wherein each R is independently selected, and protonated forms of each, except for $—NR_3+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

An example of a "alkylamino" is —NH-alkyl and $—N(alkyl)_2$.

The term "alkylamido" as used herein refers to a group containing a carbonyl moiety wherein the group is bonded via the carbonyl carbon atom. The carbonyl carbon atom is also bonded to a nitrogen group which is bonded to one or more alkyl groups. In a further case, which is also an alkylamido as the term is defined herein, the carbonyl carbon atom is bonded to an nitrogen atom which is bonded to one or more aryl group instead of, or in addition to, the one or more alkyl group. In a further case, which is also an alkylamido as the term is defined herein, the carbonyl carbon atom is bonded to a nitrogen atom which is bonded to one or more alkenyl group instead of, or in addition to, the one or more alkyl and or/aryl group. In a further case, which is also an alkylamido as the term is defined herein, the carbonyl carbon atom is bonded to a nitrogen atom which is bonded to one or more alkynyl group instead of, or in addition to, the one or more alkyl, alkenyl and/or aryl group.

The term "formyl" as used herein refers to a group containing a carbonyl moiety wherein the group is bonded via the carbonyl carbon atom. The carbonyl carbon atom is also bonded to a hydrogen atom.

"Oxo" refers to the =O radical.

The term "alkoxycarbonyl" as used herein refers to a group containing a carbonyl moiety wherein the group is bonded via the carbonyl carbon atom. The carbonyl carbon atom is also bonded to an oxygen atom which is further bonded to an alkyl group. Alkoxycarbonyl also includes the group where a carbonyl carbon atom is also bonded to an oxygen atom which is further bonded to an alkyenyl group. Alkoxycarbonyl also includes the group where a carbonyl carbon atom is also bonded to an oxygen atom which is further bonded to an alkynyl group. In a further case, which is included in the definition of alkoxycarbonyl as the term is defined herein, and is also included in the term "aryloxycarbonyl," the carbonyl carbon atom is bonded to an oxygen atom which is bonded to an aryl group instead of an alkyl group.

The term "arylcarbonyl" as used herein refers to a group containing a carbonyl moiety wherein the group is bonded via the carbonyl carbon atom. The carbonyl carbon atom is also bonded to an aryl group.

The term "carboxy" as used herein refers to a group containing a carbonyl moiety wherein the group is bonded via the carbonyl carbon atom. The carbonyl carbon atom is also bonded to a hydroxy group or oxygen anion so as to result in a carboxylic acid or carboxylate. Carboxy also includes both the protonated form of the carboxylic acid and the salt form. For example, carboxy can be understood as COOH or $CO_2H$.

The term "alkylthio" as used herein refers to a sulfur atom connected to an alkyl, alkenyl, or alkynyl group as defined herein.

The term "arylthio" as used herein refers to a sulfur atom connected to an aryl group as defined herein.

The term "alkylsulfonyl" as used herein refers to a sulfonyl group connected to an alkyl, alkenyl, or alkynyl group as defined herein.

The term "alkylsulfinyl" as used herein refers to a sulfinyl group connected to an alkyl, alkenyl, or alkynyl group as defined herein.

The term "dialkylaminosulfonyl" as used herein refers to a sulfonyl group connected to a nitrogen further connected to two alkyl groups, as defined herein, and which can optionally be linked together to form a ring with the nitrogen. This term also includes the group where the nitrogen is further connected to one or two alkenyl groups in place of the alkyl groups.

The term "dialkylamino" as used herein refers to an amino group connected to two alkyl groups, as defined herein, and which can optionally be linked together to form a ring with the nitrogen. This term also includes the group where the nitrogen is further connected to one or two alkenyl groups in place of the alkyl groups.

The term "dialkylamido" as used herein refers to an amido group connected to two alkyl groups, as defined herein, and which can optionally be linked together to form a ring with the nitrogen. This term also includes the group where the nitrogen is further connected to one or two alkenyl groups in place of the alkyl groups.

The term "substituted" or "substituent" as used herein refers to a group that is substituted with one or more groups including, but not limited to, the following groups: deuterium (D), halogen (e.g., F, Cl, Br, and I), R, OR, OC(O)N$(R)_2$, CN, NO, $NO_2$, $ONO_2$, azido, $CF_3$, $OCF_3$, methylenedioxy, ethylenedioxy, ($C_3$-$C_{20}$)heteroaryl, $N(R)_2$, $Si(R)_3$, SR, SOR, $SO_2R$, $SO_2N(R)_2$, $SO_3R$, $P(O)(OR)_2$, OP(O)$OR)_2$, C(O)R, C(O)C(O)R, $C(O)CH_2C(O)R$, C(S)R, C(O)OR, OC(O)R, $C(O)N(R)_2$, C(O)N(R)OH, $OC(O)N(R)_2$, $C(S)N(R)_2$, $(CH_2)_{0-2}N(R)C(O)R$, $(CH_2)_{0-2}N(R)N(R)_2$, N(R)N(R)C(O)R, N(R)N(R)C(O)OR, $N(R)N(R)CON(R)_2$, N(R)$SO_2R$, $N(R)SO_2N(R)_2$, N(R)C(O)OR, N(R)C(O)R, N(R)C(S)R, $N(R)C(O)N(R)_2$, $N(R)C(S)N(R)_2$, N(COR)COR, N(OR)R, $C(=NH)N(R)_2$, C(O)N(OR)R, or C(=NOR)R wherein R can be hydrogen, (C1-C20)alkyl or ($C_6$-$C_{20}$)aryl. Substituted also includes a group that is substituted with one or more groups including, but not limited to, the following groups: fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino and dialkylamido. Where there are two or more adjacent substituents, the substituents can be linked to form a carbocyclic or heterocyclic ring. Such adjacent groups can have a vicinal or germinal relationship, or they can be adjacent on a ring in, e.g., an ortho-arrangement. Each instance of substituted is understood to be independent. For example, a substituted aryl can be substituted with bromo and a substituted heterocycle on the same compound can be substituted with alkyl. It is envisaged that a substituted group can be substituted with one or more non-fluoro groups. As another example, a substituted group can be substituted with one or more non-cyano groups. As another example, a substituted group can be substituted with one or more groups other than haloalkyl. As yet another example, a substituted group can be substituted with one or more groups other than tert-butyl. As yet a further example, a substituted group can be substituted with one or more groups other than trifluoromethyl. As yet even further examples, a substituted group can be substituted with one or more groups other than nitro, other than methyl, other than methoxymethyl, other than dialkylaminosulfonyl, other than bromo, other than chloro, other than amido, other than halo, other than benzodioxepinyl, other than polycyclic heterocyclyl, other than polycyclic substituted aryl, other than methoxycarbonyl, other than alkoxycarbonyl, other than thiophenyl, or other than nitrophenyl, or groups meeting a combination of such descriptions. Further, substituted is also understood to include fluoro, cyano, haloalkyl, tert-butyl, trifluoromethyl, nitro, methyl, methoxymethyl, dialkylaminosulfonyl, bromo, chloro, amido, halo, benzodioxepinyl, polycyclic heterocyclyl, polycyclic substituted aryl, methoxycarbonyl, alkoxycarbonyl, thiophenyl, and nitrophenyl groups.

The compounds can contain one or more asymmetric centers and thus give rise to enantiomers, diastereomers, and other stereoisomeric forms that are defined, in terms of absolute stereochemistry, as (R)- or (S)—. Unless stated otherwise, it is intended that all stereoisomeric forms of the compounds disclosed herein are contemplated by this disclosure. When the compounds contain alkene double bonds, and unless specified otherwise, it is intended that both E and Z geometric isomers (e.g., cis or trans) are included. Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional nontoxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

As used herein, the phrase "therapeutically effective amount" refers to an amount of a drug or pharmaceutical agent that elicits the biological or medicinal response in a subject (i.e. a tissue system, animal, or human) that is being sought by a researcher, veterinarian, medical doctor, or other clinician, which includes, but is not limited to, alleviation of the symptoms of the disease or disorder being treated. In one aspect, the therapeutically effective amount is that amount of an active which may treat or alleviate the disease or symptoms of the disease at a reasonable benefit/risk ratio applicable to any medical treatment.

It is also appreciated that the dose, whether referring to monotherapy or combination therapy, is advantageously selected with reference to any toxicity, or other undesirable side effect, that might occur during administration of one or more of a compound of formula (A) or (B). Further, it is appreciated that the co-therapies described herein may allow for the administration of lower doses of a compound of formula (A) or (B) that show such toxicity, or other undesirable side effect, where those lower doses are below thresholds of toxicity or lower in the therapeutic window than would otherwise be administered in the absence of a cotherapy.

As used herein, the term "administering" includes all means of introducing a compound of formula (A) or (B) and compositions comprising same to the host animal, including but are not limited to oral (po), intravenous (iv), intramuscular (im), subcutaneous (sc), transdermal, inhalation, buccal, ocular, sublingual, vaginal, rectal, and the like. A compound of formula (A) or (B) and compositions comprising same can be administered in unit dosage forms and/or formulations containing conventional nontoxic pharmaceutically-acceptable excipients, carriers, adjuvants, and/or vehicles.

As used herein, the phrase "pharmaceutical composition" or "composition" refers to a mixture of one or more of a compound of formula (A) or (B) in accordance with the present teachings, or pharmaceutically acceptable salts, solvates, hydrates thereof, with other chemical components, such as pharmaceutically acceptable excipients. The purpose of a pharmaceutical composition is to facilitate administration of a compound to a subject. Pharmaceutical compositions suitable for the delivery of a compound of formula (A)

or (B) and methods for their preparation will be readily apparent to those skilled in the art. Such compositions and methods for their preparation can be found, for example in *Remington's Pharmaceutical Sciences,* $19^{th}$ *Edition* (Mack Publishing Company, 1995).

The term "solvate" means a compound, or a salt thereof, that further includes a stoichiometric or non-stoichiometric amount of solvent bound by non-covalent intermolecular forces. Where the solvent is water, the solvate is a hydrate.

The term "radical" as used herein refers to a fragment of a molecule, wherein that fragment has an open valence for bond formation. A monovalent radical has one open valence such that it can form one bond with another chemical group. Unless otherwise specified, a radical of a molecule (e.g., a radical of an FAPα targeting moiety) as used herein is created by removal of one hydrogen atom from that molecule to create a monovalent radical with one open valence at the location where the hydrogen atom was removed. Where appropriate, a radical can be divalent, trivalent, etc., wherein two, three or more hydrogen atoms or other groups have been removed to create a radical which can bond to two, three, or more chemical groups. Where appropriate, a radical open valence can be created by removal of other than a hydrogen atom (e.g., a halogen), or by removal of two or more atoms (e.g., a hydroxyl group), as long as the atoms removed are a small fraction (20% or less of the atom count) of the total atoms in the molecule forming the radical. A radical can be formed from a molecule by removal of a hydroxyl group.

The cleavable bond or bonds can be present in the interior of a cleavable linker and/or at one or both ends of a cleavable linker. It should be appreciated that such physiological conditions resulting in bond cleavage include standard chemical hydrolysis reactions that occur, for example, at physiological pH, or as a result of compartmentalization into a cellular organelle such as an endosome having a lower pH than cytosolic pH. Illustratively, the bivalent linkers described herein can undergo cleavage under other physiological or metabolic conditions, such as by the action of a glutathione mediated mechanism. It is appreciated that the lability of the cleavable bond can be adjusted by including functional groups or fragments within the bivalent linker L that are able to assist or facilitate such bond cleavage, also termed anchimeric assistance. The lability of the cleavable bond can also be adjusted by, for example, substitutional changes at or near the cleavable bond, such as including alpha branching adjacent to a cleavable disulfide bond, increasing the hydrophobicity of substituents on silicon in a moiety having a silicon-oxygen bond that can be hydrolyzed, homologating alkoxy groups that form part of a ketal or acetal that can be hydrolyzed, and the like. In addition, it is appreciated that additional functional groups or fragments can be included within the bivalent linker L that are able to assist or facilitate additional fragmentation of the compounds after bond breaking of the releasable linker, when present.

The terms "subject," "patient," and "individual" are used interchangeably. None of the terms are intended to require the continuous supervision of a medical professional. The subject can be any mammal, for example a human.

The term "treating" encompasses therapeutic treatment (e.g., a subject with signs and symptoms of a disease state being treated) and/or prophylactic treatment. Prophylactic treatment encompasses prevention and inhibition or delay of progression of a disease state.

The term "therapeutically effective amount" refers to that amount of one or more compounds described herein (e.g., a compound of the formula (I)) that elicits a biological or medicinal response in a tissue system, animal or human, that is being sought by a researcher, veterinarian, medical doctor or other clinician, which includes alleviation of the signs or symptoms of the disease or disorder being treated.

The term "kit" refers to an assembly of materials that are used in performing a method in accordance with the present teachings. The components of the kit can be provided in packaged combination in the same or in separate containers, depending on their cross-reactivities and stabilities, and in liquid or in solid form. The amounts and proportions of components provided in the kit can be selected to provide optimum results for a particular application. While the components to be administered (e.g., to a patient) can be provided in separate physical forms (e.g., a kit containing one or more compositions and one or more fluids), it is to be understood that in other embodiments, all of the components that are to be introduced to the patient can be provided together in one common physical form (e.g., one composition or one fluid).

Unless defined otherwise, all technical and scientific terms used herein have the same meaning as commonly understood to one of ordinary skill in the art to which this disclosure belongs. Although any methods, devices, and materials similar or equivalent to those described herein can be used in the practice or testing of the present teachings, the preferred methods, devices and materials are now described.

The terms and expressions, which have been employed, are used as terms of description and not of limitation. In this regard, where certain terms are defined under "Definitions" and are otherwise defined, described, or discussed elsewhere in the "Detailed Description," all such definitions, descriptions, and discussions are intended to be attributed to such terms. There also is no intention in the use of such terms and expressions of excluding any equivalents of the features shown and described or portions thereof.

Furthermore, while subheadings, e.g., "Definitions," are used in the "Detailed Description," such use is solely for ease of reference and is not intended to limit any disclosure made in one section to that section only; rather, any disclosure made under one subheading is intended to constitute a disclosure under each and every other subheading.

It will be understood by one of ordinary skill in the relevant arts that other suitable modifications and adaptations to the compositions and methods described herein are readily apparent from the description of the disclosure contained herein in view of information known to the ordinarily skilled artisan, and can be made without departing from the scope of the disclosure. Having now described the present disclosure in detail, the same will be more clearly understood by reference to the following examples, which are included herewith for purposes of illustration only and are not intended to be limiting of the disclosure.

It is to be understood that the elements and features recited in the appended claims can be combined in different ways to produce new claims that likewise fall within the scope of the present disclosure. Thus, whereas the dependent claims appended below depend from only a single independent or dependent claim, it is to be understood that these claims can, alternatively, be made to depend in the alternative from any preceding claim—whether independent or dependent—and that such new combinations are to be understood as forming a part of the present.

EXAMPLES

The present invention can be better understood by reference to the following examples which are offered by way of illustration. The present invention is not limited to the examples given herein.

General. Boc-protected amino acids (e.g. glycine, D/L-alanine, etc.) were purchased from Chem-Impex International, Inc. 4,4-difluoro-L-prolinamide-HCl was purchased from Chem Impex International, Inc. (R)-Boro-Proline-(+)-Pinanediol-HCl was purchased from AABLOCKS LLC. 2-$CH_3$NHBoc-isonicotinic acid was purchased from Enamine. 2,5-dichloroisonicotinic acid was purchased from TCI. 7-hydroxyquinoline-4-carboxylic acid was purchased from Crysdot. All other reagents were purchased from SIGMA-Aldrich and Fischer Scientific and used as received. Thin layer chromatography (TLC) was carried out on Merck silica gel 60 F254 TLC plates. Silica gel column chromatography was performed using silica gel (60-120 μm particle size). Preparative reverse-phase high performance liquid chromatography (RP-PLC) was performed on a Waters, XBridge™ Prep C18, μm; 19×100 mm column, mobile phase A=20 mM ammonium acetate buffer, pH 5 or 7, B=acetonitrile, system with gradients in 30 minutes, 13 mL/minute, λ=220/254/280 nm.

Synthesis

The FAP ligand $F_1$ and fluorescent-dye conjugates were synthesized following a previously published procedure: WO2018111989A1, which is incorporated by reference as if fully set forth herein.

Scheme 7. Synthesis of fibroblast activation protein a (FAP) ligand JFL.

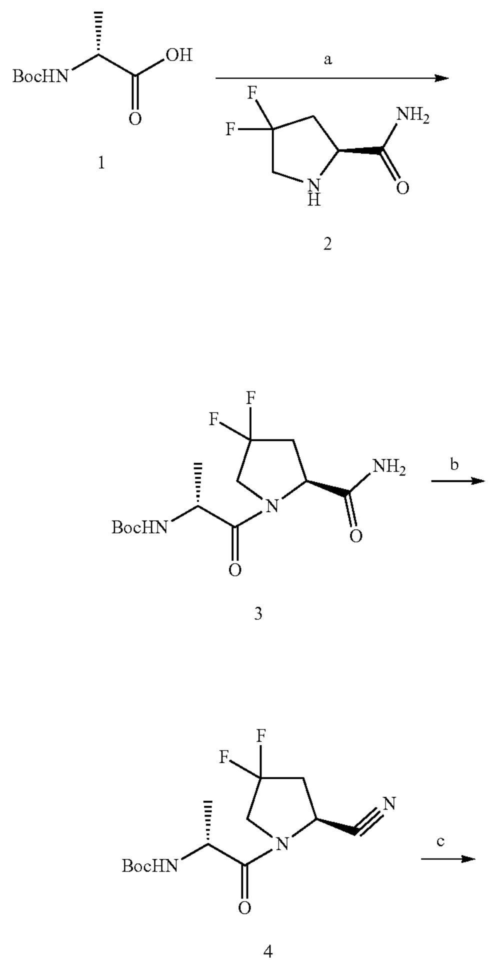

1

2

3

4

-continued

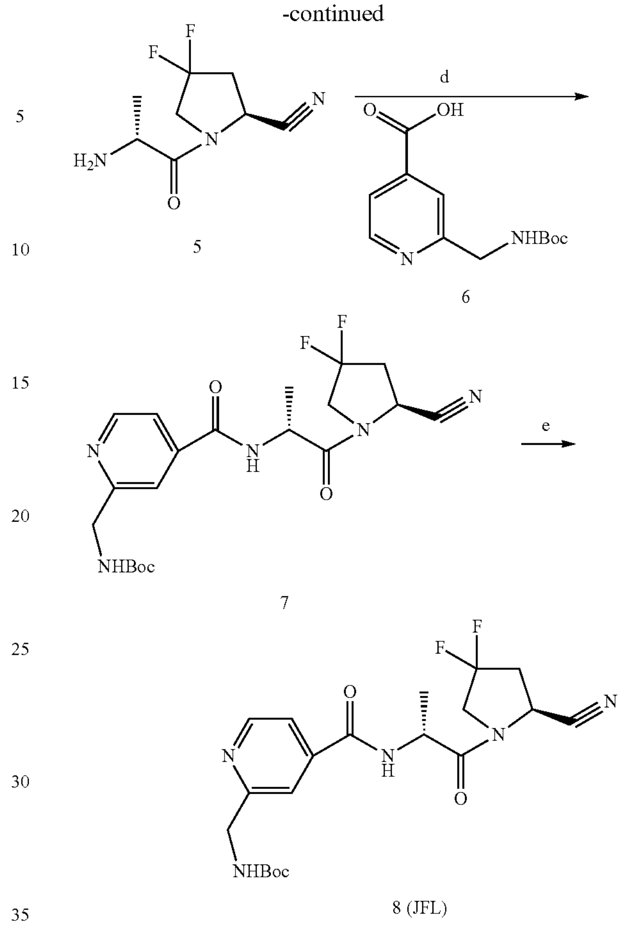

5

6

7

8 (JFL)

Reagents and conditions a) HATU, Anhy. DIPEA, Any. DMF, rt; b) TFAA, Anh. DCM, Anhy. Pyrine, rt; c) TFA, rt; d) HATU, Anhy. DIPEA, Anhy. DMF, rt; e) TFA, rt.

Synthesis of F1 (compound 8) was initiated by coupling compound 1 and 2 by using HATU as coupling agent to yield compound 3. The amide group on compound 3 was converted to nitrile (compound 4) by using TFAA. Compound 4 was then subjected to Boc deprotection followed by coupling with compound 6 to yield the yield compound 7. Compound 8 was obtained by deprotecting the Boc group on compound 7. Compound 8 is alternatively referred to herein as the FAP ligand JFL.

Compound 3. To a solution of 1 in anhydrous DMF equivalence of compound 2 and HATU was added. To the above solution anhydrous DIPEA (5 eq) was added and stirred under argon atmosphere for 6 h. The crude product was purified using RP-HPLC [A=2 Mm ammonium acetate buffer (pH 7.0), B=acetonitrile, solvent gradient 0% B to 80% B in 35 min] to yield the requisite product. LRMS-LC/MS (m/z): $[M+H]^+$ calcd for $C_{13}H_{21}F_2N_3O_4$, 321.32. Found: 323. LC/MS trace of Compound 3 is shown in FIG. 7.

Compound 4, The HPLC purified compound 3 was dissolved in anhy, DCM. To this solution was added anhydrous pyridine (1 eq) followed by TFAA (1 eq). The reaction mixture was stirred at room temperature for 1 h. Completion of the reaction was monitored by LC/MS. The crude product was purified using RP-HPLC [A=2 Mm ammonium acetate buffer (pH 7.0), B-acetonitrile, solvent gradient 0% B to 80% B in 35 min] to yield the requisite product. LRMS- LC/MS (m/z): $[M+H]^+$ calcd for $C_{13}H_{19}F_2N_3O_3$, 303.31. Found: 305 g/mol. LC/MS trace of Compound 4 is shown in FIG. 8.

Compound 7, Compound 4 was dissolved in TFA and stirred at room temperature for 30 min. Completion of the reaction was monitored through LC/MS. TFA was evaporated by using rotary evaporator and the compound 5 was dried under high vacuum and used further without any purification. LC/MS trace of Compound 5 is shown in FIG. 9. To a solution of compound 5, compound 6 (1 eq) and HATU (1 eq) in DMF DIPEA (5 eq) was added and stirred under argon atmosphere for 6 h. The completion of the reaction was monitored by LC/MS. The crude compound 7 was purified using RP-HPLC [A=2 Mm ammonium acetate buffer (pH 7.0), B=acetonitrile, solvent gradient 0% B to 80% B in 35 min] to yield the requisite product. LRMS-LC/MS (m/z): $[M+H]^+$ calcd for $C_{20}H_{25}F_2N_5O_4$, 437.45. Found: 438 g/mol. LC/MS trace of Compound 7 is shown in FIG. 10.

Compound 8. Compound 7 was dissolved in TFA and stirred ad room temperature for 30 min. TFA was removed by using rotary evaporator and the crude compound 8 was used for the next reaction without any further purification. LRMS-LC/MS (m/z): $[M+H]^+$ calcd for $C_{15}H_{17}F_2N_5O_2$, 337.33. Found: 338 g/mol.

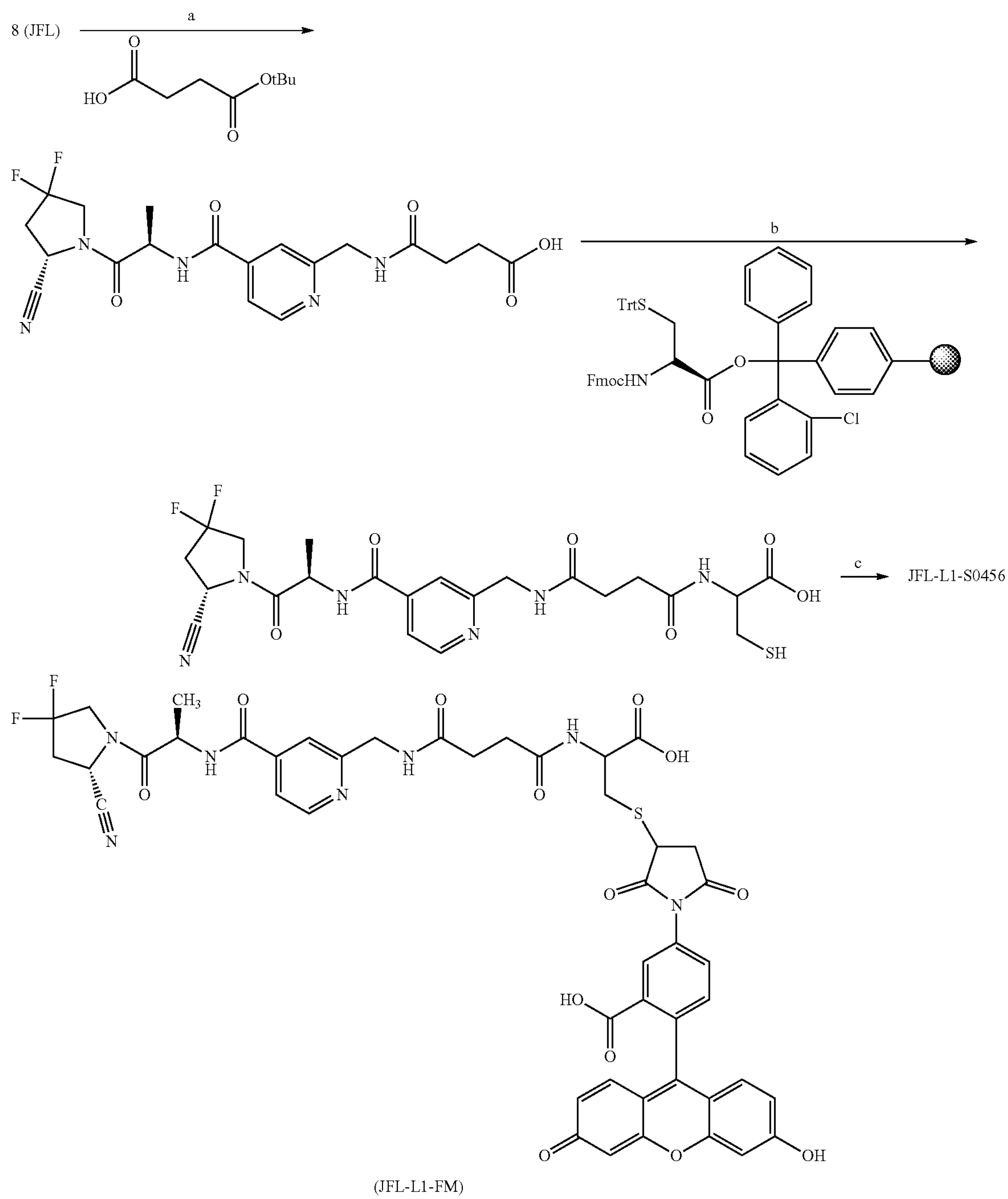

(JFL-L1-FM)

(JFL-L1-S0456)

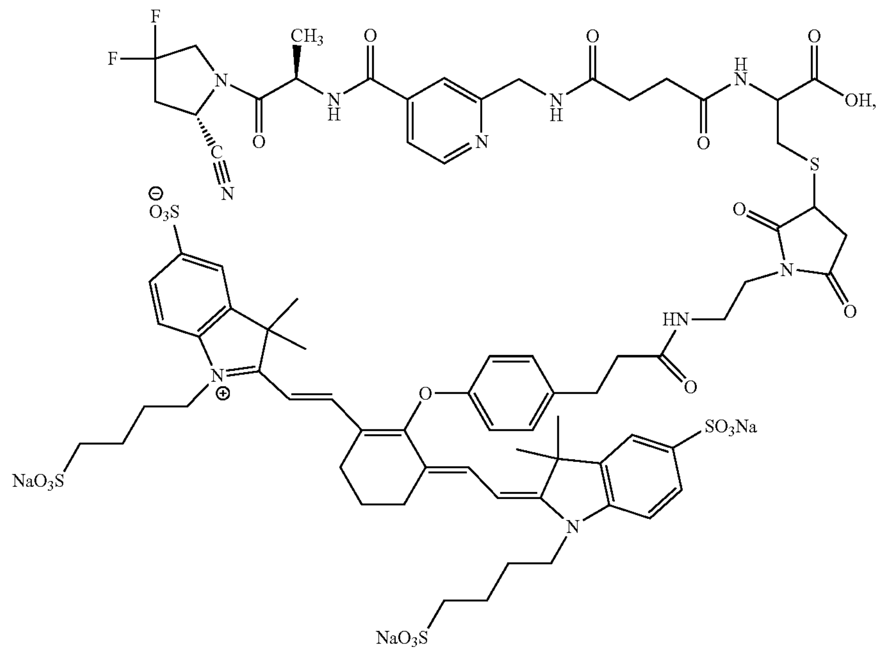

Scheme 2. Synthesis of JFL-L1-S0456 and JFL-L1-FM. Reagents and conditions: a) (i) HATU, Anhy. DIPEA, Anhy. DMF, rt. (ii) TFA, rt; b) (i) PyBop, Anhy. DMF, Any. DIPEA, rt. (ii) TFA/$H_2O$/TIPS/EDT (92.5:2.5:2.5:2.5), 1 h; c) DMSO, DIPEA, S0456 maleimide, rt; d) DMSO, DIPEA, fluorescein maleimide, rt.

Compound 8 was linked to a spacer and is designated herein as JFL-L1. The ligand was linked to the linker partially in solution phase and by standard solid phase peptide synthesis. This was then coupled with the maleimide derivatives of FM or S0456 to yield JFL-L1-FM or JFL-L1-S0456 respectively. Intermediates and final conjugates were purified by HPLC and characterized by using LC/MS and UPLC.

Compound 10. To the solution of compound 8 in anhy. DMF was added, compound 9 (1 eq), HATU (1 eq) and DIPEA (10 eq). The reaction mixture was stirred under argon atmosphere for 6 h. The completion of reaction was monitored by LC/MS. The crude compound 10 was purified by using RP-HPLC [A=2 Mm ammonium acetate buffer (pH 7.0), B=acetonitrile, solvent gradient 0% B to 80% B in 35 min] to yield the requisite product. LRMS-LC/MS (m/z): $[M+H]^+$ calcd for $C_{19}H_{21}F_2N_5O_5$, 437.4; found 438.

Synthesis of JFL-L1. As described in Scheme 2, the compound was prepared by solid phase peptide synthesis. PyBop, Anhy. DMF, Anhy. DIPEA, compound 10, and the H-Cys(Trt)2-chlorotrityl resin were combined at room temperature. The final product was cleaved from the resin using the standard cocktail solution of TFA:Water:TIPS:Ethanedithiol (95%:2.5%:2.5%:2.5%). Crude JFL-L1 was purified by using RP-HPLC [A=2 Mm ammonium acetate buffer (pH 5.0), B=acetonitrile, solvent gradient 0% B to 80% B in 35 min] to yield the requisite product. LRMS-LC/MS (m/z): $[M+H]^+$ calcd for $C_{22}H_{26}F_6N_6O_6S$, 540.54; found 541.

Synthesis of JFL-L1-FM and JFL-L1-S0456. JFL-L1 was dissolved in DMSO and 5 eq of DIPEA. To this reaction mixture was added either 1 eq of fluorescein maleimide or S0456 maleimide. The reaction mixture was stirred under argon atmosphere for 1 h and the completion of the reaction was monitored by LC/MS. The crude compounds JFL-L1-FM and JFL-L1-S0456 were purified by using RP-HPLC [A=2 Mm ammonium acetate buffer (pH 7.0), B=acetonitrile, solvent gradient 0% B to 80% B in 35 min] to yield the requisite product. The LCMS characterization of JFL-L1-FM and JFL-L1-S0456 are as follows. LRMS-LC/MS (m/z): $[M+H]^+$ calcd for $C_46H_{39}F_2N_7Oi_3S$, 967.91; found 968. LRMS-LC/MS (m/z): $[M+H]^+$ calcd for $C_{75}H_{85}F_2N_{10}Na_3O_{22}S_5$, 1745.82.35; found 1747.

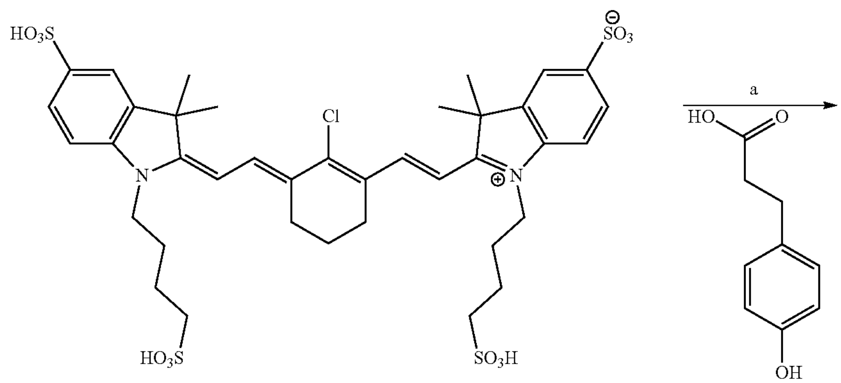

11

12

-continued

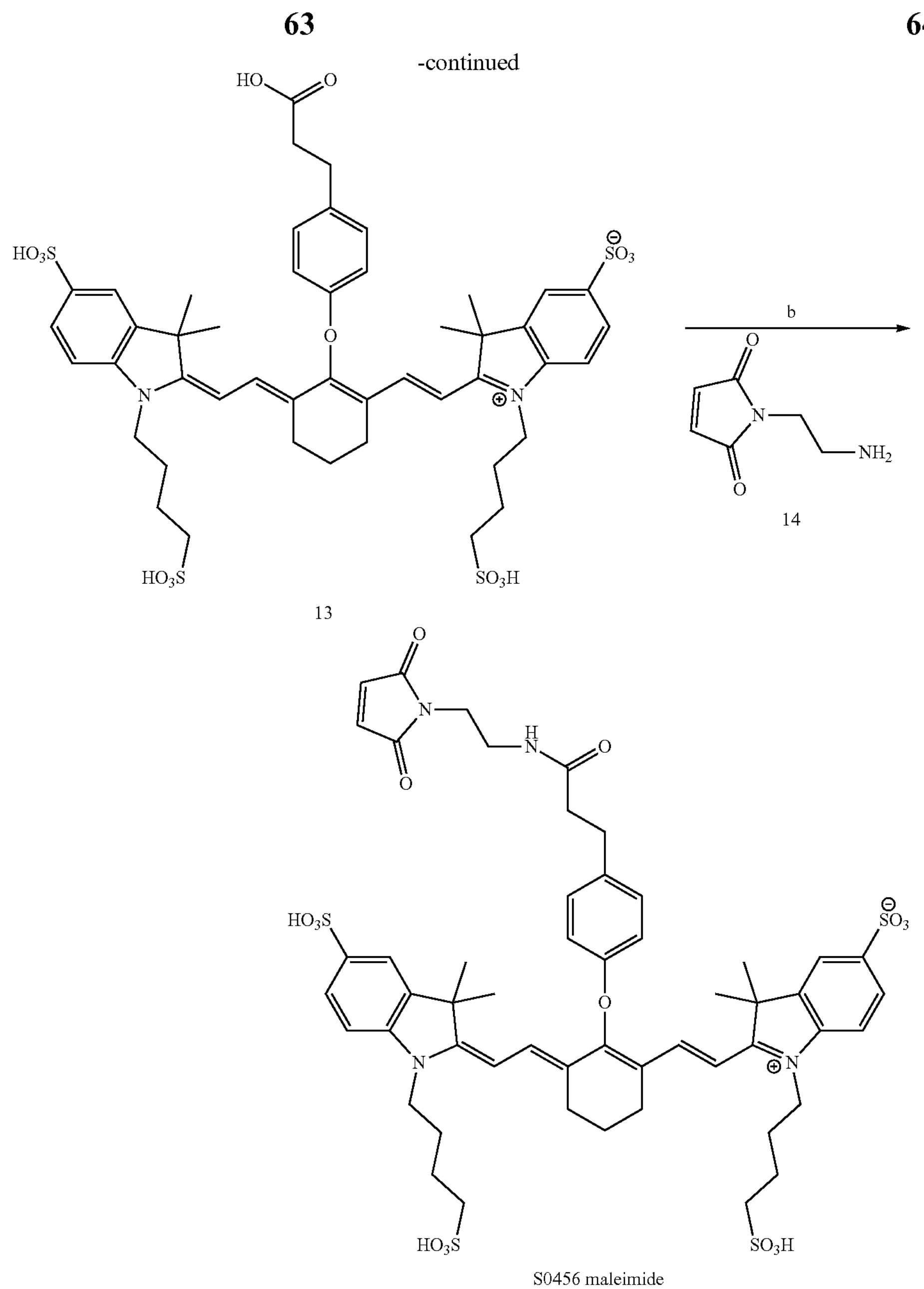

13

14

S0456 maleimide

Scheme 3. Synthesis of S0456 maleimide. Reagents and conditions: a) KOH, $H_2O$, rt-100° C.; b) HATU, Anhy. DIPEA, Anhy. DMF, rt.

Cell Culture

Cell lines were purchased from ATCC. DMEM and RPMI were purchased from Gibco. EMEM and FBS were purchased from VWR. Penicillin/streptomycin were purchased from Corning. Puromycin was purchased from Sigma Aldrich. All cell lines were cultured in the recommended media containing 10% FBS, 100 units/mL penicillin, and 100 µg/mL streptomycin. 0.1 µL/mL of puromycin was added to the media for transfected cell lines. All cell lines were incubated at 37° C. in a humidified atmosphere with 5% $CO_2$.

KB and human FAP-transfected HEK-FAP and HT1080-FAP cells were cultured in a medium consisting RPMI-1640, DMEM and EMEM. The cells used in this study was initiated by thawing frozen vials from a master stock saved from the original cell lines upon purchasing from ATCC. All the experiments were performed with in two to five passages following thawing of the cells. No mycoplasma test was performed for any of the cell lines.

Animal Husbandry

C57BL6/6-NCrl (Strain code: 027) mice were purchased from Charles River and maintained on normal rodent chow. 5-6 weeks old female athymic nu/nu mice were purchased from Harlan Laboratories and allowed access to normal rodent chow and water ad libitum. The animals were maintained on a standard 12 h light-dark cycle. All the animal procedures were approved by the Purdue Animal Care and Use Committee (PACUC) in accordance with NIH guidelines.

Confocal Binding Studies of FAP-Targeting Ligand

Method 1: HT1080-FAP cells (1000000 cells/well) were seeded in 4 well confocal plates. The cells were allowed to grow as a monolayer over 24 hours at 37° C. and incubate with various concentration of conjugate, concentration ranging from 1.5 nM (lowest) to 25 nM (highest) in 1% FBS in PBS for 1 h at 37° C. washed the cells with 1% FBS (3×500 μL), finally left the cells in 500 μl of 1% FBS followed by acquired the images with confocal microscopy, with 100 fold excess of competition ligand shown in FIG. 4.

Live Cell Imaging of FAP-FITC Internalization

HLF1-hFAP cells were seeded in a glass-bottom dish and incubated with adequate amount of endosome tracker (Rab7a-RFP, ThermoFisher) overnight. Cells were then incubated with FAP-FITC (10 nM) for 1 hour at 4° C., followed by staining with 5 nM DRAQ5 nucleus dye (ThermoFisher). Cells were washed 3× with PBS, then spatial localization of FAP-FITC was monitored at the indicated time under ambient temperature by confocal microscopy (FV 1000, Olympus). Confocal images were further processed by FV10-ASW, Olympus software.

Ex Vivo Fluorescence Imaging and Biodistribution:

Female nu/nu athymic (5-6 weeks old) mice were subcutaneously injected with $5\times10^6$ KB cells in 0.1 mL sterile PBS. Tumors were allowed to grow to approximately 250-600 $mm^3$ before initiating imaging studies. Each tumor—bearing mouse was intravenously injected (via tail vein) with 5 nmol to 10 nmol of the compound either in the presence or absence of a 10- to 500-fold excess of unlabeled ligand. Whole body images were acquired using AMI instrument at two different time points 2 h and 6 h post injection for all the tumors followed by euthanized using $CO_2$ asphyxiation. After performing whole-body imaging, organs of interest were harvested and imaged to quantitate fluorescence accumulation. The image acquisition parameters were as follows: i) lamp level-high; ii) excitation-745 nm; iii) emission-810; iv) binning (M) 4M; (v) f-stop-4; (vi) FOV-12.5; (vii) acquisition time, 5 s; (viii) power 55.

NUMBERED EMBODIMENTS

Embodiment 1 relates to a compound of formula (A) or (B):

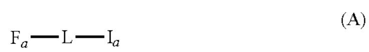

(A)

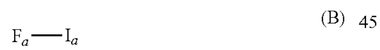

(B)

or a pharmaceutically acceptable salt thereof, wherein:

$F_a$ is a fibroblast activation protein alpha (FAPα) targeting moiety having a structure represented by the following formula (X):

(X)

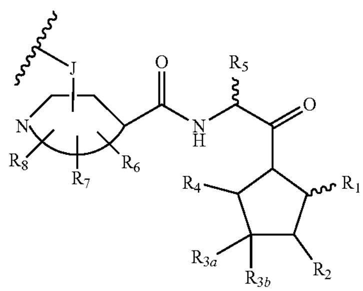

wherein:

$R_1$ is selected from the group consisting of —H, —CN, —$B(OH)_2$, —C(O)alkyl, —C(O)aryl, —C═CC(O)aryl, —C═C—$S(O)_2$aryl, —$CO_2H$, —$SO_3H$, —$SO_2NH_2$, —$PO_3H_2$, and 5-tetrazolyl, $R_2$, $R_{3a}$, $R_{3a}$ and $R_4$ are each independently selected from the group consisting of —H, —OH, halogen, —$C_{1-6}$ alkyl, —O—$C_{1-6}$alkyl, and —S—$C_{1-6}$alkyl, $R_5$ is —$CH_3$, $R_6$, $R_7$, and $R_8$ are each independently selected from the group consisting of —H, —OH, oxo, halogen, $CF_3$, —$C_{1-6}$alkyl, —O—$C_{1-6}$alkyl, —S—$C_{1-6}$alkyl, —$NR_9R_{10}$, —$OR_{11}$, -$Het_2$, and —$Ar_2$; each of —$C_{1-6}$ alkyl being optionally substituted with from 1 to 3 substituents selected from —OH and halogen;

$R_9$, $R_{10}$, and Ru are each independently selected from the group consisting of —H, —OH, oxo, halogen, $CF_3$, —$C_{1-6}$alkyl, —O—$C_{1-6}$alkyl, —S—$C_{1-6}$alkyl, and —$Ar_3$, $Ar_2$ and $Ar_3$ are each independently a 5- or 6-membered aromatic monocycle optionally comprising 1 or 2 heteroatoms selected from O, N, and S; each of $Ar_2$ and $Ar_3$ being optionally and independently substituted with from 1 to 3 substituents selected from —$NR_{12}R_{13}$, —$C_{1-6}$alkyl, —O—$C_{1-6}$alkyl, and —S—$C_{1-6}$alkyl, $R_{12}$ and $R_{13}$ are each independently selected from the group consisting of —H, —OH, $CF_3$, —$C_{1-6}$alkyl, —O—$C_{1-6}$alkyl, and —S—$C_{1-6}$alkyl, $Het_2$ is a 5- or 6-membered non-aromatic monocycle optionally comprising 1 or 2 heteroatoms selected from O, N and S; $Het_2$ being optionally substituted with from 1 to 3 substituents selected from —$NR_{14}R_{15}$, —$C_{1-6}$ alkyl, —O—$C_{1-6}$alkyl, and —S—$C_{1-6}$alkyl, $R_{14}$ and $R_{15}$ are each independently selected from the group consisting of —H, —OH, halogen, $CF_3$, —$C_{1-6}$alkyl, —O—$C_{1-6}$alkyl, and —S—$C_{1-6}$alkyl;

the fragment:

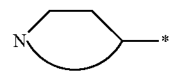

represents a 5- to 10-membered N-containing aromatic or non-aromatic mono- or bicyclic heterocycle, said heterocycle optionally further comprising 1 to 3 heteroatoms selected from O, N, and S, wherein * indicates an attachment point to a carbonyl as shown in formula (X); and J is selected from the group consisting of a bond, —$C_{1-3}$alkyl, —$C_{1-3}$alkyl-NH—, C═O, and —O—;

L is a linker;

$I_a$ is an inhibitor of a signaling pathway necessary for fibrosis in cancer-associated fibroblasts (CAFs); and the compound is not

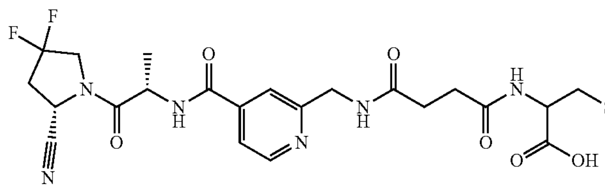
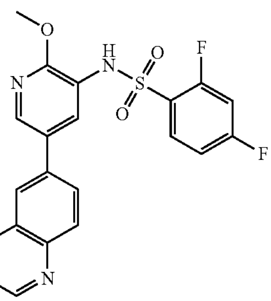

Embodiment 2 relates to a compound of Embodiment 1, wherein $R_1$ is —CN, —$CH_2CN$ or —$B(OH)_2$.

Embodiment 3 relates to a compound of Embodiment 1 or 2, wherein $R_2$ is hydrogen.

Embodiment 4 relates to a compound of any preceding Embodiment, wherein $R_{3a}$ and Rb are halogen.

Embodiment 5 relates to a compound of any one of Embodiments 1-3, wherein $R_{3a}$ and $R_{3b}$ are fluoro.

Embodiment 6 relates to a compound of any one of Embodiments 1-3, wherein $R_{3a}$ and $R_{3b}$ are hydrogen.

Embodiment 7 relates to a compound of any preceding Embodiment, wherein $R_4$ is hydrogen.

Embodiment 8 relates to a compound of any preceding Embodiment, wherein the fragment:

is

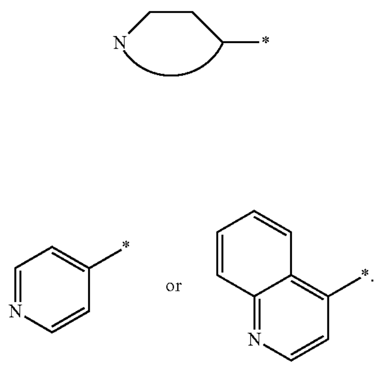

or

Embodiment 9 relates to a compound of any preceding Embodiment, wherein $R_6$, $R_7$, and $R_8$ are hydrogen.

Embodiment 10 relates to a compound of any one of Embodiments 1-8, wherein $R_6$ and $R_7$ are hydrogen.

Embodiment 11 relates to a compound of any preceding Embodiment, wherein $R_8$ is hydrogen or chloro.

Embodiment 12 relates to a compound of any preceding Embodiment, wherein J is selected from the group consisting of a bond, —$CH_2$—, —$CH_2$—NH—, and —O—.

Embodiment 13 relates to a compound of formula (A) or (B):

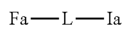 (A)

 (B)

or a pharmaceutically acceptable salt thereof, wherein: $F_a$ is formula (Y)

(Y)

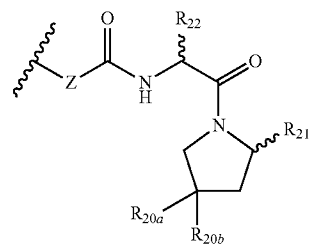

wherein

Z is selected from the group consisting of

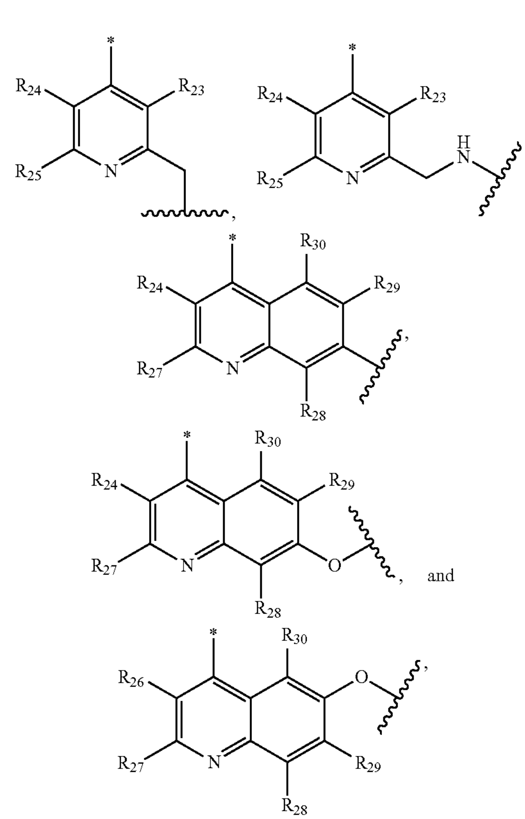

, , and , wherein* indicates an attachment point to a carbonyl as shown in formula (Y);

indicates an attachment point to L in formula (A) and $I_a$ in formula (B);

$R_{20a}$ and $R_{20b}$ are the same or different and are each independently selected from the group consisting of hydrogen, halogen, and $C_{1-4}$alkyl;

$R_{21}$ is selected from the group consisting of $C_{1-4}$alkyl, nitrile, isonitrile, and boronic acid;

$R_{22}$ is $—CH_3$, $R_{23}$ and $R_{24}$ are the same or different, and are each independently selected from the group consisting of hydrogen, halogen, and $C_{1-4}$alkyl;

$R_{25}$ is selected from the group consisting of hydrogen, methoxy, halogen, $CF_3$, and $C_{1-4}$alkyl;

$R_{26}$ and $R_{27}$ are the same or different, and are each independently selected from the group consisting of hydrogen, halogen, and $C_{1-4}$alkyl;

$R_{28}$, $R_{29}$, and $R_{30}$ are the same or different, and are each independently selected from the group consisting of hydrogen, methoxy, halogen, $CF_3$, and $C_{1-4}$alkyl; and the compound is not

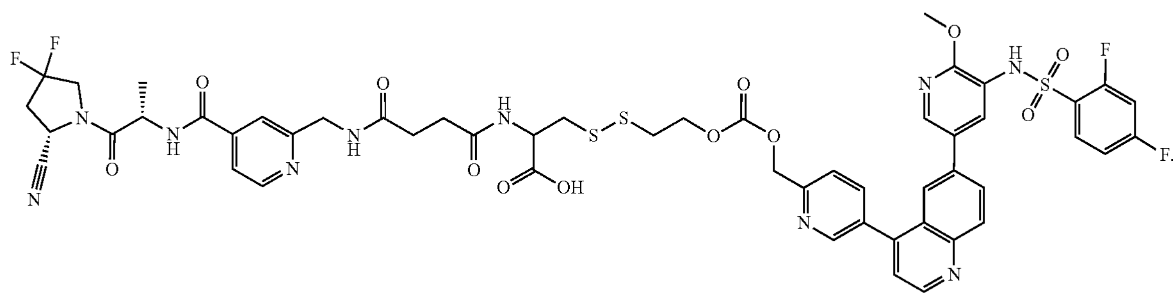

Embodiment 14 relates to a compound of Embodiment 13, wherein $R_{20a}$ and $R_{20b}$ are halogen.

Embodiment 15 relates to a compound of Embodiment 13 or 14, wherein $R_{20a}$ and $R_{20b}$ are fluoro.

Embodiment 16 relates to a compound of Embodiment 13, wherein $R_{20a}$ and $R_{20b}$ are hydrogen.

Embodiment 17 relates to a compound of any one of Embodiments 13-16, wherein $R_{21}$ is $—CH_2CN$ or boronic acid.

Embodiment 18 relates to a compound of any one of Embodiments 13-17, wherein $R_{23}$ and $R_{25}$ are hydrogen.

Embodiment 19 relates to a compound of any one of Embodiments 13-18, wherein $R_{24}$ is hydrogen or chloro.

Embodiment 20 relates to a compound of any one of Embodiments 13-19, wherein $R_{26}$, $R_{27}$, $R_{28}$, $R_{29}$, and $R_{30}$ are hydrogen.

Embodiment 21 relates to a compound of any one of Embodiments 13-20, wherein $F_a$ is selected from the group consisting of:

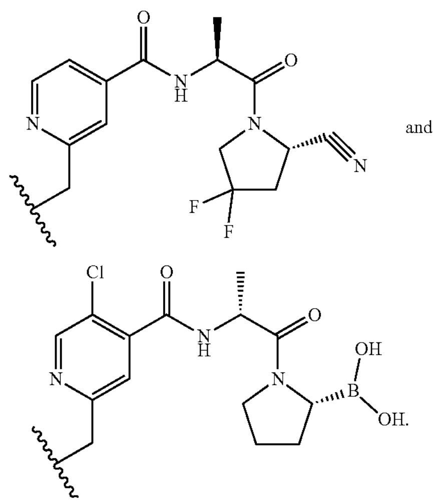

and

Embodiment 23 relates to a compound of any one of Embodiments 1-21, wherein L is or

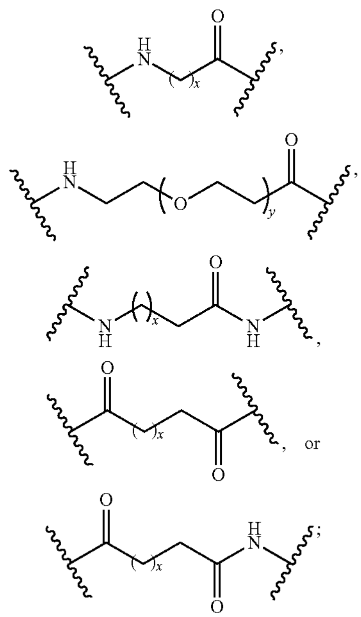

x is an integer from 0 to 10: and y is an integer from 3 to 100.

Embodiment 23 relates to a compound of any one of Embodiments 1-21, wherein L is

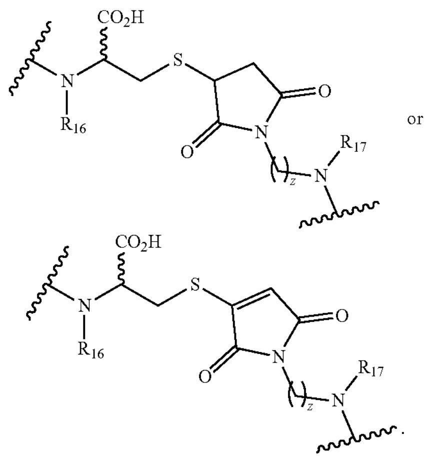

Embodiment 24 relates to a compound of any one of Embodiments 1-21, wherein L is

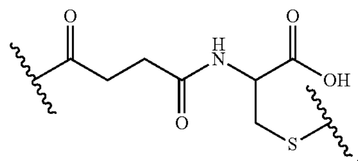 [SMILES: *SCC(NC(=O)CCC(*)=O)C(=O)O]

Embodiment 25 relates to a compound of any one of Embodiments 1-21, wherein L is

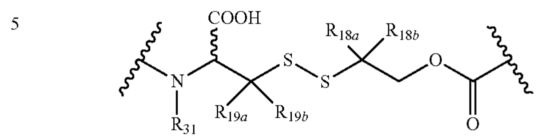

$R_{18a}$, $R_{18b}$, $R_{19a}$, and $R_{19b}$ are independently H or $C_{1-6}$alkyl; and $R_{31}$ is H or $C_{1-6}$alkyl.

Embodiment 26 relates to a compound of any one of Embodiments 1-25, wherein $I_a$ is a kinase inhibitor for TGFβRI/Smad.

Embodiment 27 relates to a compound of any one of Embodiments 1-25, wherein $I_a$ is a kinase inhibitor for Wnt/s-catenin.

Embodiment 28 relates to a compound of any one of Embodiments 1-25, wherein $I_a$ is a kinase inhibitor for VEGFR1, VEGFR2, VEGFR3, FGFR1, FGFR2, or PDGFR.

Embodiment 29 relates to a compound of any one of Embodiments 1-25, wherein $I_a$ is a kinase inhibitor for FAK or ROCK.

Embodiment 30 relates to a compound of any one of Embodiments 1-25, wherein $I_a$ is a pan kinase inhibitor for PI-3 kinase/mTOR.

Embodiment 31 relates to a compound of any one of Embodiments 1-25, wherein $I_a$ is a radical of:

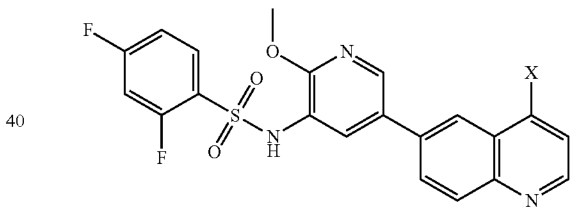

wherein X is

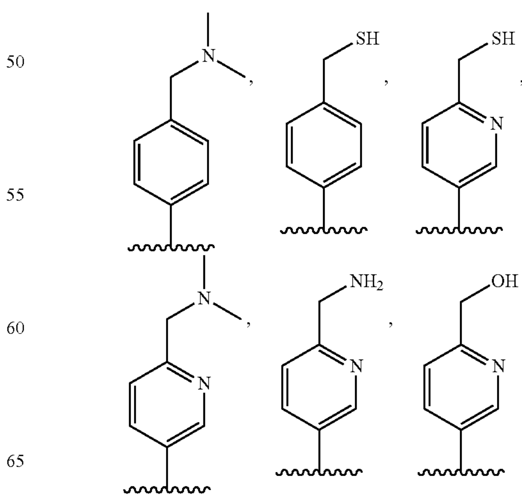

-continued

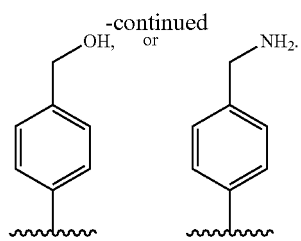

Embodiment 33 relates to a compound of any one of Embodiments 1-25, wherein $I_a$ is:

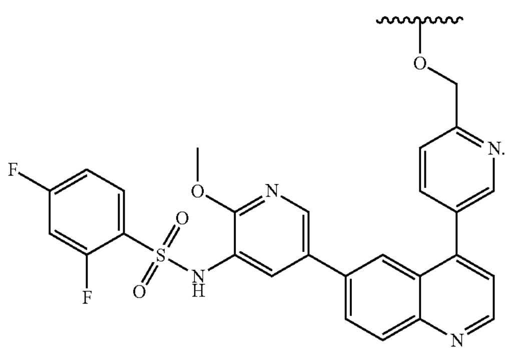

Embodiment 33 relates to a compound of any one of Embodiments 1-32, wherein the targeting ligand to FAPα has a binding affinity to FAP in the range between about 1 nM to about 25 nM.

Embodiment 34 relates pharmaceutical composition comprising a compound of any one of any one of Embodiments 1-33 and one or more pharmaceutically acceptable excipients.

Embodiments 35 relates to a method of treating a cancer (for example, a solid tumor) in a subject in need thereof, the method comprising administering to the subject an effective amount of a compound of any one of any one of Embodiments 1-33 or a pharmaceutical composition of Embodiment 34 to the subject, wherein the tumor microenvironment (TME) comprises a cancer-associated fibroblast (CAF).

Embodiment 36 relates to a method of Embodiment 35, wherein the compound reduces collagen I deposition from activated fibroblasts.

Embodiment 37 relates to a method of Embodiment 35 or 36, wherein the compound comprises an antifibrotic agent effective against CAFs.

Embodiment 38 relates to a method of any one of Embodiment 35-37, wherein the CAF-containing tumor treated by the conjugate comprises stromal cells.

Embodiment 39 relates to a method of any one of Embodiment 35-39, wherein the collagen I in the extracellular matrix of the TME is reduced.

Embodiment 40 relates to a method of any one of Embodiment 3540, wherein the compound reduces the hydroxyproline production of fibroblasts.

Embodiment 41 relates to a method of any one of Embodiment 35-40, wherein the cancer is selected from the group consisting of lung cancer, bone cancer, pancreatic cancer, skin cancer, cancer of the head, cancer of the neck, cutaneous melanoma, intraocular melanoma, uterine cancer, ovarian cancer, endometrial cancer, leiomyosarcoma, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland cancer of the parathyroid gland, non-small cell lung cancer, small cell lung cancer, cancer of the adrenal gland, sarcoma of soft tissue, cancer of the urethra, cancer of the penis, prostate cancer, chronic leukemia, acute leukemia, lymphocytic lymphomas, pleural mesothelioma, cancer of the bladder, Burkitt's lymphoma, cancer of the ureter, cancer of the kidney, renal cell carcinoma, carcinoma of the renal pelvis, neoplasms of the central nervous system (CNS), primary CNS lymphoma, spinal axis tumors, brain stem glioma, pituitary adenoma, cholangiocarcinoma, Hurthle cell thyroid cancer, and adenocarcinoma of the gastroesophageal junction.

Embodiment 42 relates to a method of treating a fibrotic disease or disorder in a subject in need thereof, the method comprising: administering to the subject an effective amount of a compound of any one of Embodiments 1-33 or a pharmaceutical composition of Embodiment 34.

Embodiment 43 relates to a method of any one of Embodiment 44, wherein the fibrotic disease or disorder is selected from the group consisting of: pulmonary fibrosis (e.g., idiopathic pulmonary fibrosis), liver fibrosis, heart fibrosis, kidney fibrosis, mediastinal fibrosis, retroperitoneal cavity fibrosis, bone marrow fibrosis (aka, myelofibrosis), skin fibrosis, or scleroderma (systemic sclerosis).

Embodiment 44 relates to a method of Embodiment 42 or 43, wherein the fibrotic disease or disorder is treated by reducing fibrosis.

The invention claimed is:

1. A compound of formula (A) or (B):

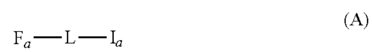
(A)

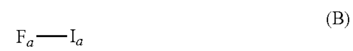
(B)

or a pharmaceutically acceptable salt thereof, wherein:

$I_a$ is

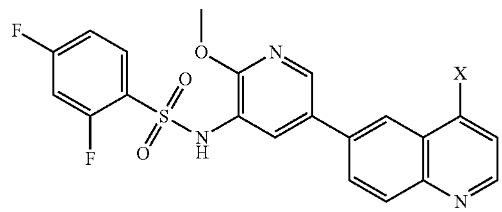

wherein X is:

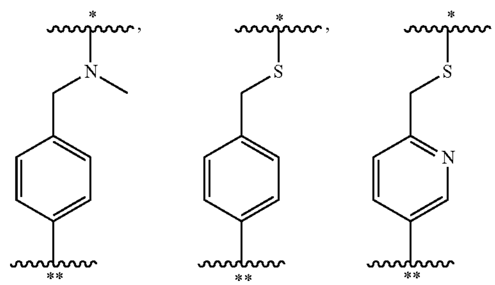

-continued

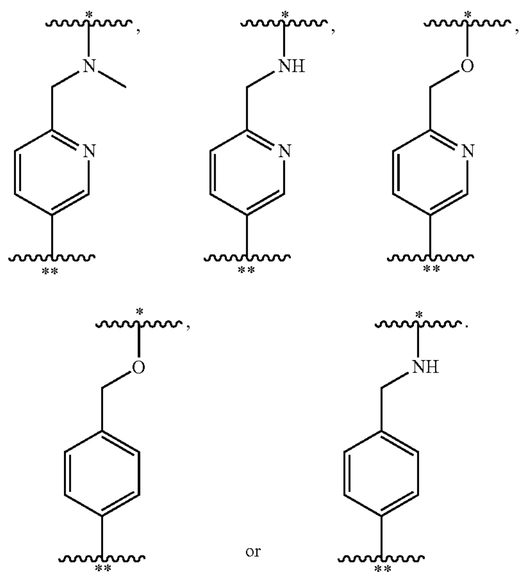

or wherein * denotes the point of attachment of X to $I_a$ or L or $F_a$; and ** denotes the point of attachment of X to:

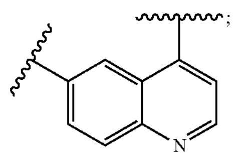 [SMILES: *c1ccc2nccc(*)c2c1]

L is

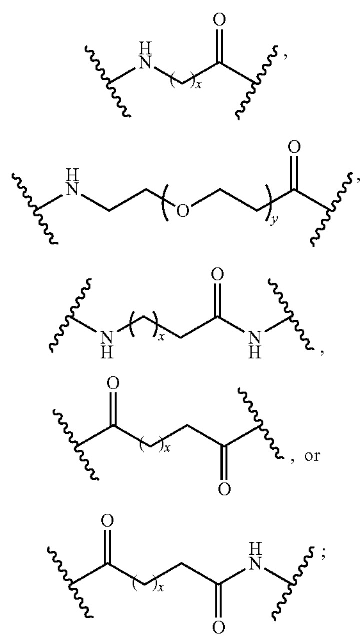

x is an integer from 0 to 10; and y is an integer from 3 to 100; or

L is:

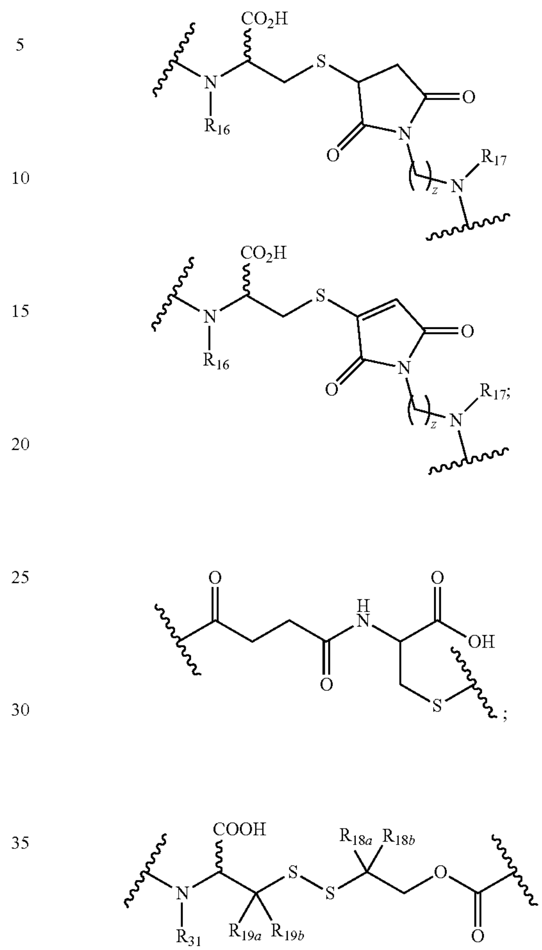

wherein:

$R_{18a}$, $R_{18b}$, $R_{19a}$, and $R_{19b}$ are independently H or $C_{1-6}$alkyl; and $R_{31}$ is H or $C_{1-6}$alkyl;

$F_a$ is a fibroblast activation protein alpha (FAPα) targeting moiety having a structure represented by the following formula (X):

(X)

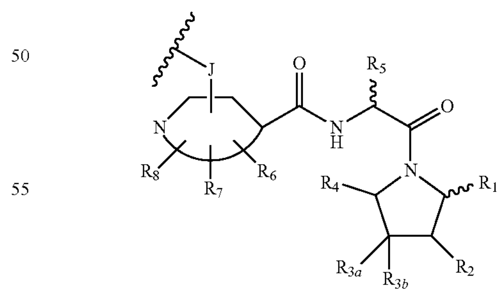

wherein:

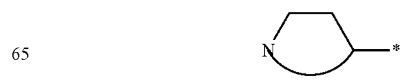

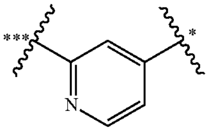

or

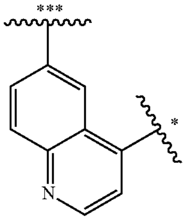

wherein *** denotes the point of attachment to J;

$R_1$ is selected from the group consisting of —H, —CN, —$B(OH)_2$, —C(O)alkyl, —C(O)aryl, —C═CC(O)aryl, —C═C—$S(O)_2$aryl, —$CO_2H$, —$SO_3H$, —$SO_2NH_2$, —$PO_3H_2$, and 5-tetrazolyl, $R_2$, $R_{3a}$, $R_{3b}$ and $R_4$ are each independently selected from the group consisting of —H, —OH, halogen, —$C_{1-6}$alkyl, —O—$C_{1-6}$alkyl, and —S—$C_{1-6}$alkyl, $R_5$ is —$CH_3$, $R_6$, $R_7$, and $R_8$ are each independently selected from the group consisting of —H, —OH, oxo, halogen, $CF_3$, —$C_{1-6}$alkyl, —O—$C_{1-6}$alkyl, —S—$C_{1-6}$alkyl, —$NR_9R_{10}$, —$OR_{11}$, —$Het_2$, and —$Ar_2$;

each of —$C_{1-6}$alkyl being optionally substituted with from 1 to 3 substituents selected from —OH and halogen;

$R_9$, $R_{10}$, and $R_{11}$ are each independently selected from the group consisting of —H, —OH, oxo, halogen, $CF_3$, —$C_{1-6}$alkyl, —O—$C_{1-6}$alkyl, —S—$C_{1-6}$alkyl, and —$Ar_3$, $Ar_2$ and $Ar_3$ are each independently a 5- or 6-membered aromatic monocycle optionally comprising 1 or 2 heteroatoms selected from O, N, and S; each of $Ar_2$ and $Ar_3$ being optionally and independently substituted with from 1 to 3 substituents selected from —$NR_{12}R_{13}$, —$C_{1-6}$alkyl, —O—$C_{1-6}$alkyl, and —S—$C_{1-6}$alkyl, $R_{12}$ and $R_{13}$ are each independently selected from the group consisting of —H, —OH, $CF_3$, —$C_{1-6}$alkyl, —O—$C_{1-6}$alkyl, and —S—$C_{1-6}$alkyl, $Het_2$ is a 5- or 6-membered non-aromatic monocycle optionally comprising 1 or 2 heteroatoms selected from O, N and S;

$Het_2$ being optionally substituted with from 1 to 3 substituents selected from —$NR_{14}R_{15}$, —$C_{1-6}$alkyl, —O—$C_{1-6}$alkyl, and —S—$C_{1-6}$alkyl, $R_{14}$ and $R_{15}$ are each independently selected from the group consisting of —H, —OH, halogen, $CF_3$, —$C_{1-6}$alkyl, —O—$C_{1-6}$alkyl, and —S—$C_{1-6}$alkyl;

J is selected from the group consisting of a bond, —$C_{1-3}$alkyl, —$C_{1-3}$alkyl-NH—, C═O, and —O;

and the compound is not

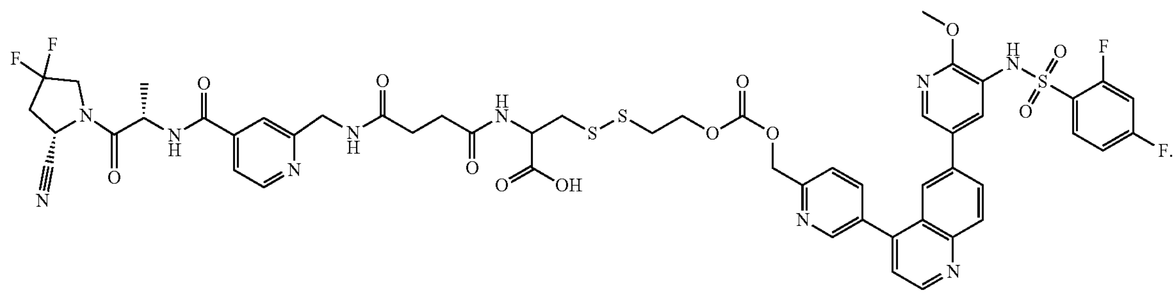 [SMILES: COc1ncc(-c2ccc3nccc(-c4ccc(COC(=O)OCCSSCC(NC(=O)CCCC(=O)NCc5cc(C(=O)N[C@@H](C)CC(=O)N6CC(F)(F)C[C@H]6C#N)ccn5)C(=O)O)nc4)c3c2)cc1NS(=O)(=O)c1ccc(F)cc1F]

2. The compound of claim 1, wherein $R_1$ is —CN, —$CH_2CN$ or —$B(OH)_2$.

3. The compound of claim 1, wherein $R_{3a}$ and $R_{3b}$ are halogen or hydrogen.

4. The compound of claim 1, wherein $R_6$, $R_7$, and $R_8$ are hydrogen.

5. The compound of claim 1, wherein $R_6$ and $R_7$ are hydrogen.

6. The compound of claim 1, wherein $R_8$ is hydrogen or chloro.

7. A compound of formula (A) or (B):

$F_a$-L-$I_a$ (A)

$F_a$-$I_a$ (B)

or a pharmaceutically acceptable salt thereof, wherein:

$I_a$ is

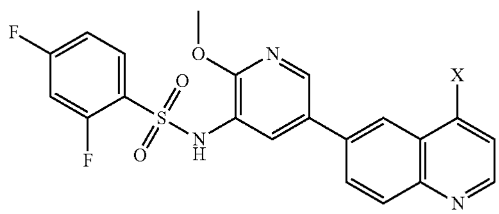

wherein X is:

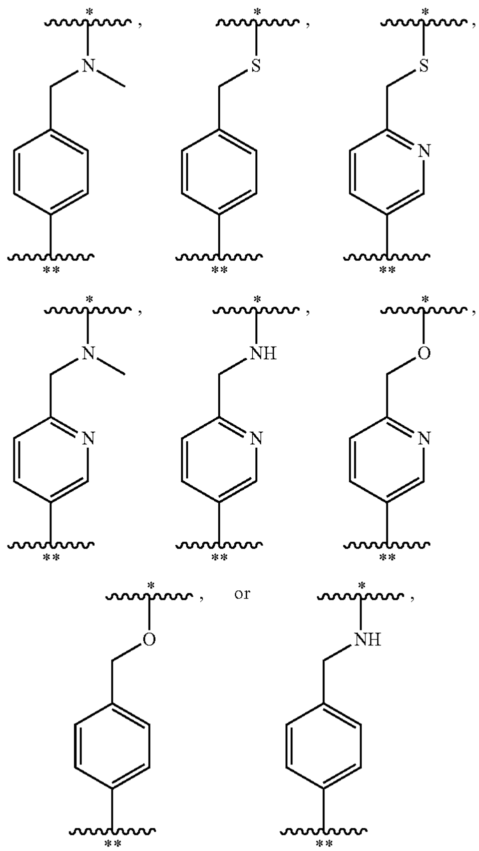

wherein * denotes the point of attachment of X to $I_a$ or L or $F_a$; and ** denotes the point of attachment of X to:

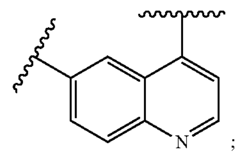 [SMILES: *c1ccc2nccc(*)c2c1]

L is

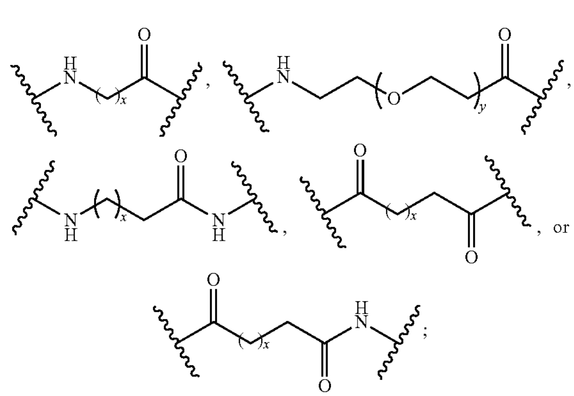

x is an integer from 0 to 10; and y is an integer from 3 to 100; or

L is:

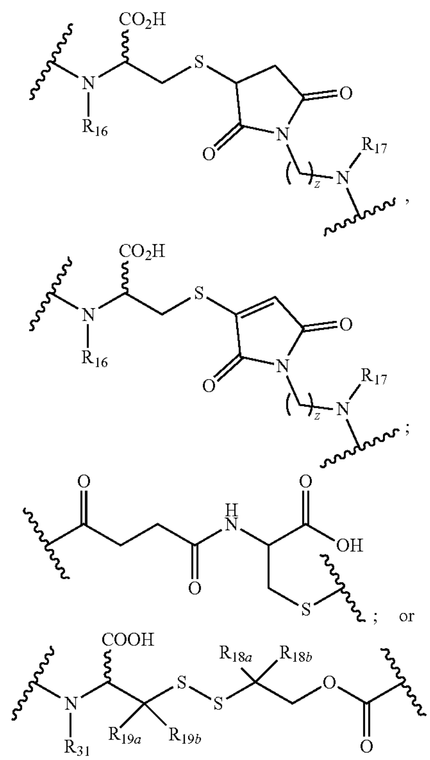

wherein:

$R_{18a}$, $R_{18b}$, $R_{19a}$, and $R_{19b}$ are independently H or $C_{1-6}$alkyl; and $R_{31}$ is H or $C_{1-6}$alkyl;

Fa is formula (Y)

(Y)

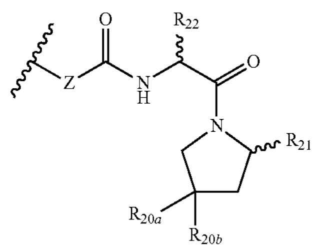

wherein

Z is selected from the group consisting of:

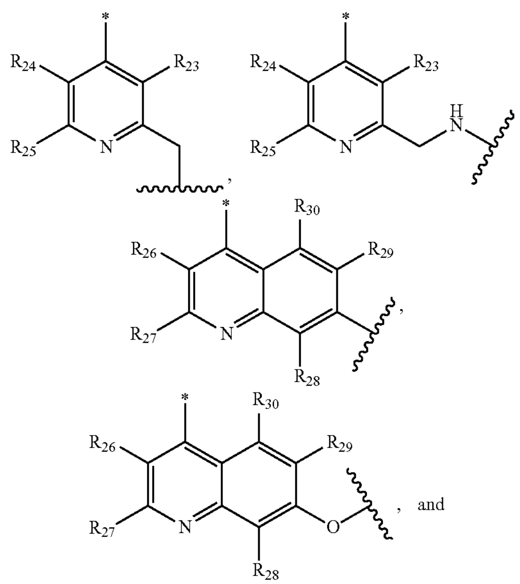

, and

-continued

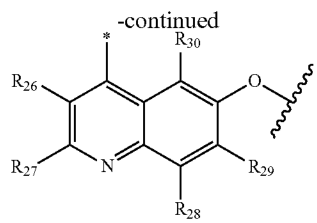

wherein * indicates an attachment point to a carbonyl as shown in formula (Y);

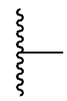

indicates an attachment point to L in formula (A) and $I_a$ in formula (B);

$R_{20a}$ and $R_{20b}$ are the same or different and are each independently selected from the group consisting of hydrogen, halogen, and $C_{1-4}$alkyl;

$R_{21}$ is selected from the group consisting of $C_{1-4}$alkyl, nitrile, isonitrile, and boronic acid;

$R_{22}$ is —$CH_3$;

$R_{23}$ and $R_{24}$ are the same or different, and are each independently selected from the group consisting of hydrogen, halogen, and $C_{1-4}$alkyl;

$R_{25}$ is selected from the group consisting of hydrogen, methoxy, halogen, $CF_3$, and $C_{1-4}$alkyl;

$R_{26}$ and $R_{27}$ are the same or different, and are each independently selected from the group consisting of hydrogen, halogen, and $C_{1-4}$alkyl;

$R_{28}$, $R_{29}$, and $R_{30}$ are the same or different, and are each independently selected from the group consisting of hydrogen, methoxy, halogen, $CF_3$, and $C_{1-4}$alkyl;

and the compound is not

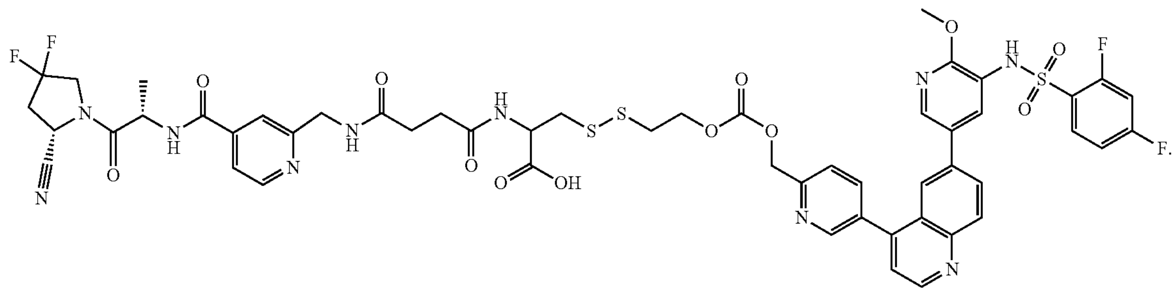 [SMILES: COc1ncc(-c2ccc3nccc(-c4ccc(COC(=O)OCCSSCC(NC(=O)CCCC(=O)NCc5cc(C(=O)N[C@@H](C)CC(=O)N6CC(F)(F)C[C@H]6C#N)ccn5)C(=O)O)nc4)c3c2)cc1NS(=O)(=O)c1ccc(F)cc1F]

8. The compound of claim 7, wherein $R_{20a}$ and $R_{20b}$ are halogen or hydrogen.

9. The compound of claim 7, wherein $R_{21}$ is —$CH_2CN$ or boronic acid.

10. The compound of claim 7, wherein $R_{23}$ and $R_{25}$ are hydrogen.

11. The compound of claim 7, wherein $R_{24}$ is hydrogen or chloro.

12. The compound of claim 7, wherein $R_{26}$, $R_{27}$, $R_{28}$, $R_{29}$, and $R_{30}$ are hydrogen.

13. The compound of claim 7, wherein $F_a$ is selected from the group consisting of:

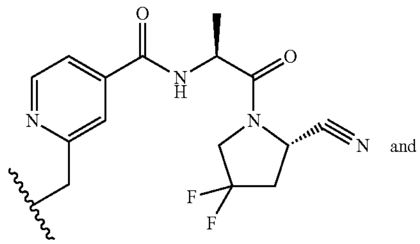

and

-continued

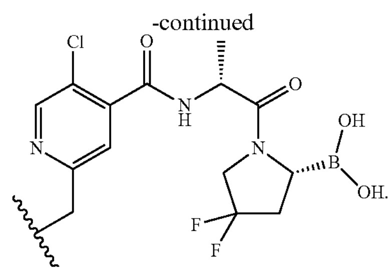

14. The compound of claim 1, wherein $I_a$ is:

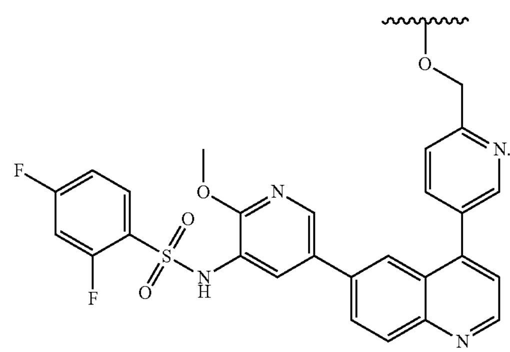 [SMILES: *OCc1ccc(-c2ccnc3ccc(-c4cnc(OC)c(NS(=O)(=O)c5ccc(F)cc5F)c4)cc23)cn1]

15. A pharmaceutical composition comprising a compound of claim 1 and one or more pharmaceutically acceptable excipients.

* * * * *